US008871516B2

(12) United States Patent
Hauber et al.

(10) Patent No.: US 8,871,516 B2
(45) Date of Patent: Oct. 28, 2014

(54) USE OF TAILORED RECOMBINASES FOR THE TREATMENT OF RETROVIRAL INFECTIONS

(75) Inventors: Joachim Hauber, Hamburg (DE); Frank Buchholz, Dresden (DE); Ilona Hauber, Hamburg (DE); Francis A Stewart, Dresden (DE); Indrani Sarkar, Kolkata (IN)

(73) Assignees: Technische Universität Dresden, Dresden (DE); Max-Planck-Gesellschaft zur Förderung der Wissenschaften E.V., München (DE); Heinrich-Pette-Institut für Experimentelle Virologie und Immunologie an der Universität Hamburg, Hamburg (DE)

( * ) Notice: Subject to any disclaimer, the term of this patent is extended or adjusted under 35 U.S.C. 154(b) by 651 days.

(21) Appl. No.: 12/522,127

(22) PCT Filed: Jan. 3, 2008

(86) PCT No.: PCT/EP2008/000021
§ 371 (c)(1),
(2), (4) Date: Feb. 22, 2010

(87) PCT Pub. No.: WO2008/083931
PCT Pub. Date: Jul. 17, 2008

(65) Prior Publication Data
US 2010/0172881 A1    Jul. 8, 2010

(30) Foreign Application Priority Data
Jan. 8, 2007   (EP) .................... 07100206

(51) Int. Cl.
*C12N 15/87*   (2006.01)
*C12N 15/10*   (2006.01)
*C12N 15/86*   (2006.01)
*C12N 15/00*   (2006.01)
*C12N 9/90*    (2006.01)
*C12N 9/00*    (2006.01)
*C07H 21/02*   (2006.01)
*C07H 21/04*   (2006.01)
*C12P 21/04*   (2006.01)
*C12P 21/06*   (2006.01)

(52) U.S. Cl.
CPC ............ *C12N 15/86* (2013.01); *C12N 2800/30* (2013.01); *C12N 15/1058* (2013.01); *C12N 2740/16043* (2013.01)
USPC ......... 435/462; 435/69.1; 435/70.1; 435/483; 435/233; 435/320.1; 435/440; 435/455; 435/463; 536/23.1; 536/23.2

(58) Field of Classification Search
None
See application file for complete search history.

(56) References Cited

U.S. PATENT DOCUMENTS

| 6,262,341 B1 | 7/2001 | Baszczynski et al. |
| 6,890,726 B1 | 5/2005 | Sauer et al. |
| 7,112,715 B2 | 9/2006 | Chambon et al. |
| 2006/0014264 A1 | 1/2006 | Sauer et al. |
| 2009/0217400 A1* | 8/2009 | Carmi et al. .................... 800/14 |

FOREIGN PATENT DOCUMENTS

| WO | 02/44409 A2 | 6/2002 |
| WO | 2005/081632 A2 * | 9/2005 |
| WO | 2008/083931 A1 | 7/2008 |

OTHER PUBLICATIONS

Abremski et al., "Studies on the Properties of P1 Site-Specific Recombination: Evidence for Topologically Unlinked Products following Recombination," *Cell* 32: 1301-1311, Apr. 1983.
Abremski et al., "Bacteriophage P1 Site-specific Recombination—Purification and Properties of the Cre Recombinase Protein," *J. Biol. Chem.* 259(3): 1509-1514, Feb. 10, 1984.
Adachi et al., "Production of Acquired Immunodeficiency Syndrome-Associated Retrovirus in Human and Nonhuman Cells Transfected with an Infectious Molecular Clone," *J. Virol* 59(2): 284-291, Aug. 1986.
Alper et al., "Tuning genetic control through promoter engineering," *Proc. Natl. Acad. Sci. USA* 102(36): 12678-12683, Sep. 6, 2005.
Beyer et al., "Oncoretrovirus and Lentivirus Vectors Pseudotyped with Lymphocytic Choriomeningitis Virus Glycoprotein: Generation, Concentration, and Broad Host Range," *J. Virol.* 76(3): 1488-1495, Feb. 2002.
Blackard et al., "Transmission of Human Immunodeficiency Type 1 Viruses with Intersubtype Recombinant Long Terminal Repeat Sequences," *Virology* 254: 220-225, 1999.
Bloom et al., "Evolving strategies for enzyme engineering," *Curr. Opin. Struct. Biol.* 15: 447-452, 2005.
Buchholz et al., "Different thermostabilities of FLP and Cre recombinases: implications for applied site-specific recombination," *Nucl. Acids Res.* 24(21): 4256-4262, 1996.
Buchholz et al., "Improved properties of FLP recombinase evolved by cycling mutagenesis," *Nat. Biotechnol.* 16: 657-662, Jul. 1998.
Buchholz et al., "Alteration of Cre recombinase site specificity by substrate-linked protein evolution," *Nat. Biotechnol.* 19: 1047-1052, Nov. 2001.

(Continued)

*Primary Examiner* — Celine Qian
*Assistant Examiner* — Nancy J Leith
(74) *Attorney, Agent, or Firm* — Seed IP Law Group PLLC

(57) ABSTRACT

The present invention is directed to a method for preparing an expression vector encoding a tailored recombinase, wherein said tailored recombinase recombines asymmetric target sites within the LTR of proviral DNA of a retrovirus inserted into the genome of a host cell and is useful as means for excising the provirus from the genome of the host cell. The present invention further relates to an in vitro-method of optimising the treatment of a retroviral infection of a subject and to the use of tailored recombinases for the preparation of pharmaceutical compositions for reducing the viral load in a subjected infected by a retrovirus.

14 Claims, 11 Drawing Sheets

(56) References Cited

OTHER PUBLICATIONS

Chiu et al., "Cellular APOBEC3G restricts HIV-1 infection in resting CD4+ T cells," *Nature 435*: 108-114, May 5, 2005.
Chun et al., "Early establishment of a pool of latently infected, resting CD4+ T cells during primary HIV-1 infection," *Proc. Natl. Acad. Sci. USA 95*: 8869-8873, Jul. 1998.
Coates et al., "Site-directed genome modification: derivatives of DNA-modifying enzymes as targeting tools," *Trends Biotechnol. 23*(8): 407-419, Aug. 2005.
Collins et al., "Engineering proteins that bind, move, make and break DNA," *Curr. Opin. Biotechnol. 14*: 371-378, 2003.
Combes et al., "The *Streptomyces* Genome Contains Multiple Pseudo-*att*B Sites for the ψC31-Encoded Site-Specific Recombination System," *J. Bacteriol. 184*(20): 5746-5752, Oct. 2002.
Crameri et al., "DNA shuffling of a family of genes from diverse species accelerates directed evolution," *Nature 391*: 288-291, Jan. 1998.
Derossi et al., "The Third Helix of the Antennapedia Homeodomain Translocates through Biological Membranes," *J. Biol. Chem. 269*(14): 10444-10450, Apr. 8, 1994.
Derossi et al., "Cell Internalization of the Third Helix of the Antennapedia Homeodomain is Receptor-independent," *J. Biol. Chem 271*(30): 18188-18193, Jul. 26, 1996.
Donovan et al., "The end of the beginning for pluripotent stem cells," *Nature 414*: 92-97, Nov. 1, 2001.
Donzella et al., "AMD3100, a small molecule inhibitor of HIV-1 entry via the CXCR4 co-receptor," *Nature Medicine 4*(1): 72-77, Jan. 1998.
Dybul et al., "Guidelines for Using Antiretroviral Agents among HIV-Infected Adults and Adolescents," *Annals of Internal Medicine 137* (5) (Part 2): 381-433, Sep. 3, 2002.
Edelman et al., "Synthetic promoter elements obtained by nucleotide sequence variation and selection for activity," *Proc. Natl. Acad. Sci. USA 97*(7): 3038-3043, Mar. 28, 2000.
Emerman et al., "HIV-1 Regulatory/Accessory Genes: Keys to Unraveling Viral and Host Cell Biology," *Science 280*: 1880-1884, 1998.
Finzi et al., "Identification of a Reservoir for HIV-1 in Patients on Highly Active Antiretroviral Therapy," *Science 278*: 1295-1300, 1997.
Flowers et al., "Inhibition of Recombinant Human Immunodeficiency Virus Type 1 Replication by a Site-Specific Recombinase," *J. Virol. 71*(4): 2685-2692, Apr. 1997.
Gulick et al., "Treatment With Indinavir, Zidovudine, and Lamivudine in Adults With Human Immunodeficiency Virus Infection and Prior Antiretroviral Therapy," *N. Engl. J Med. 337*: 734-739, Sep. 11, 1997.
Guzman et al., "Tight Regulation, Modulation, and High-Level Expression by Vectors Containing the Arabinose $P_{BAD}$ Promoter," *J. Bacteriol. 177*(14): 4121-4130, Jul. 1995.
Hartenbach et al., "A Novel Synthetic Mammalian Promoter Derived From an Internal Ribosome Entry Site," *Biotechnology and Bioengineering 95*: 547-559, 2006.
Hauber et al., "Identification of cellular deoxyhypusine synthase as a novel target for antiretroviral therapy," *J. Clin. Invest. 115*(1): 76-85, Jan. 2005.
Hazuda et al., "Integrase Inhibitors and Cellular Immunity Suppress Retroviral Replication in Rhesus Macaques," *Science 305*: 528-532, 2004.
Hoess et al., "Mechanism of Strand Cleavage and Exchange in the Cre-*lox* Site-specific Recombination System," *J. Mol. Biol. 181*: 351-362, 1985.
Johannes et al., "Directed evolution of enzymes and biosynthetic pathways," *Curr. Opin. Microbiol. 9*: 261-267, 2006.
Kim et al., "Characterization of Cre-*lox*P Interaction in the Major Groove: Hint for Structural Distortion of Mutant Cre and Possible Strategy for HIV-1 Therapy," *J. Cell. Biochem. 80*: 321-327, 2001.
Krasnow et al., "Site-Specific Relaxation and Recombination by the Tn3 Resolvase: Recognition of the DNA Path between Oriented *res* Sites," *Cell 32*: 1313-1324, Apr. 1983.

Kulkosky et al., "HAART-Persistant HIV-1 Latent Reservoirs: Their Origin, Mechanisms of Stability and Potential Strategies for Eradication," *Curr. HIV Res. 4*: 199-208, 2006.
Lalezari et al., "Enfuvirtide, an HIV-1 Fusion Inhibitor, for Drug-Resistant HIV Infection in North and South America," *N. Engl. J. Med. 348*(22): 2175-2185, May 29, 2003.
Lee et al., "A Novel Mutant *lox*P Containing Part of Long Terminal Repeat of HIV-1 in Spacer Region: Presentation of Possible Target Site for Antiviral Strategy Using Site-Specific Recombinase," *Biochem. Biophys. Res. Comm. 253*: 588-593, 1998.
Lee et al., "An engineered *lox* sequence containing part of a long terminal repeat of HIV-1 permits Cre recombinase-mediated DNA excision," *Biochem. Cell Biol. 78*: 653-658, 2000.
Lehrman et al., "Depletion of latent HIV-1 infection in vivo: a proof-of-concept study," *Lancet 366*: 549-555, Aug. 13, 2005.
Lewandoski, "Conditional Control of Gene Expression in the Mouse," *Nat. Rev. Genet. 2*: 743-755, Oct. 2001.
Lin et al., "Enhanced cell-permeant Cre protein for site-specific recombination in cultured cells," *BMC Biotechnol. 4*:25: 1-13, 2004.
Little et al., "Antiretroviral-Drug Resistance Among Patients Recently Infected With HIV," *N. Engl. J. Med. 347*(6): 385-394, Aug. 8, 2002.
Macara, "Transport into and out of the Nucleus," *Microbiology and Molecular Biology Reviews 65*(4): 570-594, Dec. 2001.
Malim et al., "Immunodeficiency virus *rev* trans-activator modulates the expression of the viral regulatory genes," *Nature 335*: 181-183, Sep. 8, 1988.
Marcello, "Latency: the hidden HIV-1 challenge," *Retrovirology 3*:7: 1-9, Jan. 2006.
Matsumura et al., "In vitro Evolution of Beta-glucuronidase into a Beta-galactosidase Proceeds Through Non-specific Intermediates," *J. Mol. Biol. 305*: 331-339, 2001.
Minshull et al., "Protein evolution by molecular breeding," *Curr. Opin. Chem. Biol. 3*: 284-290, 1999.
Nagy, "Cre Recombinase: The Universal Reagent for Genome Tailoring," *Genesis 26*: 99-109, 2000.
Needleman et al., "A General Method Applicable to the Search for Similarities in the Amino Acid Sequence of Two Proteins," *J. Mol. Biol. 48*: 443-453, 1970.
Nolden et al., "Site-specific recombination in human embryonic stem cells induced by cell-permeant Cre recombinase," *Nat. Methods 3*(6): 461-467, Jun. 2006.
O'Doherty et al., "Human Immunodeficiency Virus Type 1 Spinoculation Enhances Infection through Virus Binding," *J. Virol. 74*(21): 10074-10080, Nov. 2000.
Pearson et al., "Improved tools for biological sequence comparison," *Proc. Natl. Acad. Sci. USA 85*: 2444-2448, Apr. 1988.
Peitz et al., "Ability of the hydrophobic FGF and basic TAT peptides to promote cellular uptake of recombinant Cre recombinase: A tool for efficient genetic engineering of mammalian genomes," *Proc. Natl. Acad. Sci. USA 99*(7): 4489-4494, Apr. 2, 2002.
Ratner et al., "Polymorphism of the 3' open reading frame of the virus associated with the acquired immune deficiency syndrome, human T-lymphotropic virus type III," *Nucl. Acids Res. 13*(22): 8219-8229, 1985.
Richard et al., "Cellular Uptake of Unconjugated TAT Peptide Involves Clathrin-dependent Endocytosis and Heparan Sulfate Receptors," *J. Biol. Chem. 280*(15): 15300-15306, Apr. 15, 2005.
Rufer et al., "Non-contact positions impose site selectivity on Cre recombinase," *Nucl. Acids Res. 30*(13): 2764-2771, 2002.
Ruhl et al., "Eukaryotic Initiation Factor 5A is a Cellular Target of the Human Immunodeficiency Virus Type 1 Rev Activation Domain Mediating *Trans*-Activation," *J. Cell. Biol. 123*(6) (Part 1): 1309-1320, Dec. 1993.
Sanger et al., "DNA sequencing with chain-terminating inhibitors," *Proc. Natl. Acad. Sci. USA 74*(12): 5463-5467, Dec. 1977.
Santoro et al., "Directed evolution of the site specificity of Cre recombinase," *Proc. Natl. Acad. Sci. USA 99*(7): 4185-4190, Apr. 2, 2002.
Saraf-Levy et al., "Site-specific recombination of asymmetric *lox* sites mediated by a heterotetrameric Cre recombinase complex," *Bioorg. Med. Chem. 14*: 3081-3089, 2006.

(56) References Cited

OTHER PUBLICATIONS

Sarkar et al., "HIV-1 Proviral DNA Excision Using an Evolved Recombinase," *Science 316*: 1912-1915, Jun. 29, 2007.

Sauer et al., "DNA recombination with a heterospecific Cre homolog identified from comparison of the *pac-c1* regions of P1-related phages," *Nucl. Acids Res. 32*(20): 6086-6095, 2004.

Schambach et al., "Equal Potency of Gammaretroviral and Lentiviral SIN Vectors for Expression of $O^6$-Methylguanine-DNA Methyltransferase in Hematopoietic Cells," *Molecular Therapy 13*(2): 391-400, Feb. 2006.

Scherr et al., "Gene Transfer into Hematopoietic Stem Cells Using Lentiviral Vectors," *Current Gene Therapy 2*: 45-55, 2002.

Shehu-Xhilaga et al., "Antiretroviral Compounds: Mechanisms Underlying Failure of HAART to Eradicate HIV-1," *Curr. Med. Chem. 12*: 1705-1719, 2005.

Shimshek et al., "Codon-Improved Cre Recombinase (iCre) Expression in the Mouse," *Genesis 32*(1): 19-26, 2002.

Smith et al., "Overlapping Genes and Information Theory," *J. Theor. Biol. 91*: 379-380, 1981.

Stark et al., "Catalysis by site-specific recombinases," *Trends Genet. 8*(12): 432-439, Dec. 1992.

Stemmer, "Rapid evolution of a protein in vitro by DNA shuffling," *Nature 370*: 389-391, Aug. 4, 1994.

Sternberg et al., "Bacteriophage P1 Site-specific Recombination. I. Recombination Between *lox*P Sites," *J. Mol. Biol. 150*: 467-486, 1981.

Van Duyne, "A Structural View of Cre-*lox*P Site-Specific Recombination," *Annu. Rev. Biophys. Biomol. Struct. 30*: 87-104, 2001.

Vives et al., "A Truncated HIV-1 Tat Protein Basic Domain Rapidly Translocates through the Plasma Membrane and Accumulates in the Cell Nucleus," *J. Biol. Chem. 272*(25): 16010-16017, Jun. 20, 1997.

Vives, "Cellular utake of the TAT peptide: an endocytosis mechanism following ionic interactions,"*J. Mol. Recognit. 16*: 265-271, 2003.

Volkert et al., "Site-Specific Recombination Promotes Plasmid Amplification in Yeast," *Cell 46*: 541-550, Aug. 15, 1986.

Voziyanov et al., "Stepwise Manipulation of DNA Specificity in Flp Recombinase: Progressively Adapting Flp to Individual and Combinatorial Mutations in its Target Site," *J. Mol. Biol. 326*: 65-76, 2003.

Yuan et al., "Laboratory-Directed Protein Evolution," *Microbiol. Mol. Biol. Rev. 69*(3): 373-392, Sep. 2005.

Altschul et al., "Gapped BLAST and PSI-BLAST: a new generation of protein database search programs," *Nucleic Acids Research 25*(17):3389-3402, 1997.

Chemnitz et al., "Excision of HIV-1 Proviral DNA using Tre-Recombinase: An Experimental Update," *Antiviral Research 86*(1):A31-A32, Apr. 2010.

Eddy, "Profile hidden Markov models," *Bioinformatics Review 14*(9):755-763, 1998.

Elliott et al., "Intercellular Trafficking and Protein Delivery by a Herpesvirus Structural Protein," *Cell 88*(2):223-233, Jan. 24, 1997.

Fawell et al., "Tat-mediated delivery of heterologous proteins into cells," *Proceedings of the National Academy Sciences USA 91*(2):664-668, Jan. 18, 1994.

Fraser et al., "Reduction of the HIV-1-infected T-cell reservoir by immune activation treatment is dose-dependent and restricted by the potency of antiretroviral drugs," *AIDS 14*(6):659-669, 2000.

GenBank Accession No. CP000470, "*Shewanella* sp. ANA-3 plasmid 1, complete sequence—Nucleotide—NCBI," download date Feb. 25, 2013, from URL=http://www.ncbi.nlm.nih.gov/nuccore/CP000470, 120 pages.

GenBank Accession No. NZ_ABEW01000015, "*Salmonella enterica*subsp. *enterica* serovar Newport str. SL317 gcontig—Nucleotide—NCBI," download date Feb. 25, 2013, from URL=http://www.ncbi.nlm.nih.gov/nuccore/156105548?report=genbank, 14 pages.

Oess et al., "Novel cell permeable motif derived from the PreS2-domain of hepatitis-B virus surface antigens," *Gene Therapy 7*(9):750-758, May 2000.

Sarkar et al., "HIV-1 Proviral DNA Excision Using an Evolved Recombinase," *Science 316*(5833):1912-1915, Jun. 29, 2007.

Surendranath et al., "SeLOX—a locus of recombination site search tool for the detection and directed evolution of site-specific recombination systems," *Nucleic Acids Research 38*(Suppl 2):W293-W298, Jun. 6, 2010.

Saraf-Levy et al., "Site-specific recombination of asymmetric *lox* sites mediated by a heterotetrameric Cre recombinase complex," *Bioorganic & Medicinal Chemistry 14*:3081-3089, 2006.

Saraf-Levy et al., "Site-specific recombination of asymmetric lox sites mediated by a heterotetrameric Cre recombinase complex," *Bioorg Med Chem 14*(9):3081-9, May 1, 2006 (Abstract).

Koresawa et al., "Synthesis of a New Cre Recombinase Gene Based on Optimal Codon Usage for Mammalian Systems," *J. Biochem.* 127:367-372 (2000).

Sternberg et al., "Bacteriophage P1 *cre* Gene and its Regulatory Region—Evidence for Multiple Promoters and for Regulation by DNA Methylation," *J. Med. Biol.* 187:197-212 (1986).

* cited by examiner

```
                    NLS                        7    9 10
M  V  P  K  K  K  R  K  V  S  N  L  L  T  L  H  H  S  L  P  A  L  P
16                                    30                35
A  D  A  T  S  D  E  V  R  K  N  L  M  D  V  F  R  D  R  P  A  P  S

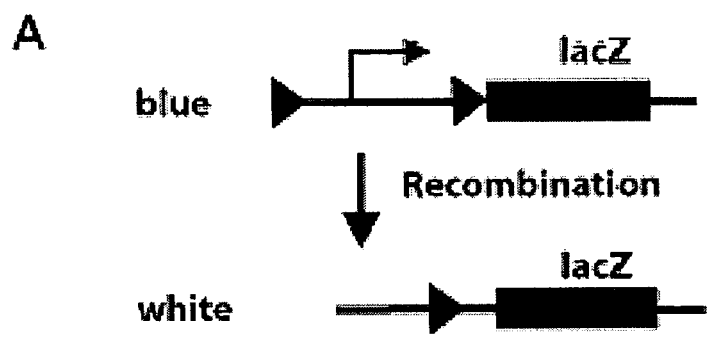
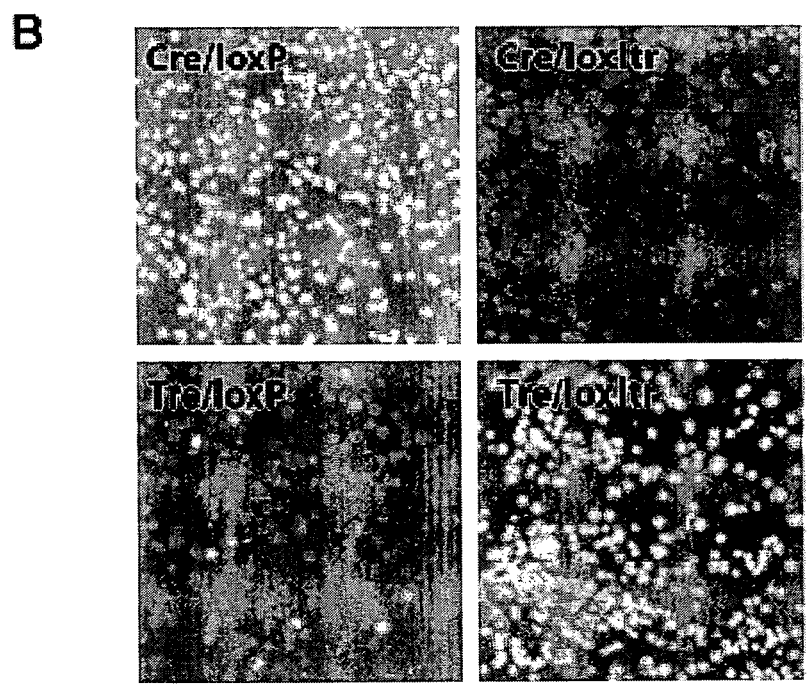
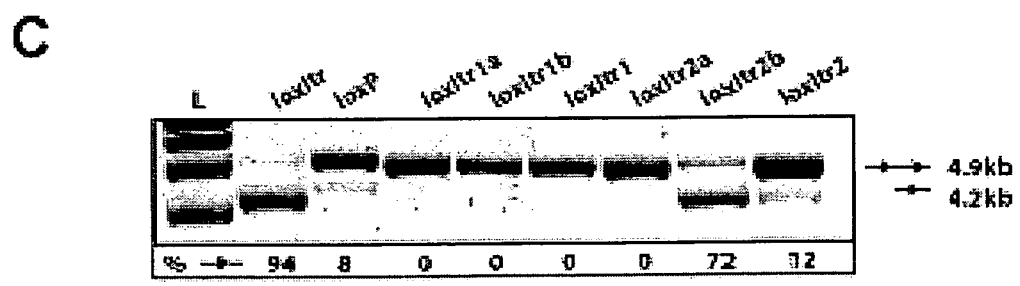
Figure 7

USE OF TAILORED RECOMBINASES FOR THE TREATMENT OF RETROVIRAL INFECTIONS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 440088_13_401USPC_13_SEQUENCE_13_LISTING.txt. The text file is 14 KB, was created on Jan. 21, 2014, and is being submitted electronically via EFS-Web.

The present invention is directed to a method for preparing an expression vector encoding a tailored recombinase, wherein said tailored recombinase recombines asymmetric target sites within the LTR of proviral DNA of a retrovirus inserted into the genome of a host cell. Such tailored recombinases recognising asymmetric target sites within the LTR of proviral DNA are means for excising the provirus from the genome of the host cell. The present invention is further directed to the use of tailored recombinases for the preparation of pharmaceutical compositions for reducing the viral load in a subjected infected by a retrovirus. An in vitro-method of optimising the treatment of a retroviral infection of a subject comprising the tailoring of recombinases specifically recognising and recombining asymmetric target sites sequences within the proviral DNA of the retrovirus the subject is infected with is a further subject of the present invention.

TECHNICAL BACKGROUND

Retroviral infections such as for example infections by the human immunodeficiency virus (HIV) are still one of the most important and most widespread human diseases.

With regard to AIDS, an estimated 39.5 million people are living with HIV, the retrovirus causing AIDS. Recent data show that even in 2006 there were about 4.3 million new infections with some areas in the world where the infection rates have risen by more than 50% since 2004. Further, in 2006, about 2.9 million people died of AIDS-related illnesses according to the AIDS Epidemic Update 2006, published by the WHO (in December 2006).

The primary goals of antiretroviral therapy applied are a reduction of HIV-related morbidity and mortality, an improvement of quality of life, a restoration and preservation of immunologic function, and maximal and durable suppression of the viral load. Today antiretroviral therapy, more precisely, treatment regimens against HIV primarily rely on virus enzyme inhibitors and molecules that inhibit virus-cell fusion.

In this regard there are currently four classes of anti-HIV medicines available that are used in the treatment of AIDS. These drug classes target specific steps in the HIV replication process.

Fusion inhibitors (FI) are the first class of active agents, which work outside of host cells in order to prevent HIV from fusing with, entering and infecting these cells. A related approach is to prevent binding of HIV to the target cell via the CD4 receptors and co-receptors called CCR5 or CXCR4 on the surface of the target cells.

The three other classes of active agents work inside the cell. The so-called nucleoside reverse transcriptase inhibitors (NRTI), non-nucleoside reverse transcriptase inhibitors (NNRTI) and protease inhibitors (PI) are used to prevent the replication of the virus inside host cells after they have been infected with HIV.

Examples of NRTIs and NNRTIs preventing HIV from making a copy of its genetic information (thus producing the so-called proviral DNA) are 3TC (lamivudine, Epivir), abacavir (Ziagen), AZT (zidovudine, Retrovir), d4T (stavudine, Zerit), ddC (zalcitabine, Hivid), ddI (didanosine, Videx/VidexEC), FTC (emtricitabine, Emtriva), Efavirenz (Sustiva) and nevirapine (Viramune).

The PIs target the HIV enzyme protease involved in virus assembly. Examples for these active agents are Amprenavir (Agenerase), atazanavir (Reyataz), fosamprenavir (Telzir), indinavir (Crixivan), lopinavir, nelfinavir (Viracept), ritonavir (Norvir) and saquinavir (Invirase/Fortovase).

One type of combination therapy currently used involving the use of more than one active agent is the Highly Active Antiretroviral Therapy (HAART) targeting the viral reverse transcriptase, protease and fusion (GULICK et al., 1997; LALEZARI et al., 2003). The application of this therapy has resulted in transforming HIV-1 infection into a chronic illness that has curtailed the morbidity of infected individuals.

One drawback, however, of all of current treatment strategies is that they only suppress the viral life cycle without eradicating the infection. The major obstacle in such therapies appears to be the establishment of long-lived reservoirs of HIV-1, particularly in latently infected resting $CD4^+$ T cells (CHUN et al., 1998; FINZI et al., 1997), requiring life-long HAART.

Unfortunately, in a growing number of patients long-term HAART is accompanied by significant adverse side effects including mitochondrial toxicity, lipodystrophy, diabetes mellitus and osteoporosis (DYBUL et al., 2002). Substantial drug toxicities often result in inadequate adherence, resulting in the suboptimal inhibition of virus replication. As a consequence, new strains of HIV-1 are emerging that are resistant to suppressive treatments (LITTLE et al., 2002). In view of the increasing number of resistant HIV strains new active agents are necessary and are currently under development. In addition, further viral targets and novel inhibition strategies are being tested for improved control of HIV-1 (DONZELLA, 1998; CHIU et al., 2005; HAZUDA et al., 2004; HAUBER et al., 2005).

An alternative approach discussed in the art is to target the provirus inserted into the genome of the host cell. Excision of the proviral DNA from the host's genome for example would prevent further HIV replication and differs from current methodologies in that it has the potential to eradicate even dormant virus present in the genome of the host.

One class of proteins that were considered for use in this alternative approach are site-specific recombinases (FLOWERS et al., 1997). Site-specific recombinases mediate a multitude of functions in nature from gene rearrangement to genome segregation, such as for example excision, inversion, or integration of defined DNA units (reviewed in STARK et al., 1992).

One of the simplest and best understood recombinases is the Cre recombinase from bacteriophage P1 that resolves genome dimers into monomers by recombination between two identical double-stranded DNA sites of a particular sequence (HOESS & ABREMSKI, 1985). The Cre recombinase has found widespread use in mouse genetics (NAGY, 2000). Cre is a 38 kDa protein that was named after is function, as it causes recombination (STERNBERG & HAMILTON, 1981). Prerequisite for this recombination is the alignment of two recombination sites recognised by Cre in antiparallel orientation which are then bound by four identical Cre subunits that join to form a ring in which each subunit contacts two adjacent subunits and one half site of one recombination site (HOESS & ABREMSKI, 1985). The recombination site recognised by Cre is a 34-bp doublestranded DNA sequence known as loxP (from locus of crossing over (x), P1; STERNBERG & HAMILTON, 1981), which is palindromic with the exception of its eight innermost base pairs (referred to as the spacer), which impart directionality to the site.

Some site-specific recombination systems, including the Cre/loxP-system function without accessory proteins or cofactors and function under a wide variety of cellular conditions. However, since the site-specific recombinases function through specific interactions of the recombinase enzyme subunits with their cognate DNA target sequences, the use of these enzymes is restricted by the requirement that the targeted DNA regions must contain appropriately positioned target sites (LEWANDOSKI, 2001). To date, no wild-type recombinase has been identified that recognises native retroviral sequences as their DNA target sequences.

Extensive mutational and structural analyses of site-specific recombinases have been carried out in recent years to alter their properties and to achieve a better understanding of the intricate mechanisms of these enzymes (for a review see VAN DUYNE, 2001; and COATES et al., 2005). A lot of studies focussed on the Cre recombinase to explore its evolvability. Several studies demonstrated that Cre target specificity could be altered when few nucleotides in its loxP recognition site were changed (BUCHHOLZ & STEWART, 2001; SANTORO & SCHULTZ, 2002; RUFER & SAUER, 2002). Further studies addresses the engineering of mutated loxP target sites containing sequences from the LTR of HIV-1 to develop possible target sites for the use of Cre as antiviral strategy (LEE & PARK, 1998; LEE et al., 2000). To date, however, it has not been possible to generate a recombinase that recognises native asymmetric HIV sequences as their DNA target sequences.

The method of directed evolution is a powerful method to select enzymes with altered specificities (reviewed in Yuan et al., 2005; and JOHANNES & ZHAO, 2006). In the beginning this method was used to isolate improved enzymes on the basis of RNA by selecting RNA molecules with altered substrate sites. The use of PCR-based method allows the screening of very large libraries and the recovery of successful coding regions from a pool of candidates. In the directed evolution of proteins, by contrast, the screening for and the recovery of improved mutants, which are identified by alterations in the properties of the protein, requires a method for retrieving the nucleic acid sequence encoding the protein. The link between the protein and its coding sequence has often been maintained by compartmentalisation. Consequently, library screening in directed protein evolution has been limited to "one-by-one" approaches that maintain the compartments, and the advantages associated with screening pools of candidates have not been available.

This limitation has been overcome by the development of methods that allow the crosslinking of proteins to their respective messenger RNAs (mRNAs) using mRNA-protein fusions and ribosome display. Functional screens for improved protein properties were thus coupled to direct retrieval of corresponding coding molecules, and large pools have been screened in vitro (see for example BUCHHOLZ et al., 1998). A further improvement of directed protein evolution was achieved by the so-called substrate-linked protein evolution (SLiPE; BUCHHOLZ & STEWART, 2001), wherein the substrate of the recombinase was placed on the same DNA molecule as the protein coding region. In this manner, when the recombinase was expressed within a compartment, its action altered the DNA substrate next to its own coding region. Consequently, a library could be screened as a pool by PCR to amplify only candidate coding regions that were next to an altered substrate. This allows the screening of large libraries conveniently for rapid retrieval of successful coding regions. This method was applied for altering the DNA specificity of Cre recombinase and adapting it to a new recognition target site (BUCHHOLZ & STEWART, 2001).

However, a decisive drawback of the use of any recombinase for the excision of retroviral DNA is the need of the recombinase for symmetric target sites, which are typically not found at least twice in the proviral DNA to allow the use of present recombinases.

In view of the potential of site-specific recombinases and the need of finding an AIDS therapy eradicating HIV-1 provirus from the genome of host cell, the problem underlying the present invention thus resides in providing a method for preparing a tailored recombinase, which tailored recombinase recombines asymmetric target sites within the LTR of proviral DNA of a retrovirus inserted into the genome of a host cell thus excising the provirus from the genome of the host cell.

SUMMARY OF THE INVENTION

According to a first aspect of the present invention a method for preparing an expression vector encoding a tailored recombinase is provided, which tailored recombinase recombines asymmetric target sites within the LTR of proviral DNA inserted into the genome of a host cell comprising the steps of (a) determining the sequence of the LTR of the proviral DNA, identifying therein sequences with homology of at least 30% to the left half-site and the right half-site sequences of known target sites of recombinases, wherein the homologous sequences are separated by a spacer of 5-12 nucleotides, and wherein the homologous LTR sequences with highest homology to a known target site represent the asymmetric target sequence;

(b) preparing two synthetic sequences, wherein the first synthetic sequence corresponds to the sequence of the asymmetric target sequence of step (a) homologous to the left half-site of said known target site plus the spacer sequence and is referred to as "half-site sequence 1", and wherein the second synthetic sequence corresponds to the spacer sequence plus the sequence of the asymmetric target sequence of step (a) homologous to the right half-site and is referred to as "half-site sequence 2";

(c) determining the nucleotides within the synthetic sequences of step (b) deviating from the corresponding homologous left half-site and right half-site sequences of the known homologous target site of step (a);

(d) generating a first subset of two target sequences on the basis of the synthetic sequences of step (b), wherein the first target sequence in the first subset comprises an inverted repeat consisting of half-site sequence 1 of step (a) and half-site sequence 1' separated by the spacer sequence, and wherein the second target sequence in the first subset comprises an inverted repeat consisting of half-site sequence 2' and half-site sequence 2 of step (b) separated by the spacer sequence, wherein half-site sequences 1' and 2' represent inverted repeats of the respective half-site sequences 1 and 2 of step (b);

(e) generating a second subset of target sequences on the basis of the target sequences in the first subset of step (d), wherein each of the half-site sequences together with the respective spacer sequence of the target sequences in the first subset of step (d) is used to generate an independent target sequence of the second subset by forming an inverted repeat on the basis of the selected half site sequence, such that the spacer sequence separates both sequences forming the inverted repeat, wherein the sequences of both half-site sequences originating from one of the target sequences in the first subset of step (d) are altered during their synthesis and prior to using same for generating the inverted repeat yielding the complete target sequence such that in the left half-site sequence a portion of the nucleotides deviating from the corresponding homologous half-site sequence of the known target site of step (a) is replaced by the native nucleotides found in the known target site and in the right half-site sequence the rest of the nucleotides deviating from the corresponding homologous left half-site is replaced by the native nucleotides found in the known target site, such that in both half-site sequences originating from one target sequences of the first subset of step (d) taken together all deviating nucleotides can be found, whereas none of said half-site sequences alone comprises all deviating nucleotides;

(f) generating further subsets of target sequences starting from the target sequences in the second subset obtained in step (e) by stepwise repeating the process of step (e) each time generating a new subset of target sequences, until the half-site sequences forming the inverted repeats within each generated target sequences contain one, two or three nucleotides deviating from the corresponding homologous half-site sequence of the known target site;

(g) applying molecular directed evolution on the recombinase recognising the known homologous target site chosen in step (a) using the target sequences of the final subset obtained in step (f) containing one, two or three nucleotides deviating from the corresponding homologous half-site sequence of said known homologous target-site as a substrate;

(h) shuffling the recombinase libraries evolved in step (g);

(i) applying molecular directed evolution on the shuffled library obtained in step (h) using the target sequences of the next higher subset according to step (f);

(j) repeating steps (h) and (i) until at least one recombinase is achieved by molecular directed evolution that is active on the asymmetric target sequence within the LTR of the retroviral DNA of step (a);

(k) isolating the nucleic acid of the least one recombinase obtained in step (j) from the library; and (l) cloning the nucleic acid obtained in step (k) into a suitable expression vector.

In a preferred embodiment the recombinase molecular directed evolution is applied to in steps (g) and (i) is derived from the family of serine integrases or from the family of tyrosine integrases, and is preferably a modified Cre recombinase from phage P1, a modified FLP recombinase from yeast or a modified Dre recombinase from phage D6. Preferably the molecular directed evolution is substrate-linked protein evolution (SLiPE). The expression vector encoding the tailored recombinase is preferably a retroviral vector, a lentiviral vector, a spumavirus vector or a adenoviral vector.

A second aspect of the present invention is directed to the medical use of an expression vector encoding the tailored recombinase or an adult stem cell comprising said expression vector for the preparation of pharmaceutical composition for the reduction of the viral load in a subject infected by a retrovirus. The pharmaceutical composition can be administered to a subject to treat infection by a wide range of retroviruses, such as for example HIV. The pharmaceutical composition of the present invention is preferably used for concomitant administration with other active agents of the highly active antiretroviral therapy (HAART) or for administration concomitant or subsequent to global immune activation therapy or specific activation of provirus gene expression.

According to a third aspect of the present invention an in vitro-method of optimising the treatment of a retroviral infection of a subject is provided, wherein the method comprises the steps of (a) determining the nucleic acid sequence of retroviral DNA present in a blood sample of a patient;

(b) scanning the LTR sequence of the sequence of step (a) for known recombination sequences for which specifically tailored recombinases have already been prepared;

(c) in case at least one of said known recombination sequence exists, then a compound selected from the group consisting of an expression vector comprising the nucleic acid of the tailored recombinase specifically recognising said known recombination sequence, said tailored recombinase, a fusion protein comprising the amino acid sequence of said tailored recombinase or an adult stem cell comprising said expression vector is prepared as a pharmaceutical composition for the reduction of the viral load in the subject; otherwise sequences with homology of at least 30% to the left half-site and the right half-site sequences of known target sites of a recombinase, wherein the homologous sequences are separated by a spacer of 5-12 nucleotides, are identified and termed "asymmetric target sequence";

(d) performing steps (b) to (l) of the aforementioned method for preparing an expression vector encoding a tailored recombinase specifically recombining the asymmetric target sequence identified within the LTR of proviral DNA; and (e) preparing the expression vector obtained in step (d), a protein or a fusion protein expressed from said expression vector or a stem cell transfected or infected with said expression vector as a pharmaceutical composition for the reduction of the viral load in the subject.

In a preferred embodiment the directed molecular evolution applied in step (d) is applied on a tailored recombinase already recognising a target site different from that of wild-type recombinases.

In another preferred embodiment the tailored recombinase obtained in the above methods is included into a collection of specifically tailored recombinases.

The invention is further directed to a collection of tailored recombinases, each recognising distinct target sites in the genome of a provirus.

DETAILED DESCRIPTION OF THE INVENTION

The present inventors for the first time provide a method using a combinatorial substrate linked protein evolution approach to generate a tailored recombinase recognising asymmetric sequence within the sequence of a provirus integrated into the genome of the host cells.

Directed evolution is a laboratory process used on selected molecules to cause mutations and identify subsequent adaptations to novel properties. Hence, it is a powerful method to select enzymes with altered specificities (YUAN et al., 2005, JOHANNES & ZHAO, 2006). One prerequisite of directed evolution is a starting enzyme that has residual activity to allow the evolution strategy to be successful (BLOOM et al., 2005). An enzyme that has no activity on a substrate is unlikely to produce variants that now act on the distant target.

The method of the present invention may also be applied to tailor DNA-modifying proteins in general. However, recombinases are preferred. The term "DNA-modifying protein" is meant to include any protein whose activity causes a change in the sequence or structure of nucleic acid. Examples of DNA-modifying proteins suitable for being tailored by the method of the present invention include proteins involved in homologous recombination, exonucleases, DNA methylases, DNA ligases, restriction endonucleases, topoisomerases, transposases and resolvases.

Although the potential of tailored recombinases obtained by directed evolution has been widely recognized (see e.g. Collins et al., 2003), no method, however, has been successful thus far in altering the properties of a recombinase to recombine a naturally occurring retroviral sequence. FLOWERS et al. (1997) have shown that Cre can reduce the viral load in cells when the virus contains wild-type loxP sites. It was further demonstrated by LEE et al. (2000) that Cre can recombine a spacer sequence chosen from the HIV-1 genome. A pivotal problem in these approaches is that typically the HIV-1 LTRs do not carry symmetric target sites that are recognized by naturally occurring recombinases such as for example the Cre recombinase recognizing a symmetric 13 bp inverted repeat with an 8 bp spacer. This limitation has been addressed by SARAF-LEVY et al. (2006) who developed heterospecific recombinases, each binding to one half-side of a target sequence that were different in sequence. The authors showed that in such a scenario the two different recombinases can together recombine an asymmetric target site. However, this approach has the main disadvantage that two different recombinases would have to be present in the target cell. Taken together, none of the approaches developed to date in the prior art has been able to deliver a single recombinase that can recombine a sequence naturally occurring in a retroviral genome.

The present inventors were the first to realise that recombinases could be tailored to recognise asymmetric target sites different from their native symmetric target sites by splitting up the substrate into a number of new subsets with smaller differences from the original target and stepwise tailoring recombinases to recognise these subsets (see FIG. 1). Further, a combinatorial approach then allows selection of functional molecules recognising the asymmetric target site within a given sequence. Thus, using a new approach of traversing through substrate intermediates during directed molecular evolution the inventors are able to produce enzymes with remote novel asymmetric target specificities.

The method of the present invention for preparing an expression vector encoding a tailored recombinase, which tailored recombinase recombines asymmetric target sites within the LTR of proviral DNA inserted into the genome of a host cell, yields expression vectors encoding tailored recombinases that recombine asymmetric targets sites different from the target site of the wild-type recombinase. The method of the invention comprises the steps of (a) determining the sequence of the LTR of the proviral DNA, identifying therein sequences with homology of at least 30% to the left half-site and the right half-site sequences of known target sites of recombinases, wherein the homologous sequences are separated by a spacer of 5-12 nucleotides, and wherein the homologous LTR sequences with highest homology to a known target site represent the asymmetric target sequence;

(b) preparing two synthetic sequences, wherein the first synthetic sequence corresponds to the sequence of the asymmetric target sequence of step (a) homologous to the left half-site of said known target site plus the spacer sequence and is referred to as "half-site sequence 1", and wherein the second synthetic sequence corresponds to the spacer sequence plus the sequence of the asymmetric target sequence of step (a) homologous to the right half-site and is referred to as "half-site sequence 2";

(c) determining the nucleotides within the synthetic sequences of step (b) deviating from the corresponding homologous left half-site and right half-site sequences of the known homologous target site of step (a);

(d) generating a first subset of two target sequences on the basis of the synthetic sequences of step (b), wherein the first target sequence in the first subset comprises an inverted repeat consisting of half-site sequence 1 of step (a) and half-site sequence 1' separated by the spacer sequence, and wherein the second target sequence in the first subset comprises an inverted repeat consisting of half-site sequence 2' and half-site sequence 2 of step (b) separated by the spacer sequence, wherein half-site sequences 1' and 2' represent inverted repeats of the respective half-site sequences 1 and 2 of step (b);

(e) generating a second subset of target sequences on the basis of the target sequences in the first subset of step (d), wherein each of the half-site sequences together with the respective spacer sequence of the target sequences in the first subset of step (d) is used to generate an independent target sequence of the second subset by forming an inverted repeat on the basis of the selected half-site sequence, such that the spacer sequence separates both sequences forming the inverted repeat, wherein the sequences of both half-site sequences originating from one of the target sequences in the first subset of step (d) are altered during their synthesis and prior to using same for generating the inverted repeat yielding the complete target sequence such that in the left half-site sequence a portion of the nucleotides deviating from the corresponding homologous half-site sequence of the known target site of step (a) is replaced by the native nucleotides found in the known target site and in the right half-site sequence the rest of the nucleotides deviating from the corresponding homologous left half-site is replaced by the native nucleotides found in the known target site, such that in both half-site sequences originating from one target sequences of the first subset of step (d) taken together all deviating nucleotides can be found, whereas none of said half half-site sequences alone comprises all deviating nucleotides;

(f) generating further subsets of target sequences starting from the target sequences in the second subset obtained in step (e) by stepwise repeating the process of step (e) each time generating a new subset of target sequences, until the half-site sequences forming the inverted repeats within each generated target sequences contain one, two or three nucleotides deviating from the corresponding homologous half-site sequence of the known target site;

(g) applying molecular directed evolution on the recombinase recognising the known homologous target site chosen in step (a) using the target sequences of the final subset obtained in step (f) containing one, two or three nucleotides deviating from the corresponding homologous half-site sequence of said known homologous target site as a substrate;

(h) shuffling the recombinase libraries evolved in step (g);

(i) applying molecular directed evolution on the shuffled library obtained in step (h) using the target sequences of the next higher subset according to step (f);

(j) repeating steps (h) and (i) until at least one recombinase is achieved by molecular directed evolution that is active on the asymmetric target sequence within the LTR of the retroviral DNA of step (a);

(k) isolating the nucleic acid of the least one recombinase obtained in step (j) from the library; and (l) cloning the nucleic acid obtained in step (k) into a suitable expression vector.

In step (a) of the method of the present invention the sequence of the LTR of the proviral DNA is determined, such as for example by DNA sequencing using chain-terminating inhibitors (SANGER et al., 1977). However, if the sequence of the LTR of the retroviral DNA inserted into the genome of the host has already been determined, this step can be omitted. It is further possible to use known sequences available from sequence databases. On the basis of the sequence information computer-based analysis of the sequence information is performed to identify therein sequences with homology of at least 30% to the left half-site and the right half-site sequences of known target sites, respectively, of known recombinases that are separated by a suitable spacer of 5-12 nucleotides.

The term "recombinase" as used herein refers to a protein involved in recombination. As such recombinases recognise and bind two specific DNA sequences termed "recombination sites" or "target sites" and mediate recombination between these two target sites. Accordingly, the term "recombinase" is meant to refer to any protein component of any recombinant system that mediates DNA rearrangements in a specific DNA locus. Naturally occurring recombinases recognise symmetric target sites consisting of two identical sequences termed "half-site" of approximately 9-20 bp forming an inverted repeat, wherein the half-site sequences are separated by a spacer sequence of 5-12 bp.

It is to be noted that in the present invention and also in the art the terms "target sequence", "target site" and "recombination site" are used interchangeably.

Contrary to the naturally occurring recombinases recognising symmetric target site, the method of the present invention provides tailored recombinases recognising target sites, which do not consist of palindromic sequences separated by a spacer. Instead, in the asymmetric target sites the sequences do not form a symmetric inverted repeat. Accordingly, a tailored recombinase able to recognise an asymmetrical target site should recognise and recombine target sites consisting of half-sites of varying sequence.

Within an asymmetric target site the sequences referred to as "left half-site" and "right half-site", respectively, are defined by their homology to the left and right half-site of a known target site. The sequence located between the sequences homologous to the left and right half-site of a known target site is referred to as spacer.

However, if sequences are found in the LTR that have only homology to either the left or the right half-site sequence of a known target site, these sequences could nevertheless be used in the practise of the present invention. The size of the target site belonging to the recombinase, whose native target sequence shows homology to sequences within the LTR, is known to the skilled person. For example, if homology is found within the LTR sequence to a target sequence recognised by the Cre recombinase, an asymmetric target site to be recognised by Cre recombinase should consist of 34 nucleotides with two half-site sequences of 13 nucleotides each separated by a spacer of 8 nucleotides. Accordingly, the homologous sequence within the LTR is defined as either the left or the right half-site or the spacer of the asymmetric target site depending on the homology to the sequence of the known target site. Thus, sequences with homology to the left half-site of a known target sequence are defined as left half-site, sequences with homology to the right half-site of a known target sequence are defined as right half-site. Starting from this definition, the other parts of the asymmetric target sites are defined under consideration of the structure of the known target site. Thus, having defined for example a right half-site sequence within the LTR over homology to a loxP site (recognised by Cre recombinase), the other sequences corresponding to the spacer and the left half-site of the asymmetric target sequence can easily be defined. The spacer sequence is for example defined by counting 8 nucleotides upstream of the 5' end of the sequence defined as right half-site sequence, whereas the left half-site sequence is similarly defined by counting 13 nucleotides upstream of the 5' end of the previously defined spacer sequence.

Homology in this context as well as in the whole application means sequence similarity or identity, with identity being preferred. A preferred comparison for homology purposes is to compare at least two sequences using standard techniques known in the art, including, but not limited to, the local homology algorithm of SMITH & WATERMAN (1981), the homology alignment algorithm of NEEDLEMAN & WUNSCH (1970), or the search for similarity method of PEARSON & LIPMAN (1988). For the purposes of the present application sequence homology is preferably determined using the ClustalW computer program available from the European Bioinformatics Institute (EBI), unless otherwise stated.

In view of the requirement of two identical target sites that must be present in the genome of the provirus to allow the recombinase to excise the sequence between these two target sites, sequences of the proviral DNA are scanned in step (a) of the method of the present invention that are present at least twice in the genome. Such sequences are for example the LTR sequences of the proviral DNA. Accordingly, the sequence of the LTR is preferably scanned, since the 5'-LTR and the 3'-LTR of the proviral DNA are identical. An asymmetrical target site present in the 5'-LTR is also present in the 3'-LTR and thus allows for excision of the proviral DNA located between the LTRs.

Out of the sequences identified within the LTR sequence having sufficient homology to known target sites sequences are preferably chosen that have the highest homology to the sequence of the target site of known recombinases. However, it is also possible to select sequences other than those having the highest homology.

It is to be noted that the potential of the method of the present invention even allows tailoring recombinases that recognise asymmetric target sites with less than 30% homology to known target sites. However, to ensure the presence of residual recombination activity for the respective asymmetric target site, it is preferably scanned for sequences having a homology of at least 30% to the left half-site and the right half-site sequences of known target sites of known recombinases. In further preferred embodiments it is scanned for sequences having a homology of 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80%, more preferably 85%, particularly preferably 90% and most preferably 95% to the left half-site and the right half-site sequences of known target sites of known recombinases.

In a preferred embodiment of the present invention the sequence selected with in the LTR has homology to the symmetric loxP target sites recognized by the site specific recombinase Cre. In a more preferred embodiment the sequence of the asymmetric target site is 5'-ACAACATCCTATTACAC-CCTATATGCCAACATGG-3' (SEQ ID NO:36) (FIG. 2A).

In step (b) the chosen sequences within the LTR homologous to a known target site are used for preparing two synthetic sequences. These synthetic sequences are prepared as oligonucleotide sequences by methods known in the art. The sequence of the first synthetic sequence (referred to as "half-site sequence 1") corresponds to the sequence of the selected asymmetric target site within the LTR of the provirus homologous to the left half-site of the known target site and includes the sequence between the sequences representing the left and the right half-site, which is referred to as the spacer. The second synthetic sequence corresponds to the spacer sequence and the sequence of the selected asymmetric target site within the LTR of the provirus homologous to the right half-site of the known target site. This second oligonucleotide sequence is referred to as "half-site sequence 2".

The spacer sequence in both synthetic sequences is preferably identical and corresponds to the sequence of the LTR representing or defined as the spacer sequence of the asymmetric target site. However, in a further embodiment the spacer sequences of both synthetic sequences comprises one or two sequence deviations. The deviations are preferably nucleotide substitutions which retain the original length of the spacer sequence.

In step (c) the nucleotides within "half-site sequence 1" and "half-site sequence 2", respectively, of the first subset of synthetic sequences of step (b) deviating from the sequences of the corresponding homologous left half-site and right half-site sequences of the chosen known target are determined by sequence alignment and sequence comparison. In this context, the sequence of "half-site sequence 1" is compared to the corresponding native half-site, which is preferably the left half-site sequence, whereas the sequence of "half-site sequence 2" is compared to other half-site forming the palindromic native target site, which is preferably the right half-site sequence.

This method must not necessarily performed after step (b) and prior to step (d) of the method of the invention, but can also be performed in a different phase of the method after step (a) and prior to step (e).

In step (d), a first subset of two target sequences is generated using the synthetic sequences of step (b). The target sequences of the first subset are palindromic oligonucleotide sequences having the structure of a symmetric target site. These artificial symmetric target sites are synthesised on the basis of the half-site sequences of step (b) by complementing the missing half-site sequence in each oligonucleotide sequence as inverted repeat, wherein the sequence of. "half-site sequence 1" and "half-site sequence 2", respectively, is used to complement the second half-site sequence at the opposite end of the spacer sequence. Accordingly, the first target sequence in the first subset (referred to as "target sequence 1") comprises an inverted repeat consisting of the "half-site sequence 1" and the inversely repeated "half-site sequence 1'" separated by the spacer sequence, whereas the second target sequence in the first subset (referred to as "target sequence 2") comprises an inverted repeat consisting of the inversely repeated "half-site sequence 2'" and "half-site sequence 2" separated by the spacer sequence (see FIG. 1). In "target sequence 1" the sequence are arranged as follows: 5'-"half-site sequence 1"-spacer-"half-site sequence 1'"-3', in "target sequence 2" the sequence are arranged as follows: 5'-"half-site sequence 2'"-spacer-"half-site sequence 2"-3'.

Similar to what is stated above in step (b), the spacer sequences within each two synthetic target sequences of the first subset are preferably identical and corresponds to the sequence of the LTR representing or defined as the spacer sequence of the asymmetric target site. However, in a further embodiment the spacer sequences may comprise one or two sequence deviations originating from nucleotide substitutions.

Generally, this step represents a first split up of the sequences of the asymmetric target site selected for tailoring a specific recombinase (see FIG. 1). Sequences are generated in this step harbouring symmetric target sites derived from the half-sites of the asymmetric target site selected for tailoring a specific recombinase (see FIG. 1). As a consequence, each mutation (i.e. difference to the target site recognised by the wild-type recombinase) present in one half-site of said asymmetric target site has now been spread up between the symmetric target sequences in the first subset.

In step (e) of the method of the present invention the target sequences of the first subset are used to generate a second subset of target sequences. Each of the half-site sequences and the respective spacer of the target sequences in the first subset of step (d) is independently used to generate a new target sequence (i.e. forming the second subset) by generating an inverted repeat on the basis of the selected half-site sequence, such that the spacer sequence separates both sequences forming the inverted repeat (see FIG. 1). Thus, the left half-site sequence of "target sequence 1" is used to generate a first new symmetric target site, the right half-site sequence of "target sequence 1" is used to generate a second new symmetric target site, the left half-site sequence of "target sequence 2" is used to generate a third new symmetric target site and the right half-site sequence of "target sequence 2" is finally used to generate a fourth new symmetric target site, wherein each time the spacer sequence of the parental target sequence is included into the new symmetric target site (see FIG. 1). However and most important, the half-site sequences derived from each of the target sequences of the first subset are altered during their synthesis and prior to using same for generating the inverted repeat yielding the complete new target sequence (such as for example by performing nucleotide substitutions). In the left half-site sequence of a new target sequence (derived from a target sequence of the first subset) a portion of the nucleotides deviating from the corresponding homologous half-site sequence of the known target sequence of step (a) is replaced by the native nucleotides found in the known target sequence and in the corresponding right half-site sequence (derived from the same target sequence of the first subset) the rest of the nucleotides deviating from the corresponding homologous left half-site is replaced by the native nucleotides found in the known target sequence (see FIG. 1). The nucleotides altered in the left half-site are different from those amended in the right half-site, such that the deviating nucleotides are only present once in both half-site sequences originating from one target sequences of the first subset, either in the target sequence formed on the basis of the left half-site or in the target sequence formed on the basis of the right half-site (see FIG. 1). Further, the sequence alteration is carried out such that each deviating nucleotide is retained once in one of the half-sites. Finally, none of the half half-site sequences alone should comprise all deviating nucleotides.

As already stated above in steps (b) and (d) the spacer sequences within each two synthetic target sequences of a new subset being derived from a synthetic target sequence of a higher subset are preferably identical and corresponds to the sequence of the LTR representing or defined as the spacer sequence of the asymmetric target site. However, in a further embodiment the spacer sequences may comprise one or two sequence deviations originating from nucleotide substitutions.

Using this approach, the number of mutations (i.e. differences to the target site recognised by the wild-type recombinase) in the target sequences representing each subset is smaller than in the starting asymmetric target sequence, but all mutations are still represented in one of the target sequences (see FIG. 1).

The term "deviating nucleotide" as used herein refers to a nucleotide within the asymmetric target sequence identified or defined within the LTR or within a target sequence of a subset generated according to the present invention that deviates (i.e. is different) from the nucleotide present at the same position in the corresponding homologous sequence of the known homologous symmetric target sequence of a known recombinase chosen in step (a) of the method of the present invention. In this context, the terms "deviating nucleotides" and "mutations" are used interchangeably.

An example of the generation of subsets of target sequences is shown more generally in FIG. 1. A more specific example on the basis of an asymmetric sequence within the LTR of a HIV provirus is shown in FIG. 2A.

In step (f) further subsets of target sequences are generated starting from the target sequences of the second subset by stepwise repeating the process of step (e), i.e. splitting up the target sequences into the respective half-site sequences and generating new palindromic structures on the basis of these half-site sequences after altering the sequence of the half-site derived from a target sequence of the second subset, each time generating a new subset of target sequences, until the half-site sequences used for generating the inverted repeats contain one, two or three nucleotides deviating from the corresponding homologous half-site sequence of the known target site.

The present inventors realised that recombinases can be tailored using molecular directed evolution using target sequences as a substrate, if the target sequence used as a substrate differs in not more than 3 nucleotides from the native target sequence. Thus, the generation of subsets of different orders described above serves to reduce the number of deviating nucleotides per target sequence to 3 or less (see FIG. 1). The stepwise reduction of the number of deviating nucleotides finally yields a number of subsets of target sequences of different orders with decreasing numbers of deviating nucleotides until a final subset is created that can be used as a substrate for molecular directed evolution. While creating the different subsets and thereby reducing the number of deviating nucleotides, the differences to the target site recognised by the wild-type recombinase are spread between several target sequences that do not comprise more than 3 of these deviating nucleotides each, while the target sequences of the final order as a whole still represent all deviating nucleotides (see FIG. 1).

Starting from the second subset of target sequences obtained in step (e) a third subset is generated, followed by a fourth, fifth, sixth etc. subset if necessary. However, the generation of the third subset is generally only necessary, if the target sequences of the second subset still contain more than three deviating nucleotides. The same applies to the generation of the next subsets, which are only necessary, if the target sequences of the prior subset still contain more than three deviating nucleotides. It should be noted that in one embodiment subsets of target sequences will be generated until the target sequences of the final subset only comprise one deviating nucleotide. Accordingly, depending on the number of deviating nucleotides in each half-site sequence the number of subsets generated for each half-site sequence of the asymmetric target site may differ. It may for example be necessary to generate only two subsets for the left half-site sequence, whereas three or four subsets must be generated for the right half-site in order spread the deviating nucleotides between several target sequences such that a single target sequence does not comprise more than 3 of these deviating nucleotides.

The principle of generating further subsets of the target sequences for reducing the number of deviating nucleotides to numbers below three is illustrated in FIG. 1.

In step (g) a method of molecular directed evolution is applied on the recombinase recognising the known homologous target site of step (a) using the target sequences of the final subset obtained in step (f) containing one, two or three nucleotides deviating from the corresponding homologous half-site sequence of said known homologous target site as a substrate.

The term "final subset" as used herein refers to the last subset generated in step (f). Depending on the number of deviating nucleotides in the asymmetric target site and number of subsets that had to be generated to reduce the number of deviating nucleotide per target sequence below 3, the "final subset" may correspond to any subset, for example the second, third, fourth or a later subset, and may be different for the half-site sequences of the asymmetric target sequence within the LTR.

Methods of molecular directed evolution, also referred to as laboratory evolution or in vitro-evolution, are known in the art (for a review see YUAN et al., 2005 and references therein; JOHANNES & ZHAO 2006).

In a first step of molecular directed evolution libraries of randomly mutated recombinase sequences are generated by methods known in the art, e.g. by using error prone PCR and DNA shuffling (reviewed in e.g. YUAN et al., 2005), or the methods disclosed in the International Patent application WO 02/44409. The plasmids of each library comprising the mutated recombinase also contain one of the target sequences of the final subset obtained in step (f). After transfection of the generated plasmid library into appropriate cells expression of the recombinase is enabled and the molecular directed evolution is carried out as known by the person skilled in the art.

In a preferred embodiment the molecular directed evolution employed in step (g) of the method of the present invention is substrate-linked protein evolution (SLiPE; BUCHHOLZ & STEWART, 2001; International Patent application WO 02/44409). The substrate-linked protein evolution is carried out as described in detail in the Examples. Briefly, the target sequences obtained in step (f) are cloned into a plasmid (the so-called evolution vector) together with a randomly mutated coding sequence for the recombinase. The random mutation is carried out by error-prone PCR (see BUCHHOLZ & STEWART, 2001). The generated plasmid library is then transfected into E. coli cells to allow expression of the recombinase. By using an inducible promoter to drive the expression of the recombinase it is possible to adjust the expression levels. After overnight incubation, plasmid DNA is isolated from the cells and is digested with NdeI to cut the plasmids that were not recombined and only recombined plasmids are subsequently amplified with primers. The PCR product of the recombined form of the plasmid produces a 1.7 Kb band. The PCR product is digested with BsrGI and XbaI and subcloned back into similarly digested evolution vector for the next evolution cycle.

In step (h) the recombinase libraries evolved in step (g) are combined and shuffled. The technology of DNA shuffling is known in the art (for a reviewed see MINSHULL & STEMMER, 1999; STEMMER, 1994).

The combined and shuffled library is then cloned into a new generation of vectors comprising the target sequences of the next higher subset generated in step (f).

The term "next higher subset" as used herein refers to the subset used to generate a certain subset. For example, the third subset was generated on the basis of the target sequences of the second subset. Thus, starting from the third subset the "next higher subset" will be the second subset. Further, the next higher subset starting from the second subset is the first subset. The same applies to the third, fourth (and so on) subset, and the next higher subset starting from this first subset is the asymmetric target sequence with the LTR sequence.

In step (i) the method of molecular directed evolution is applied on the shuffled library obtained in step (h) using the target sequence of the next higher subset according to step (f). In this step the same method of molecular directed evolution as those applied before in step (g) can be used, but it is also possible to use a different method of molecular directed evolution in this step of the method of the present invention. Examples of different methods of molecular directed evolution were described for example by YUAN et al. (2005).

Preferably the method of substrate-linked protein evolution is also applied on the combined and shuffled libraries.

This step yields recombinases recognising and recombining target sequences harbouring the combination (and thus increasing numbers) of mutations from the different target sequences of the lower subset. The inventors were the first to show that the combination of mutations from the different libraries of a lower subset of target sequences result in synergistic effects and led to the generation of recombinases, which now recombine target sequences of a higher subset, demonstrating that an evolution strategy traversing through intermediates can be used to achieve a desired activity.

In step (j), the steps (h), i.e. combining and shuffling of recombinase libraries, and (i), i.e. the application of molecular directed evolution on the combined and shuffled libraries, are repeated until at least one recombinase is achieved that is active on the asymmetric target sequence present in the LTR of the proviral DNA. For example, in a method wherein the generation of three subsets of target sequences was necessary to generate target sequences with only one, two or three nucleotide deviations, the recombinase libraries evolved for example for the third subset of target sequences are combined and shuffled and molecular directed evolution is applied on this shuffled library using the target sequences of the second subset. The thus evolved recombinase libraries are then combined and shuffled and molecular directed evolution is applied on this library using the target sequences of the first subset. In the next (and final) step the asymmetric target sequence of step (a) within the LTR of the proviral DNA is used to evolve the recombinase library comprising recombinases recognising the target sequences of the first subset by molecular directed evolution to obtain at least one recombinase that is active on the asymmetric target sequence within the LTR of the retroviral DNA.

In this step the method of molecular directed evolution is preferably the method of substrate-linked protein evolution.

In step (k) the nucleic acid of the least one recombinase having activity on the asymmetric target sequence of step (a) within the LTR of the retroviral DNA is isolated from the library. The nucleic acid is isolated from the respective plasmid within the library using appropriate restriction enzymes. Method of restriction endonuclease digestion are known to skilled person. The nucleic acid encoding the recombinase can than be recovered by known methods such as for example gel electrophoresis.

The nucleic acid may be stored (preferably by temperatures below −80° C.) or may optionally be cloned in step (l) into an expression vector for use in further analysis, in protein expression methods of for the administration to a subject for treating AIDS. Suitable expression vectors are defined below.

Preferably, the recombinases finally obtained are tested in mammalian cells to ensure that they function in a mammalian cell environment. Further, to obtain good expression in mammalian cells the recombinases may be optimised for expression in these cells (e.g. codon usage optimisation using methods well known in the art. See for example SHIMSHEK et al., 2002) or signal sequences necessary for directing the protein into the nucleus of the mammalian cell, such as the NLS sequence (MACARA, 2001) may be added to the nucleic acid of the tailored recombinase.

In a preferred embodiment of the present invention the known recombinase whose target sequence is used in step (a) and upon which molecular directed evolution is applied in steps (g) and (i) belongs to the family of serine integrases. Preferred recombinases belonging to the family of serine integrases are selected from the group consisting of phiC31 integrase (COMBES et al., 2002), any component of Gin or Hin recombination systems, Tn3 resolvase (KRASNOW & COZZARELLI, 1983) or any other member of the large serine recombinases, Rag1, Rag2 or any other component of the VDJ recombination system or variants thereof.

In another preferred embodiment said recombinase belongs to the family of tyrosine integrases. Preferred recombinases belonging to the family of tyrosine integrases are selected from the group consisting of Cre from Phage P1 (ABREMSKI et al., 1983, 1984), FLP recombinase from yeast (VOLKERT & BROACH, 1986), Dre from phage D6 (SAUER & MCDERMOTT, 2004), R recombinase from *Zygosaccharomyces rouxii* plasmid pSR1, A recombinase from *Kluveromyces drosophilarium* plasmid pKD1, a recombinase from the *Kluveromyces waltii* plasmid pKW1, TnpI from the *Bacillus* transposon Tn4430, any component of the λ Int recombination system or variants thereof.

Recombinases from the tyrosine integrase family are characterised by having a tyrosine as the active site nucleophile that is utilised for DNA cleavage, whereas recombinases from the serine integrase family use a serine instead of a tyrosine.

The term variant in this context refers to proteins which are derived from the above proteins by deletion, substitution and/or addition of amino acids and which retain some or all of the function inherent in the protein from which they are derived.

In a preferred embodiment, the known recombinase is a chimeric recombinase obtained by for example "family shuffling" as described by CRAMERI et al. (1998). Prerequisite for the employment of family shuffling is a significant homology between the recombinases used for generating the chimeric recombinases. An example for a chimeric recombinase that can be used in the present invention is a chimeric recombinase consisting of sequences of recombinase Cre and of recombinase Dre, respectively.

In a more preferred embodiment the recombinase is the Cre recombinase recognising a symmetric target site of 34 bp known as loxP. The loxP site (and also other recombination sites of wild-type recombinases) is palindromic with two 13 bp repeats separated by the eight innermost base pairs, which represent the so-called spacer, which imparts directionality to the site. Recombination takes place by cleavage within the spacer sequence. Depending on the relative location and orientation of the two participating loxP sites, Cre catalyses DNA integration, excision or rearrangement (HOESS & ABREMSKI, 1985).

Preferably the asymmetric target sequence identified in step (a) is localised in both the 5'-LTR and the 3'-LTR of the provirus to allow excision of the proviral DNA from the genome of the host cell.

The present inventors identified a sequence within the LTR sequence of proviral HIV DNA having 50% homology to the loxP site. This sequence referred to as loxLTR (SEQ ID NO: 1) and belongs to the LTR of the primary HIV-1 strain TZB0003 (BLACKARD et al., 1999) being part of its modulatory U3 region (sequence position-262 to -229; where the site of transcription initiation is +1). The loxltr site is a 34 bp asymmetric sequence that has 50% sequence similarity to the sequence of the loxP site with four mismatches in the left element, six in the right element and a completely different spacer (see FIG. 2A).

Using substrate linked directed evolution and the loxLTR sequence as a substrate, the present inventors have been able to produce a tailored recombinase that recombines this asymmetric DNA target sequence present in an HIV-1 long terminal repeat. This is the first time that a single Cre related site specific recombinase was generated that recombines an asymmetric target site. Contrary to the recombinases known in the art, the recombinase of the present invention recognises target sites that were asymmetric and very remote from the original target site of native Cre recombinase. The development of tailored recombinases that specifically targets asymmetric sequences within an HIV-1 LTR allows the excision of the respective provirus from its chromosomal integration site as was shown by the inventors.

However, it is obvious for the person skilled in the art that other tailored site specific recombinases can be generated that recombine divergent target sites found in the genome of retroviral provirus inserted into the genome of the host cell. Candidate sequences can for example be determined on the basis of homology to the present loxLTR sequence. Examples of such LTR sequences derived from the LTR of other HIV strains with homology to the loxLTR sequence are shown in FIG. 6.

The proviral DNA inserted into the genome of a host cell is preferably the DNA of a retrovirus. Retroviruses comprise a large and diverse family of enveloped RNA viruses. The hallmark feature of the family is its replicative strategy which includes as essential steps the reverse transcription of the viral RNA into linear double-stranded DNA and the subsequent integration of this DNA (proviral DNA) into the genome of the host cell. Retroviruses are subdivided into seven groups, defined by evolutionary relatedness. Five of these groups (alpha-, beta-, delta-, epsilon-, and gamma-retrovirus) represent retroviruses with oncogenic potential, and the other two groups are the lentiviruses and the spumaviruses. The human pathogenic human T cell leukemia viruses type I and type II (HTLV-I and HTLV-II) belong to the delta-retrovirus group, while the AIDS viruses human immunodeficiency virus type 1 and type 2 (HIV-1 and HIV-2) belong to the lentivirus group (for a review see the standard textbook "Retroviruses" of COFFIN J M, HUGHES S H, VARMUS H E (Eds.) 1997, Cold Spring Harbor Laboratory Press, New York).

In a preferred embodiment the proviral DNA inserted into the genome of a host cell is the DNA of a retrovirus selected from the group consisting of Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV).

In a further preferred embodiment, the retrovirus is a lentivirus selected from the group consisting of Human immunodeficiency virus Type 1 (HIV-1), Human immunodeficiency virus Type (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV).

In a more preferred embodiment the asymmetric target sequence identified in step (a) of the method of the present invention is localised in both the 5'-LTR and the 3'-LTR of a HIV provirus. Preferably, said asymmetric target sequence localised in both the 5'-LTR and the 3'-LTR of a HIV provirus has the sequence set forth as SEQ ID NO: 1. This sequence is referred to as loxltr.

In a preferred embodiment the method of molecular directed evolution applied in the method of the present invention is the method of substrate-linked protein evolution (SLiPE; BUCHHOLZ & STEWART, 2001; see also WO 02/44409).

In the method of the present invention the nucleic acid encoding the at least one tailored recombinase that is active on the asymmetric target sequence within the LTR of the retroviral DNA is cloned into an expression vector. Expression vectors are genetic constructs for expressing the proteins encoded by the nucleic acids within the vector. Such expression vectors may be either self-replicating extrachromosomal vectors or vectors which integrate into a host genome. Generally, these expression vectors include transcriptional and translational regulatory nucleic acid operably linked to the nucleic acid encoding the tailored recombinase of the present invention.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilise promoters, polyadenylation signals, and enhancers.

Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the tailored recombinase. Numerous types of appropriate expression vectors, and suitable regulatory sequences are known in the art for a variety of host cells.

The expression vector used in the present invention may be a retroviral vector, a lentiviral vector, a spumavirus vector or an adenoviral vector. However, in a preferred embodiment the expression vector is a lentiviral vector selected from the group consisting of HIV-1-, SIV-, FIV- or EIAV-derived lentiviral vectors. Lentiviral vectors are for example described by SCHAMBACH et al. (2006).

In preferred embodiments of the present invention the expression vector comprises a cellular, bacterial, a viral or a hybrid promoter.

In general, for the purpose of the present invention, the promoter may be a constitutive or an inducible promoter. Further, the promoters may be either a naturally occurring promoter, such as a bacterial, cellular or a viral promoter, or a hybrid promoter. Hybrid promoters, which combine elements of more than one promoter, are known in the art, and are useful in the present invention. Further, the promoter used in the present invention may also be a derivative of a naturally occurring promoter. A "derivative" of a naturally occurring promoter as used herein may be a combination of cis-active elements obtained from promoters or sequences of different origin or, alternatively, may be obtained by deletion or mutation of cisactive elements within a specific naturally occurring promoter (EDELMAN et al., 2000; ALPER et al., 2006; HARTENBACH & FUSSENEGGER, 2006).

In a more preferred embodiment of the present invention, the constitutive promoter or derivative thereof is selected or derived from the group consisting of promoters of cytomegalovirus, Rous sarcoma virus, murine leukemia virus-related retroviruses, phosphoglycerokinase gene, murine spleen focus-forming virus or human elongation factor 1 alpha.

In a further more preferred embodiment of the present invention, the inducible promoter or derivative thereof is selected or derived from the group consisting of the LTR or derivatives thereof derived from lentiviruses, spumaviruses and deltaretroviruses.

In this context the term "LTR" refers to both the 5' and the 3' long terminal repeats of provirus having promoter function (for a review see the standard textbook "Retroviruses" (COFFIN J M, HUGHES S H, VARMUS H E (Eds.) 1997, Cold Spring Harbor Laboratory Press, New York)).

Preferably the inducible promoter or derivative thereof is selected or derived from the LTR or derivatives thereof derived from HIV-1, HIV-2, MVV, EIAV, CAEV, SIV, FIV, BIV, HTLV-I and HTLV-II.

The present invention further provides a method for preparing a tailored recombinase, wherein said method comprises the aforementioned method for preparing an expression vector encoding a tailored recombinase and the further step of expressing the tailored recombinase or a fusion polypeptide comprising the amino acid sequence of said tailored recombinase from the nucleic acid encoding the recombinase inserted into the expression vector obtained in the aforementioned method for preparing an expression vector encoding a tailored recombinase in a suitable host cell.

Expression of the nucleic acid encoding the tailored recombinase cloned into an expression vector according to step (l) of the method for preparing en expression vector encoding a tailored recombinase can be carried using for example bacterial, insect or mammalian expression systems. However, other expression systems known in the art may also be employed. Methods of introducing exogenous nucleic acid into mammalian, insect or bacterial hosts, as well as other hosts, are also well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Fusion proteins are prepared by methods well known in the art. For example, the expression vector the nucleic acid encoding the tailored recombinase is cloned into already comprises a nucleic sequence encoding a second polypeptide or protein. By cloning the nucleic acid encoding the tailored recombinase in frame with the sequence of the second polypeptide or protein, both sequences will be expressed as fusion protein.

The host cells used for expressing the tailored recombinase from the expression vector are preferably host cells including prokaryotic cells, such as for example bacterial cells or yeast cells, or eukaryotic cells, such as for example insect cells or mammalian cells.

The present invention further provides a method for preparing a transformed adult stem cell, wherein said method comprises the aforementioned method for preparing an expression vector encoding a tailored recombinase and the further step of introducing the expression vector obtained in the aforementioned method for preparing en expression vector encoding a tailored recombinase in vitro into a suitable adult stem cell.

In a further aspect the present invention is directed to the nucleic acid as obtainable from the aforementioned method of the present invention.

A "nucleic acid" as used herein is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

In its broadest aspect the nucleic acid obtained by the method of the present invention is a nucleic acid encoding a tailored recombinase, wherein the tailored recombinase recombines asymmetric target sequences within the DNA of a provirus inserted into the genome of a host cell leading to excision of the provirus from the genome of the host cell, wherein the asymmetric target sites are different from the target sites of the wild-type recombinase.

In an embodiment the nucleic acid obtained by the method of the present invention has the nucleic acid sequence set forth as SEQ ID NO: 2 and recognises and recombines the loxltr sequence set forth as SEQ ID NO: 1.

Also included within the definition of the nucleic acid are variants of the nucleic acid sequence obtained by the method of the present invention that have at least 50% similarity, preferred at least 60% similarity, more preferred at least 70% similarity, even more preferred at least 80% similarity and most preferred at least 90% similarity to the nucleic acid sequence set forth as. SEQ ID NO: 2. In some embodiments the similarity will be as high as 91, 92, 93, 94, 95, 96, 97, 98 or 99%.

In a further aspect the present invention is also directed to the expression vector as obtainable from the aforementioned method of the present invention.

A further aspect of the invention is the tailored recombinase protein as obtainable from the aforementioned method of the present invention.

The term "protein" as used herein includes proteins, polypeptides, and peptides. As will be appreciated by those in the art, the nucleic acid sequences of the invention can be used to generate protein sequences.

In a preferred embodiment the tailored recombinase protein has the amino acid sequence set forth as SEQ ID NO: 3. This recombinase was termed Tre for LTR recombinase.

Also included within the embodiment of tailored recombinase proteins are amino acid variants of the amino acid sequence set forth as SEQ ID NO: 3. Preferably, the variants will have a sequence similarity of at least 70%, more preferably a sequence similarity of at least 80% similarity, and most preferably a sequence similarity of at least 90% to the sequence set forth as SEQ ID NO: 3. In some embodiments the similarity will be as high as 91, 92, 93, 94, 95, 96, 97, 98 or 99%. As for nucleic acids, similarity in this context means sequence homology or identity, with identity being preferred. This similarity will be determined using Standard techniques known in the art as are outlined above for the nucleic acid homologies.

In a further preferred embodiment the tailored recombinase protein may also be prepared as a fusion polypeptide, using techniques well known in the art. In a preferred embodiment the tailored recombinase protein is linked to a second polypeptide. Preferably the fusion polypeptide is obtained from the aforementioned method of the present invention, wherein the tailored recombinase is linked to a second polypeptide.

Preferably, the tailored recombinase protein is prepared as a fusion polypeptide to increase expression. In a further preferred embodiment the tailored recombinase protein is made as a fusion polypeptide to allow introduction of the polypeptide into living cells. Typically, purified proteins cannot enter into cells, because they are not able to pass the cell membrane due to their size. However, fusion of specific peptides sequences to proteins can result in the uptake of these fusion proteins into cells. In the cell the protein can then perform its function. Site specific recombinases, including Cre recombinase, have been successfully delivered into cells with this approach (PEITZ et al., 2002). Cell-permeant recombinase have further been described by NOLDEN et al. (2006) and LIN et al. (2004). Hence, this strategy may be used to deliver the tailored recombinases into cells to remove the provirus from infected cells.

Thus, the second polypeptide in the fusion polypeptide may comprise a signal peptide. The signal peptide may be a protein transduction domain such as the TAT peptide or a peptide from the third helix of the Antennapedia homeodomain (DEROSSI et al., 1994, 1996; VIVES et al., 1997; VIVES, 2003; RICHARD et al., 2005) or the NLS (nucleus localisation sequence) for delivering the fusion polypeptide into the nucleus of an eukaryotic cell (MACARA, 2001).

A further aspect of the present invention is directed to the adult stem cell as obtainable from the aforementioned method for preparing a transformed adult stem cell of the present invention. The stem cells are preferably infected or transfected with the expression vector according to the invention.

In a preferred embodiment the adult stem cell is a stem cell from the hematopoietic lineage expressing the tailored recombinase, the aforementioned fusion polypeptide or comprising the aforementioned expression vector.

Hematopoietic stem cells (HSC) are bone marrow-derived $CD34^{30}$ cells, which can be purified from G-CSF-mobilised peripheral blood of donors (e.g. HIV-infected patients) by routine leukapheresis (SCHERR & EDER, 2002). The in vitro genetically modified cells will then be reinfused into the patients.

In the state of the art, the term "stem cells" designates cells which (a) have the capability of self-renewal and (b) the capability to form at least one and often a number of specialised cell types due to their asymmetrical division capability (DONOVAN & GEARHART, 2001). Adult stem cells can be isolated from different tissues of adult, i.e. from differentiated individuals. Such stem cells are referred to in the state of the art as "multipotent adult stem cells". The essential difference between embryonic pluripotent stem cells and adult multipotent stem cells lies in the number of differentiated tissues, which can be obtained from the respective cells.

In a further preferred embodiment the present invention is directed to $CD4^+$ primary cells (blood cells) of HIV-infected patients.

In a further step of the method of the present invention the expression vector comprising the nucleic acid sequence encoding a tailored recombinase, the recombinase protein, the fusion protein or the adult stem cell obtained by the methods of the present invention are prepared as a pharmaceutical composition for the reduction of the viral load in a subject infected by a retrovirus.

A further subject of the invention is the pharmaceutical composition obtained by the aforementioned method. The pharmaceutical composition is preferably present in the form of a solution suitable for intravenous application (infusion).

The pharmaceutical preparation may further comprise one or more pharmaceutically acceptable carrier(s), excipient(s) and/or adjuvant(s). Carriers, excipients and adjuvants suitable for use in a pharmaceutical composition are known in the art.

The pharmaceutical composition of the present invention reduces the virus load in a subject infected by a retrovirus below 5.000 genome equivalents/ml plasma, preferably below 500 genome equivalents/ml plasma and more preferably below 50 genome equivalents/ml plasma when administered to the subject.

Thus, the pharmaceutical composition of the present invention comprising an expression vector encoding a tailored recombinase (or the tailored recombinase as a protein or fusion polypeptide or a stem cell comprising the expression vector) is capable of reducing the virus load in a subject infected with a retrovirus by eradicating the genetic reservoir of retroviruses within hosts cells, thereby preventing further life cycles of the virus.

The term "virus load" as used herein refers to the HIV RNA equivalents (i.e. genomes) that are associated with 1 ml of the patient's plasma (DYBUL et al., 2002). Thus, the virus load is determined by measuring the content of viral DNA in s sample obtained from the patient. Currently, there are three main types of viral load assays available:

1) HIV RNA reverse transcription-polymerase chain reaction (RT-PCR): Amplicor™ HIV-1 Monitor Test; Roche Diagnostics
2) Branched chain DNA (bDNA): Versant™ HIV RNA Assay; Bayer Diagnostics; and
3) Nucleic acid sequence-based amplification (NASBA): NucliSens™ Assay; bioMerieux.

In a preferred embodiment the pharmaceutical composition of the present invention is capable of reducing the virus load in a subject infected by a retrovirus below 5.000 genome equivalents/ml plasma, preferably below 500 genome equivalents/ml plasma and more preferably below 50 genome equivalents/ml plasma. Patient with a virus load of below 5000 genome equivalents/ml plasma are considered to be relatively well adjusted to the medicinal treatment. However, the goal in current AIDS therapy is a reduction of the viral load below the detection limit of the virus load assays, which is currently below about 50 genome equivalents/ml plasma.

In this context, the inventors were the first to show that a tailored recombinase can be used to excise the full-size proviral DNA from the genome of a mammalian host cell without negatively affecting cell viability (see FIG. 9). After treatment of infected cells with a tailored recombinase according to the present invention (1) retroviral DNA within the host's genome and (2) virus particle budding from infected cells were not longer detectable, showing that the viral reservoir in resting cells was destroyed.

The pharmaceutical composition preferably reduces the viral, load of retroviruses selected from the group consisting of the Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV).

In yet a further preferred embodiment retrovirus to be treated with the pharmaceutical of the present invention is a lentivirus. Said lentivirus is preferably selected from the group consisting of Human immunodeficiency virus Type 1 (HIV-1), Human immunodeficiency virus Type 2 (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV).

However, it is obvious to the person skilled in the art, that the present invention is also applicable to retroviral infections by other retroviruses than those mentioned above.

Further, the subject infected by a retrovirus the pharmaceutical composition is administered to is selected from the group consisting of humans, primates, monkeys, cattle, horses, goats, sheep and domestic cats. However, the subject is preferably a human being.

In a preferred embodiment the pharmaceutical composition is for concomitant administration with other active agents of the highly active antiretroviral therapy (HAART).

The highly active antiretroviral therapy HAART is a combination therapy targeting the viral reverse transcriptase, protease and fusion (GULICK et al., 1997; LALEZARI et al., 2003).

In another preferred embodiment the pharmaceutical composition is for administration concomitant or subsequent to global immune activation therapy or specific activation of provirus gene expression.

The premise of immune activation therapy is based on the hypothesis that deliberate activation of latently HIV-infected cells may accelerate eradication of persistent viral reservoirs. Eradication would occur via immune clearance by programmed death of those cells actively expressing HIV-1 (proapoptotic) products (KULKOSKY & BRAY, 2006). Global immune activation (activation of immune cells, including resting cells) is usually achieved by, for example, administration of immunotoxins, cytokines (e.g. IL-2), or T cell activating antibodies (e.g. OKT3).

In view of the fact, that immune activation conducted to deliberately activate HAART-resistant latent reservoirs did unfortunately fail to permanently eliminate HIV-1 and viral rebound (for reviews see KULKOSKY & BRAY 2006; MARCELLO, 2006; SHEHU-XHILAGA et al., 2005) due to the fact that global T cell activation apparently also induces viral replication and increases the number of potential HIV-1 target cells beyond the level that can be contained by HAART (FRASER et al., 2000) further specific treatments are necessary to treat HIV. One approach is the activation of transcription of otherwise quiescent viral genomes. Specific activation of latent provirus gene expression may be achieved by administration of the phorbol ester Prostratin or the human cytokine IL-7, which both appear to reactivate latent HIV-1 in the absence of cellular proliferation (MARCELLO, 2006). Moreover, the selective transcriptional activation of HIV-1 may also be achieved by histonedeacetylase (HDAC1)-inhibitors such as, for example, valproic acid, that eventually induces outgrowth of HIV-1 from resting cells in absence of cellular activation (MARCELLO, 2006; LEHRMAN et al., 2005).

However, global immune activation therapy or specific activation of provirus gene expression or similar therapy strategies greatly benefits from the concurrent removal of proviral DNA, thereby reducing in the patient the pool of infected cells.

In a further aspect the present invention is directed to an in vitro method of optimising the treatment of a retroviral infection of a subject.

This method comprises the steps of
(a) determining the nucleic acid sequence of retroviral DNA present in a blood sample of a patient;
(b) scanning the LTR sequence of the sequence of step (a) for known recombination sequences for which specifically tailored recombinases have already been prepared;
(c) in case at least one of said known recombination sequence exists, then a compound selected from the group consisting of an expression vector comprising the nucleic acid of the tailored recombinase specifically recognising said known recombination sequence, said tailored recombinase, a fusion protein comprising the amino acid sequence of said tailored recombinase or an adult stem cell said expression vector is prepared as a pharmaceutical composition for the reduction of the viral load in the subject; otherwise sequences with homology of at least 30% to the left half-site and the right half-site sequences of known target sites of a recombinase, wherein the homologous sequences are separated by a suitable spacer of 5-12 nucleotides, are identified and termed "asymmetric target sequence";
(d) performing steps (b) to (l) of the aforementioned method for preparing an expression vector for preparing an expression vector encoding a tailored recombinase specifically recombining the asymmetric target sequence identified within the LTR of proviral DNA; and
(e) preparing the expression vector obtained in step (d), a protein or a fusion protein expressed from said expression vector or a stem cell transfected or infected with said expression vector as a pharmaceutical composition for the reduction of the viral load in the subject.

In this method a tailored recombinase is provided for use in the treatment of a patient suffering from a retroviral infection that is specifically tailored to recombine specific target sequences of the retrovirus the patient is infected with. In view of the sequence varieties found within the LTR sequences of various retroviruses a recombinase tailored to recombine a specific asymmetric target sequence of a specific retrovirus will not necessarily recognise target sequences within the proviral DNA of other retroviruses and will thus be less or even not efficient in excising other proviral DNAs than those it was tailored for. However, to address this problem and to provide individually tailored recombinases for treating the retroviral infection of basically each subject, the present inventors provide an in vitro method allowing optimisation of the efficacy of a recombinase to be administered by selecting or tailoring a recombinase that will specifically recognise a target sequence within the individual proviral genome a subject is infected with.

In step (a) of the in vitro method of the invention of optimising the treatment of a retroviral infection the nucleic acid sequence of retroviral DNA present in a blood sample of a patient is determined. In this first step the retrovirus the patient is infected with is preferably determined by DNA sequencing using chain-terminating inhibitors (SANGER et al., 1977) of the genome of the viral particles within the blood sample obtained from the patient. Other means well known to the skilled person providing information on the sequence of the retrovirus may also be used.

In step (b) of the in vitro method the LTR sequence obtained in step (a) is scanned for known recombination sequences for which specifically tailored recombinases have already been prepared. This search is performed by using for example computer-based sequence analysis as described above.

If the LTR of the virus particles found in the blood sample comprise at least one sequence corresponding to a known asymmetric target sequence for which a tailored recombinase already exists, then a compound selected from the group consisting of an expression vector comprising the nucleic acid of the tailored recombinase specifically recognising said known recombination site, said tailored recombinase, a fusion protein comprising the amino acid sequence of said tailored recombinase or an adult stem cell transfected of infected with the expression vector as defined above is prepared as a pharmaceutical composition for the reduction of the viral load in the patient. This allows a fast and individual treatment of the specific retroviral infection with an efficient recombinase.

However, if no such tailored recombinase has been prepared before, in step (c) the LTR sequence of the virus particles found in the blood sample is used for identifying sequences therein with homology of at least 30% to the left half-site and the right half-site sequences of known target sites of a recombinase, wherein the homologous sequences are separated by a spacer of 5-12 nucleotides. As above, such homologous sequences are termed "asymmetric target sequence". The detailed description provided above for step (a) of the method for preparing an expression vector encoding a tailored recombinase also applies here.

In step (d) of the in vitro method, the steps (b) to (l) of the method of preparing an expression vector encoding a tailored recombinase described above are performed for preparing an expression vector encoding a tailored recombinase specifically recombining an asymmetric target sequence identified within the LTR of the retrovirus found in the blood sample. This allows the preparation of a novel recombinase recombining the proviral DNA of the retrovirus the patient is suffering from within a very short time.

The detailed description provided above for steps (b) to (l) of the method for preparing an expression vector encoding a tailored recombinase also applies here.

Finally, in step (e) of the in vitro method the obtained expression vector encoding a recombinase specifically recognising and recombining the proviral DNA of the retrovirus the patient is infected with is prepared as a pharmaceutical composition for the reduction of the viral load in said patient. In this context, in a further embodiment the pharmaceutical composition preferably may comprise the individually tailored recombinase as a protein or a fusion protein expressed from the expression vector or a stem cell transfected or infected with said expression vector. In a more preferred embodiment the pharmaceutical composition comprises an expression vector containing nucleic acids encoding the individually tailored recombinase.

The recombinase to which the method of directed molecular evolution is applied to in the above described the in vitro method is chosen from a wild-type recombinase or an already tailored recombinase. However, the recombinase is preferably a tailored recombinase (recognising a slightly different asymmetric target sequence than those found in the LTR of the present proviral DNA). The choice depends on the homology of the asymmetric target sequences. Although directed molecular evolution may be applied to a recombinase (either wild-type or tailored) recognising a target sequence with low homology to sequence within the LTR of the proviral DNA, this will require additional evolution cycles to obtain a specifically tailored recombinase and will thus be more time-consuming. As it is more likely that an existing tailored recombinases recognises an asymmetric target sequence having close sequence homology to sequences found in the LTR, directed molecular evolution is preferably applied on such tailored recombinases. Fewer differences within the target sequences require less evolution cycles to "change" the specificity of the recombinase (previously tailored to recognise a different target sequence) to the target sequence within the LTR, thus saving time and allowing a faster treatment of the retroviral infection.

In a preferred embodiment of the in vitro method the efficacy of either the already existing tailored recombinase identified in step (c) of the in vitro or the recombinase specifically tailored in step (d) is optionally tested in vitro with regard to excising the proviral DNA of the retrovirus the patient subject is infected with. This testing is performed prior to preparing said recombinases as pharmaceutical composition.

Testing of the efficacy of the recombinases is performed to ensure that the respective recombinase recognises and recombines the specific asymmetric target sequence also in mammalian cells. This testing is preferably performed in mammalian cell such as HeLa cells, PM1 cells, Jurkat T cells, CEM T cells and peripheral blood monocytic cells (PMNCs).

In a further optional step of the in vitro method of optimising the treatment of a retroviral infection of a subject the tailored recombinase finally obtained is included into a collection of specifically tailored recombinases. This step allows the construction of a collection of different tailored recombinases each recognising specific target sequences different from that of the others. The growing number of tailored recombinases within this collection increases the probability that a tailored recombinase is available that recognise a target sequence closely related to sequences within the LTR sequence of proviral DNA a recombinase is required for. Thus with a growing number of recombinases in the collection the likelihood that a wild-type recombinase has to be tailored in a more time consuming method decreases, whereas the likelihood increases that the faster generation (i.e. requiring less evolution cycles) of a specifically tailored recombinase starting from another more closely related tailored recombinase is possible.

In a final aspect the present invention is directed to a collection of tailored recombinases, wherein the members of said collection are each obtained by the methods of the present invention.

Consequently, the collection of tailored recombinases of the present invention preferably comprises expression vectors encoding tailored recombinases, bacteria comprising vectors containing a nucleic acid encoding a tailored recombinase, tailored recombinases in protein form or viral vectors comprising the nucleic acid encoding tailored recombinases prepared according to good manufacturing practise.

In a preferred embodiment the collection of the present invention comprises expression vectors encoding nucleic acids encoding specifically tailored recombinases. The expression vectors are then either lyophilised or will be stored at temperatures of at least −70° C. Storage of bacteria, proteins or viral vectors is carried out by methods well known in the art.

It will be obvious to the person skilled in the art that the methods of the present invention described above comprise cyclical processes, and aspects of each cycle or the whole cycle is amenable to automation.

BRIEF DESCRIPTION OF THE FIGURES

FIG. 5. The amino acid sequence of the Tre recombinase (SEQ ID NO: 3) is shown. The NLS sequence, added for nuclear localisation of Tre in mammalian cells is underlined. Mutations highlighted in light grey and dark grey (AA 131, 244, 245, 259 and 262) depict DNA contact and non-contact residues based on the Cre crystal structure, respectively. The amino acid number corresponding to the Cre sequence and the mutation analysis presented in FIG. 3 is shown above the mutation.

FIG. 7. Activity of Tre recombinase in E. coli. (A) Schematic representation of LacZ based reporter assay. Site specific recombination leads to the removal of the E. coli promoter, resulting in ablation of LacZ expression. (B) Recombination specificity of Tre illustrated using the lacZ based reporter excision plasmids. The different combinations of loxP or loxltr based reporter plasmids and recombinases used are indicated. White colonies are produced as a result of the removal of the promoter driving lacZ expression after recombination. (C) Activity of Tre recombinase on different target sites after overnight culture at 50 µg/ml L-arabinose concentration of plasmid DNA corresponding to the pEVO versions of different target sites and Tre and digestion with BsrGI and XbaI. The lower recombined band of 4.2 Kb is indicated as a line with one triangle and the upper unrecombined band as a line with 2 triangles. The calculated percentage of recombined plasmid of each target is shown beneath the lanes.

The present invention will be explained in further detail by way of Examples.

EXAMPLE 1

Recombinase Expression and Reporter Plasmids

Various expression vectors were generated for the purpose of the present invention using standard methods and synthetic double-strand oligonucleotides or PCR technology.

Cre and Tre cDNAs were cloned into the vector pIRESneo3 (Clon-tech) utilising the NheI and BamHI restriction sites for expression in mammalian cells.

The multihost reporter vectors pSVpaX and pSVloxltr are identical except for the directly repeated loxP or loxLTR sites flanking the pac region, respectively. pSVpaX has been previously described (BUCHHOLZ et al., 1996). pSVloxltr was generated from pSVpaX by replacing the loxP sites with loxLTR sequences.

The Tat-responsive reporter gene plasmid pHIV/T1/LUC was constructed by ligating the HIV-1 HXB3 LTR between the SpeI and HindIII site, and the firefly luciferase gene between the HindIII and XhoI site of the eukaryotic expression vector pcDNA3 (Invitrogen). Subsequently, the loxLTR sequence of the primary HIV-1 strain TZB0003 (GenBank accession number AF096641) was introduced into the HXB3 LTR by PCR. The plasmid pHIV/T2/LUC was obtained by insertion of a double-stranded loxLTR-encoding oligonucleotide 3' of the luciferase gene between the XhoI and ApaI sites of pHIV/T1/LUC. The HIV-1 Tat-expressing vector pcTat, the parental vector pBC12/CMV, and the internal control vector pBC12/CMV/βGal have been described previously (MALIM et al., 1988; RUHL et al., 1993). The vector p3Tre was generated by ligating the Tre cDNA (SEQ ID NO: 2) between the HindIII and BamHI site of pcDNA3. The plasmid pNLT2ΔenvPuro is a derivative of the pNL4-3 proviral DNA (Gen-Bank accession number M19921) and was constructed by converting the respective NL4-3 LTR sequences by PCR into the loxLTR sequence of HIV-1 TZB0003. Subsequently, a 537 bp fragment within the env gene (nucleotide position 6712 to 7249) was deleted. Finally, the nef coding sequence was replaced by the puromycin resistance gene. The vector expressing the envelope glycoprotein of vesicular stomatitis virus, pCMV-VSV-G, has been described (BEYER et al., 2002).

EXAMPLE 2

Generation of a Tailored Recombinase Recognising and Recombining an Asymmetric Target Sequence within the LTR of HIV-1

I. Determination of Candidate Asymmetric Target Sequences

Figure 1:
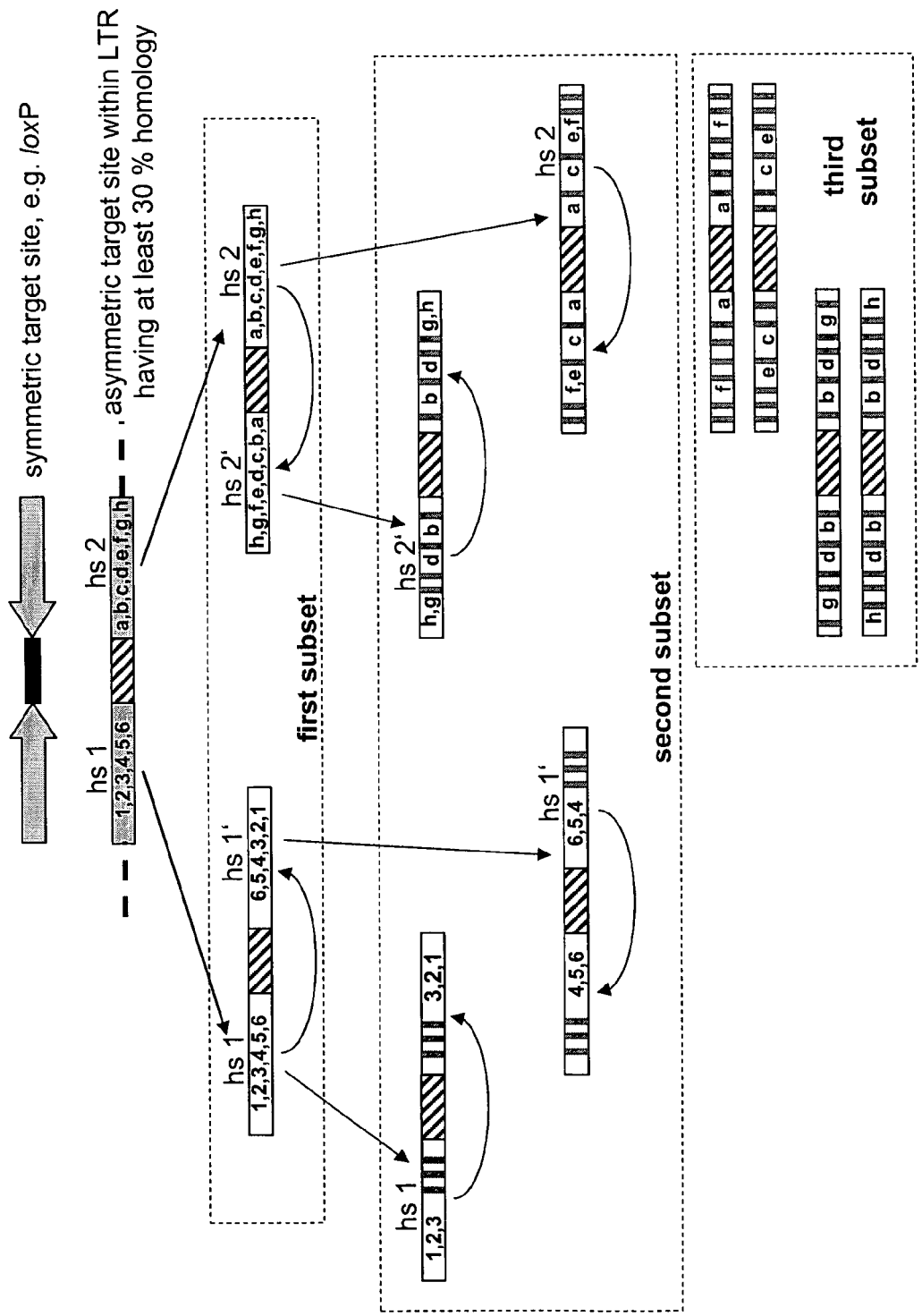
FIG. 1. Strategy of splitting up of asymmetric target sequences. The grey shaded arrows depict the inverted repeats of a symmetric target site separated by a spacer sequence (black bar). The numbers and letters within the asymmetric target site represent nucleotides deviating from the homologous symmetric target site. The curved arrows represent the generation of inverted repeats on the basis of a half-site sequence and a spacer sequence. The grey shaded boxes in the target site in the second and the third subset represent nucleotides from the homologous symmetric target site replacing a deviating nucleotide. The spacer sequence in the target sequences of the different subsets may be different from that of the homologous target sequence (and is thus depicted using black stripes on white ground). The chart only exemplifies the nucleotide replacement. The replacements of other nucleotides and of different numbers of nucleotides are equally possible and preferred. Abbreviations: hs1=half-site sequence 1; hs2=half-site sequence 2, hs1'=inverted repeat generated from half-site sequence 1; hs2'=inverted repeat generated from half-site sequence 2.
Figure 2:
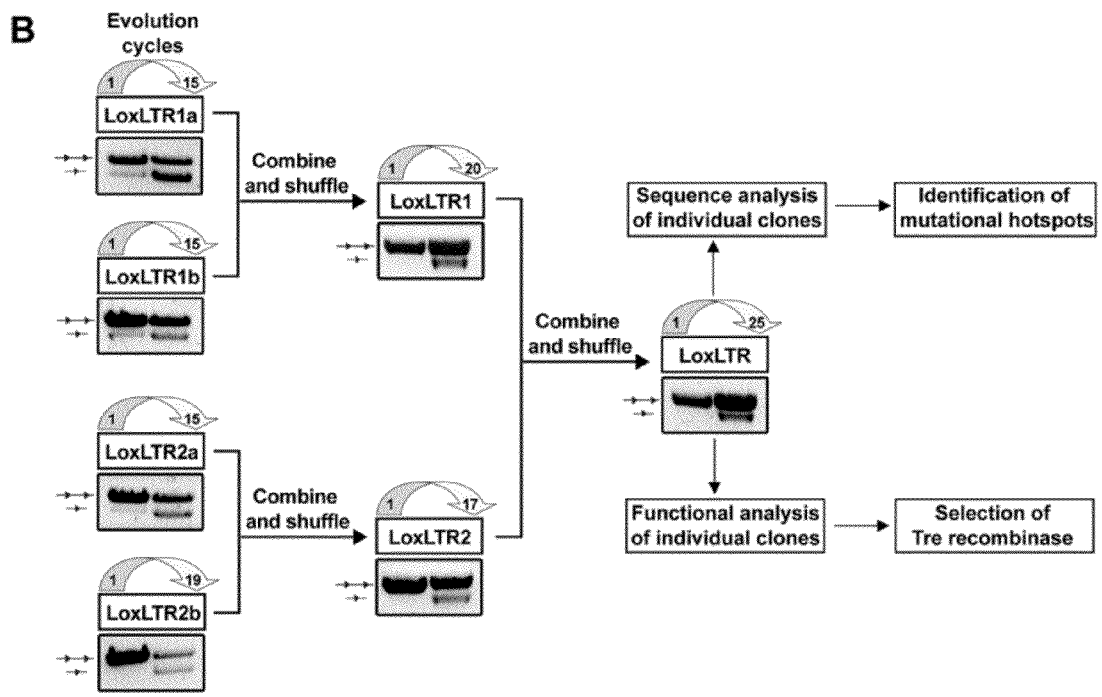
FIG. 2. Combinatorial directed evolution strategy. (A) Recombinase target sites used during the combinatorial substrate linked evolution process are depicted. The bases highlighted in grey represent those different from loxP (SEQ ID NO: 35). The left and right 13 bp sequences of loxltr was used to form the palindromic 34 bp subsets loxltr1 and loxltr2, respectively. loxltrs1a and 1b are derived from loxltr1 and are characterised by two half-site mutations, each corresponding to the palindromic arms. loxltrs2a and 2b were derived from loxltr2 and are characterised by three half-site mutations, each. (B) A summary of the 126 substrate linked directed evolution cycles performed to obtain the Tre recombinase is shown. The number of evolution cycles for each loxltr subset is shown inside the arrows with the final cycle number shown at the arrowhead. The recombinase library activity of the first and the last cycle of the target sites are shown as a restriction analysis of plasmid DNA underneath the respective targets (BsrGI/XbaI digest at an L-arabinose induction of 200 µg/ml). The unrecombined (upper band of 4.9 kb) and the recombined (lower band of 4.2 kb) are indicated as a line with two triangles or one triangle, respectively.

To start the evolution process HIV-1 LTR sequences were scanned first for a sequence with similarity to the canonical loxP site. The chosen sequence belongs to the LTR of the primary HIV-1 strain TZB0003 (BLACKARD et al., 1999) and is part of its modulatory U3 region (sequence position-262 to -229; where the site of transcription initiation is +1). The selected loxLTr site is a 34 bp asymmetric sequence that has 50% sequence similarity to loxP with four mismatches in the left element, six in the right element and a completely different spacer (see FIG. 2A).

II. Examination of the loxLTR Sequence in Substrate Linked Directed Protein evolution in *E. coli*

Figure 3:
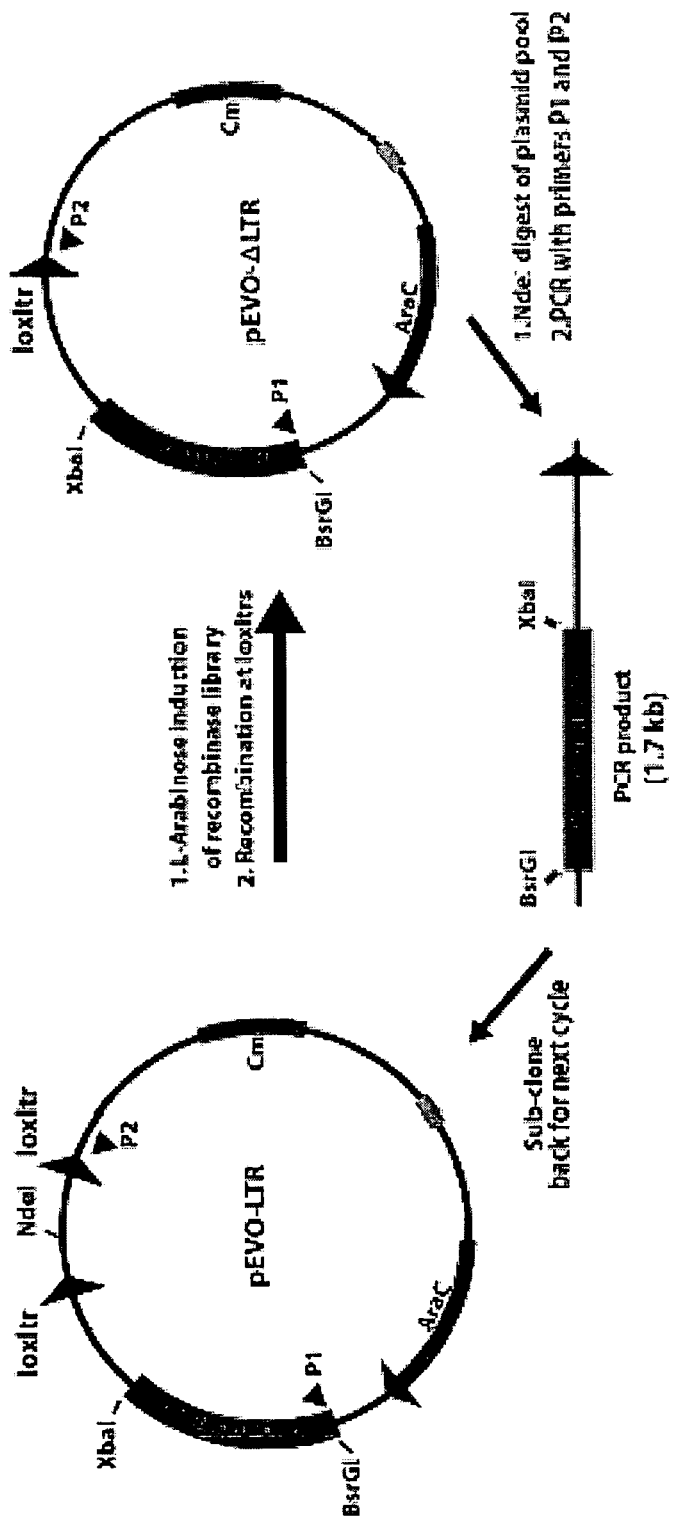
FIG. 3. A representation of the directed evolution strategy used to evolve loxltr specific recombinases is shown. The evolution vectors pEVO-loxltrs are based on the pBAD33 vector and contain two directly repeated recombinase target sites (loxltrs). Recombination at the loxltrs lead to deletion of the intervening region containing a unique NdeI restriction site and successful candidates can be retrieved using PCR with primers P1 (SEQ ID NO: 19) and P2 (SEQ ID NO: 20) after NdeI digestion. The PCR results in a 1.7 Kb band that can be used to subclone back successful recombinases into the starting vector for the next cycle. Restriction digest of the plasmid pool with NdeI ensures removal of unrecombined plasmids (not shown in the figure) and hence eliminates non-functional recombinases.

The loxLTR sequence was examined in substrate linked directed protein evolution as described (BUCHHOLZ & STEWART, 2001) (see also FIG. 3).

690 base pairs fragments containing an NdeI restriction site flanked by loxLTR sites were generated by PCR using the following oligonucleotides using the plasmid pEVO-loxP (BUCHHOLZ & STEWART, 2001) as the template.:

```
Primer sequences for loxLTR:
                                      (SEQ ID NO: 4)
5'-ATGAGATCTACAACATCCTATTACACCCTATATGCCAACATGGAAGC
TTGCATGCCTGCAGATCGAG-3'
and (SEQ ID NO: 5)
5'-TTGAGATCTACAACATCCTATTACACCCTATATGCCAACATGGTCGAACTGTACCGG
TTGTTAGTGA-3'

Primer sequences for loxLTR1:
                                      (SEQ ID NO: 6)
5'-ATGAGATCTACAACATCCTATTACACCCTAAATAGGATGTTGTAAGC
TTGCATGCCTGCAGATCGAG-3'
and (SEQ ID NO: 7)
5'-TTGAGATCTACAACATCCTATTACACCCTAAATAGGATGTTGTTCGA
ACTGTACCGGTTGTTAGTGA-3'

Primer sequences for loxLTR2:
                                      (SEQ ID NO: 8)
5'-ATGAGATCTCCATGTTGGCATAACACCCTATATGCCAACATGGAAGC
TTGCATGCCTGCAGATCGAG-3'
and (SEQ ID NO: 9)
5'-TTGAGATCTCCATGTTGGCATAACACCCTATATGCCAACATGGTCGA
ACTGTACCGGTTGTTAGTGA-3'

Primer sequences for loxLTR1a:
                                      (SEQ ID NO: 10)
5'-ATGAGATCTACAACATCGTATAACACCCTATATACGATGTTGTAAGC
TTGCATGCCTGCAGATCGAG-3'
and
```

-continued

Primer sequences for loxLTR1b:
(SEQ ID NO: 11)
5'-TTGAGATCTACAACATCGTATAACACCCTATATACGATGTTGTTCGA
ACTGTACCGGTTGTTAGTGA-3'

(SEQ ID NO: 12)
5'-ATGAGATCTATAACTTCCTATTACACCCTAAATAGGAAGTTATAAGC
TTGCATGCCTGCAGATCGAG-3'
and (SEQ ID NO: 13)
5'-TTGAGATCTATAACTTCCTATTACACCCTAAATAGGAAGTTATTCGA
ACTGTACCGGTTGTTAGTGA-3'

Primer sequences for loxLTR2a:
(SEQ ID NO: 14)
5'-ATGAGATCTCCATCTTCGTATAACACCCTATATACGAAGATGGAAGC
TTGCATGCCTGCAGATCGAG-3'

(SEQ ID NO: 15)
5'-TTGAGATCTCCATCTTCGTATAACACCCTATATACGAAGATGGTCGA
ACTGTACCGGTTGTTAGTGA-3'

Primer sequences for loxLTR2b:
(SEQ ID NO: 16)
5'-ATGAGATCTATAAGTTGGCATAACACCCTATATGCCAACTTATAAGC
TTGCATGCCTGCAGATCGAG-3'
and (SEQ ID NO: 17)
5'-TTGAGATCTATAAGTTGGCATAACACCCTATATGCCAACTTATTCGA
ACTGTACCGGTTGTTAGTGA-3'

The PCR fragments were digested with BglII and cloned into the evolution vector digested with the same enzyme. Clones were validated for the correct sequence using the primer 5'-CAATAACCCTGATAAATG-3' (SEQ ID NO: 18) by sequencing.

Starting libraries of recombinases cloned into the evolution vectors pEVO-loxLTR were generated by error prone PCR as described in BUCHHOLZ & STEWART (2001). The evolution vector is based on the pBAD33 vector (GUZMAN et al., 1995) and contains two directly repeated recombinase target sites (loxltrs). The plasmid also contains the araC promoter allowing arabinose inducible expression of the recombinases and a chloramphenicol resistance marker (Cm) for propagation in E. coli. The plasmid also offers convenient cloning of the recombinases using BsrGI and XbaI sites flanking the recombinase coding region. The libraries were transferred into E. coli DH5α cells and grown in LB liquid culture containing chloramphenicol at a concentration of 25 µg/ml. Using the evolution vector (see FIG. 3) and Cre an archive of mutagenised Cre the libraries were tested for recombination activity as described (BUCHHOLZ & STEWART, 2001).

Recombination and subsequent PCR would produce a 1.7 kb band reflecting recombination (see FIG. 3). However, Cre, as well as the library failed to recombine the loxLTR sites and no PCR product was obtained (data not shown), reflecting that the asymmetry and the mutations in loxLTR are too severe to result in recombination.

III. Preparation of Subsets of the Asymmetric Target Sequence loxLTR

To test whether removing the asymmetry of the target site would result in recombination activity, the original loxLTR target was split into two subsets. The palindromic target sites, loxltr1 and loxltr2 were created based on the original asymmetric loxLTR sequence, with the left and right half-site sequences respectively used to form an inverted repeat (see FIG. 2A). However, when loxLTR1 and loxLTR2 were tested for recombination using either Cre or the library, no recombination was observed (data not shown). Hence, the mutations in these sites were still too many for the starting library to display any activity, and this necessitated the further splitting of loxLTR1 and loxLTR2 by evenly dividing the half-site mutations to form four new subsets, termed loxLTR1a, loxLTR1b, loxLTR2a and loxLTR2b (see FIG. 2A).

IV. Performing Substrate Linked Protein Evolution Using the Subsets of the Asymmetric target sequence loxLTR Starting libraries of recombinases cloned into the evolution vectors pEVO-loxltr1a, pEVO-loxltr1b, pEVO-loxltr2a, and pEVO-loxltr2b were generated as described above (see Example 2.11) and were independently transferred into E. coli DH5α cells grown in LB liquid culture containing chloramphenicol at a concentration of 25 µg/ml.

The recombinase libraries at the start of evolution cycles (cycle1) were induced with 200 µg/ml L-arabinose and the arabinose concentration was lowered during the successive cycles until satisfactory recombination was achieved at a minimum induction (0-5 µg/ml) of L-arabinose.

Plasmid DNA isolated after each evolution cycle was digested with NdeI and recombinase coding sequences that had successfully recombined the evolution vector were amplified with primers P1 (5'-TCTACTGTTTCTCCATA-3'; SEQ ID NO: 19) and P2 (5'-TGTCGCCCTTATTCCCT-3'; SEQ ID NO: 20) in a 50 µl PCR mix containing 1× PCR buffer, 250 µM of each dNTP, 3 mM of $MgCl_2$ and 1.5 units of BioTaq DNA polymerase according to the following program: 35 cycles of denaturation at 94° C. for 60 s; annealing at 55° C. for 60 s and elongation at 72° C. for 90 s. The PCR product of the recombined form of the plasmid produces a 1.7 kb band. This PCR product was digested with BsrGI and XbaI and subcloned back into the appropriate pEVO-LTR vectors for the next evolution cycle. The library was maintained above 25000 individual clones for all libraries.

Cre recombined only loxltr1a at very low levels (data not shown), reflecting its high target specificity. In contrast, expression of the mutagenised library resulted in low recombination activity at all loxLTR subsets. Splitting the mutations facilitated recognition by the Cre library, and hence served as a starting point for subsequent directed evolution cycles. Reiterative directed evolution cycles resulted in enrichment of the recombinase libraries with functional candidates (see FIG. 2B). The number of evolution cycles required to obtain efficient recombinases for each loxLTR varied between the loxLTR subsets, but eventually efficient recombination activity of the libraries was observed for all subsets.

V. Pooling of the Libraries and DNA Shuffling to Allow Recombination of the Next Higher Subset To test whether a combinatorial approach would now allow recombination of the next higher subsets, the libraries 1a and 1b, and 2a and 2b, respectively, were pooled and shuffled.

DNA shuffling (STEMMER, 1994) was carried out to recombine the obtained Cre mutants in vitro after each third evolution cycle and also to recombine recombinase libraries of lower subsets to initiate evolution against higher loxLTR target sites. Briefly, DNA fragments containing the recombinase gene were randomly fragmented by sonication using 12% amplitude for 5 minutes with 30 s pulse on and 5 s pulse off using a 450-D Digital Sonifier from Branson. The sonicated fragments (100-400 bp in size) were purified using the PCR purification kit (Qiagen). To reassemble the fragments, 2 µg of the sonicated DNA was added to a 50 µl PCR mix and amplified using the same program stated above (see Example 2.IV). 3 µl of this primerless PCR reaction product was used as a template for the next PCR with primers P1 (5'-TCTACT-GTTTCTCCATA-3', SEQ ID NO: 19) and P3 (5'-GCGGAT-GAGAGAAGATT-3'; SEQ ID NO: 21) in a 50 µl PCR mix with the same cycling conditions. The shuffled library (final PCR product) was digested with BsrGI and XbaI and cloned back into the appropriate pEVO vectors harbouring loxLTR1 and loxLTR2, respectively. The combination of mutations from the different libraries resulted in synergistic effects and led to the generation of recombinases, which now recombined loxLTR1 and loxLTR2 (see FIG. 2B), demonstrating that an evolution strategy traversing through intermediates can be used to achieve a desired activity.

VI. Pooling of the Libraries and DNA Shuffling to Allow Recombination of the Asymmetric Target site within the LTR The loxP sequence is a symmetric site that is bound by two Cre monomers. A recombinase that recombines an asymmetric target site hence has to recognise half-sites of varying sequence. In order to test whether a recombinase can be obtained through substrate linked protein evolution address recombining the asymmetrical loxLTR target site, the libraries from loxLTR1 and loxLTR2 were pooled and shuffled and assayed for recombination in the evolution vector harbouring the asymmetrical loxLTR target sequence. Very low recombination activity was detected in the first cycles that was enriched for functional candidates in later cycles (see FIG. 2B), demonstrating that symmetry in the target site is not a prerequisite for the site specific recombination reaction.

After a total of 126 evolution cycles, the evolution process was halted and individual loxLTR specific recombinases were examined for their recombination properties. Fifty individual recombinases were functionally analysed using restriction analysis in *E. coli* (data not shown).

The most active recombinase (termed Tre for LTR recombinase) showed efficient recombination of the loxLTR site with some residual activity for loxP when tested in a lacZ based reporter assay (see FIGS. 7A and B). To quantify the target specificity of Tre its recombination properties were examined in the evolution vectors of all the loxLTR subsets (see FIG. 7C). As in the reporter assay, Tre efficiently recombined the loxLTR sequence and displayed residual activity on loxP (see FIG. 7C). Tre also showed efficient recombination on loxLTR2b and residual activity on loxLTR2, but no recombination was observed on loxLTR1a, loxLTR1b, loxLTR1, and loxLTR2a (see FIG. 7C). This is remarkable when taking into consideration that Tre evolved from these subsets. This observation confirms previous findings that target specificity is regained after initial relaxation in directed evolution over many generation cycles (BUCHHOLZ & STEWART, 2001; SANTORO & SCHULTZ, 2002); MATSUMURA & ELLINGTON, 2001).

VII. Sequencing of Evolved Recombinases

Figure 4:
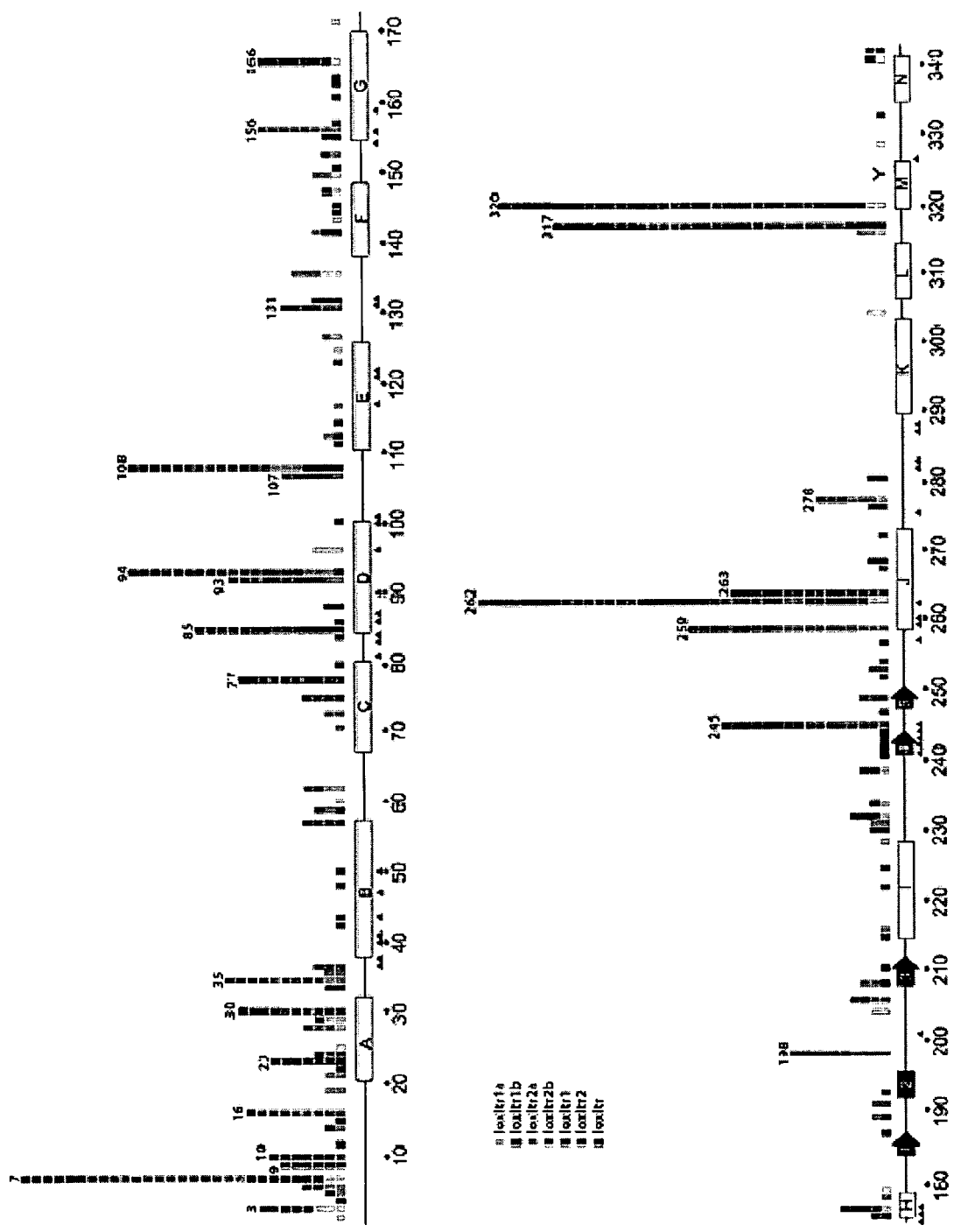
FIG. 4. Mapping of mutations of evolved recombinases onto Cre secondary structure. The appearances of the mutations are shown in the indicated colour code. Amino acid mutations appearing more than once add to the bar. Structural elements of Cre are shown as bars for α-helices (A to N) and arrows for β-sheets (1 to 5) based on the crystal structure of Cre recombinase. The catalytic tyrosine is denoted by "Y". The filled triangles mark amino acids making specific contacts with DNA. Hypervariable codons are indicated by the amino acid position above the bars.
Figure 6:
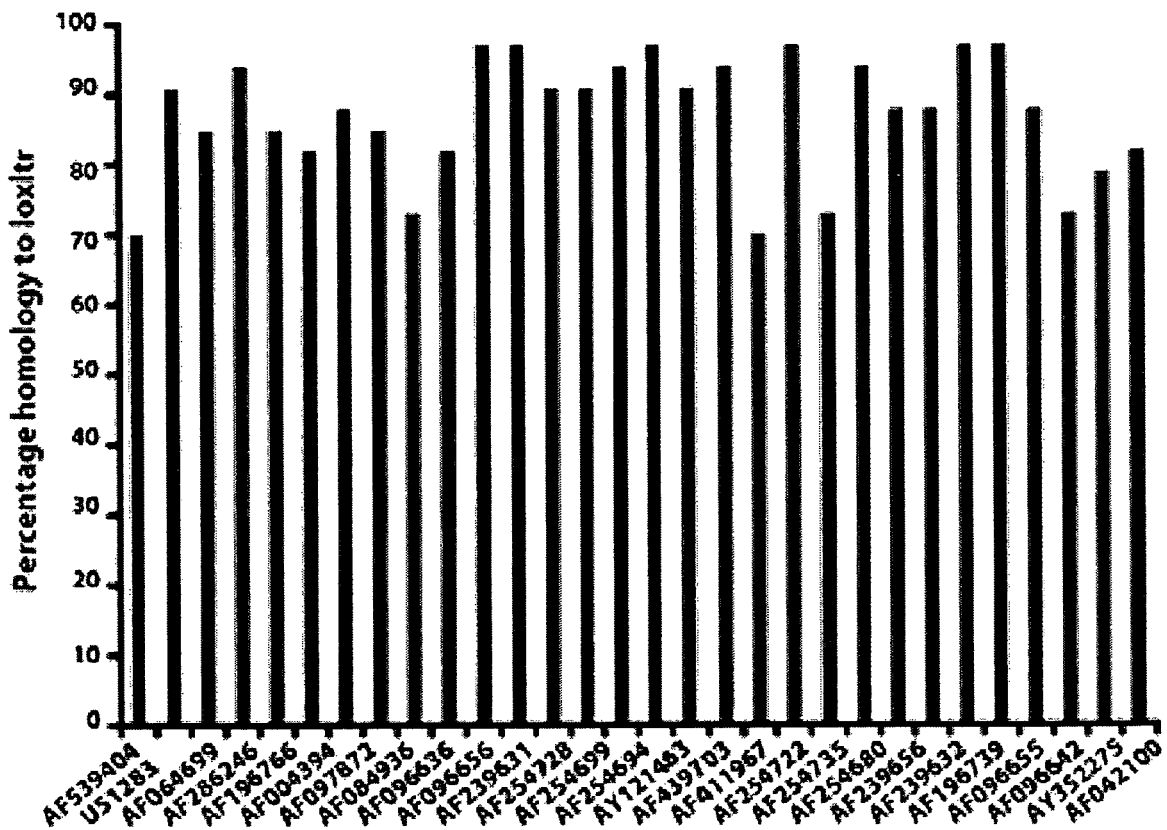
FIG. 6. Comparison of the loxltr sequence with other HIV-1 LTR sequences. A random selection of 27 HIV-1 LTR sequences was aligned to the 34 bp loxltr sequence and the similarities were calculated. The results are shown as percentage sequence homology of loxltr versus all the respective LTRs in the library. The accession numbers of the HIV-1 LTR sequences are shown in the abscissa.

Evolved recombinases from all subsets and loxLTR were sequenced to monitor the evolution process. The sequences revealed clustering of mutations arising from the different subsets that were combined through the course of evolution and complemented by novel clusters in the higher subsets (see FIG. 4 and Table 1).

Table 1 shows amino acid mutations in the sequenced recombinases for the indicated loxltr subsets of evolved recombinases. The shaded residues contact DNA in the Cre crystal structure. The hypervariable residues (also displayed in FIG. 5) are shown in bold letters for both DNA contact and non-contact sites.

TABLE 1

| Evolved recombinases | Amino acid mutations |
| --- | --- |
| 1a.1 | K25E, D29G, A127V, E138G, M149I, D341N |
| 1a.2 | M28A, M97I, V121I, I166T, G229D, D232V |
| 1a.3 | G82S, E150A, L171V, V204A, I320M |
| 1a.4 | A175G |
| 1a.5 | N3D, V7L, K62R, M97I, E138G, D329A |
| 1a.6 | D29A, V145I, E262Q, S305P, T316A |
| 1a.7 | S2T, N3K, L4S, N60S, M97I, R179G, F239L, E262Q, D278G, I320S |
| 1a.8 | N3D, V7L, K62R, V204A, P234L, S305P |
| 1b.1 | N59T, I88V, I166V, I174M, S186T, S214I, P234L, V242A, E262A |
| 1b.2 | V7L, K62N, A112V, R146C, L161Q, F163L, G208R, R241P, E262G, D341G |
| 1b.3 | V7L, Q94L, S108G, E123K, N151T, T268A, N317T, I320M |
| 1b.4 | V7L, C155R, E262Q, N317T, I320S |
| 1b.5 | N3D, V7L, S108C, D143N, E262Q, N317T, I320S |
| 1b.6 | N3D, V7L, S114P, D189G, E262G, I306T |
| 1b.7 | N3D, V7L, S108C, D143N, E262Q, N317T, I320S |
| 1b.8 | L4I, V7L, K86R, S108G, E210K, I320S, D343E |
| 2a.1 | L5P, L14F, Q156R, D189G, M193A, L215Q, I320S |
| 2a.2 | G93A, A112T, E138G, D143G, D278G, T316A |
| 2a.3 | V7L, Q94L, R118G, A127P, D153N, A178P, N319S |
| 2a.4 | N10H, P107I, T253S, T316A, I320S |
| 2a.5 | T6S, D21E, Q94L, L98I, E138G, G198S, A231V |
| 2a.6 | T19M, Q35R, E150V, G191E, G198S, S254C, D278G |
| 2a.7 | T6S, D21E, Q94L, L98I, E138G, G198S, A231V |
| 2a.8 | T19M, Q35R, E150V, G191E, G198S, S254C, D278G |
| 2b.1 | V7L, V16A, M30V, Q35P, N59S, A131V, D157E, A249T, R259C, E262Q, N317T, I320S, T332A |
| 2b.2 | V7L, R24H, M28I, A36V, F37L, D73Y, Y77H, P107L, A131V, T206A, E262A, D277G, N317T, I320S |
| 2b.3 | V7L, V16A, M30V, Q35P, S108G, G208R, E262A, N317T, I320S, G342W |
| 2b.4 | V7L, V16A, M30V, V71A, N111S, Q156K, A249T, Q255R, R259C, E262Q, N317T, I320S |
| 2b.5 | N3D, V7L, M30V, Q35P, S108G, A249T, E262Q, A267G, N317T, I320S |
| 2b.6 | V7L, V16A, M30V, Q35P, Y77H, G93C, Q156K, R259C, E262Q, N317T, I320S |
| 2b.7 | V7L, V16A, M30V, Q35P, S108G, G208R, E262A, N317T, I320S, G342W |
| 2b.8 | V7L, R24H, M28I, A36V, F37L, D73Y, Y77H, P107L, A131V, T206A, E262A, D277G, N317T, I320S |

TABLE 1-continued

| Evolved recombinases | Amino acid mutations |
|---|---|
| 1.1 | L75F, V85A, Q94L, S108G, C155R, G198S, E262G, D278G, N317H, I320S |
| 1.2 | V85A, Q94L, S108G, G198S, D232E, E262G |
| 1.3 | V48I, R50Q, Q94L, V230A, S257T, E262R, N317T, I320S |
| 1.4 | V23A, L75F, V85A, Q94L, R101Q, S108G, G230A, E262H, N317T, I320S |
| 1.5 | V7L, Q9H, N10S, V23A, D29E, R34H, K62E, L75F, V85A, Q94L, S108G, L164P, T206A, F239L, V247A, E262H, N317T, I320S |
| 1.6 | V85A, Q94L, S108G, D153N, G198S, D232E, E262G, N317T, I320S |
| 1.7 | V85A, Q94L, S108G, I174M, T206A, F239L, E262A, D278G, N317T, I320S |
| 1.8 | L75F, V85A, Q94L, S108G, G198S, E262R, D278G, N317T, I320S |
| 2.1 | T6I, V7L, V16A, R24C, M30V, K57E, G93C, Q156K, I166V, N245Y, R259Y, E262Q, G263R, I272V, N317T, I320S |
| 2.2 | M44T, S51L, Y77H, G93C, P107L, N245Y, R259Y, E262Q, G263R. |
| 2.3 | N3D, V7L, V16A, Q35P, K57E, Y77H, G93C, P107L, A131V, S147L, Q156K, N245Y, R259Y, E262Q, G263R, N317T, I320S |
| 2.4 | V7L, V16A, V23A, M30V, Y77H, G93C, P107L, Q156K, R243G, N245Y, R259Y, E262Q, G263R. |
| 2.5 | V7L, G93C, Q156K, A175G, E222G, N245Y, R259Y, E262Q, G263R, N317T, I320S |
| 2.6 | Q35P, Y77H, G93C, Q156K, N245Y, R259Y, E262Q, G263R, N317T, I320S |
| 2.7 | M28I, M30V, Q35P, Y77H, G93C, A131V, N245Y, R259Y, E262Q, G263R |
| 2.8 | K57E, G93C, N245Y, R259Y, E262Q, G263R, N317T, I320S |
| Tre | V7L, Q9H, N10S, V16A, M30V, Q35P, K43E, Y77H, G93C, Q94L, A131T, I166V, K244R, N245Y, R259Y, E262Q, G263R, N317T, I320S. |
| Loxltr.1 | E22G, F37S, A84V, V85A, Q94L, S108G, K132N, I166V, A175S, N245Y, R259Y, Q281R, N317T, I320S. |
| Loxltr.2 | L5Q, V7L, P12S, L14S, P15L, V23A, A80V, V85A, Q94L, S108G, G198S, N245Y, R259Y, E262Q, G263R, T268A, N317T, I320S. |
| Loxltr.3 | T6I, V7L, Q9H, N10S, V23A, V85A, Q94L, K132N, I166V, A175S, D232G, N245Y, R259H, E262Q, G263R, N317T, I320S. |
| Loxltr.4 | N59W, Y77H, V85A, Q94L, S108G, N245Y, R259H, E262Q, G263R, N317T, I320S. |
| Loxltr.5 | V7L, Q9H, N10S, K57E, V85A, Q94L, S108G, G198S, N245Y, R259H, E262Q, G263R, Q281R, N317T, I320S. |
| Loxltr.6 | V7L, Q9H, N10S, V23A, V85A, I88V, Q94L, S108G, M149I, I166V, N245Y, R259Y, E262Q, G263R, N317T, I320S. |
| Loxltr.7 | V7L, Q9H, N10S, V23A, R34H, V85A, Q94L, S108G, K132N, I166V, A175S, I225V, N245Y, R259Y, E262Q, G263R, N317T, I320S. |

In total, Tre has 19 amino acid changes when compared to Cre, with many of these mutations originating from the different subsets (see FIG. 5).

EXAMPLE 3

Characterisation of the Tre Recombinase

I. Recombination Properties of Tre in Mammalian Cells

HeLa cells were cultured at 37° C. under 5% CO2 in DMEM containing 100 units/ml of penicillin and streptomycin and supplemented with 10% FCS unless stated otherwise.

A puromycin resistant pSVloxltr reporter cell line was obtained by transfection of 2×10⁶ cells with 8 µg of the reporter plasmid using Effectene transfection reagent (Qiagen) according to the manufacturer's instructions, and selection with 5 µg/ml puromycin (Invivogen). The final stable cell line was grown in presence of 3 µg/ml of puromycin.

HeLa cells were cotransfected with recombinase expression—and reporter plasmids in a 1:2 ratio in 6-well format using Effectene (Qiagen). A total of 0.6 µg of DNA was used for transfections. Parallel transfections with recombined version of the reporter plasmids were carried out to calculate the percentage of recombined reporter plasmids.

Recombinase activity was evaluated 48 hours post transfection by assaying relative β-galactosidase activities 48 hours post transfection using the Tropix Galacto-Light kit (Applied Bio-systems, Bedford, Mass.) according to manufacturer's protocol. Briefly, HeLa cells were washed with PBS 48 hours posttransfection, and fixed with 2% formaldehyde and 0.1% glutaraldehyde, permeabilised with 0.5% Triton-X 100 and stained overnight at 37° C. with staining solution containing 1 mg/ml X-gal, 2 mM $MgCl_2$, 5 mM potassium ferricyanide and 5 mM potassium ferrocyanide. Recombination efficiencies were corrected for total protein content in the cell lysate measured by BCA protein assay kit (Pierce, Rockford, Ill.).

Figure 8:
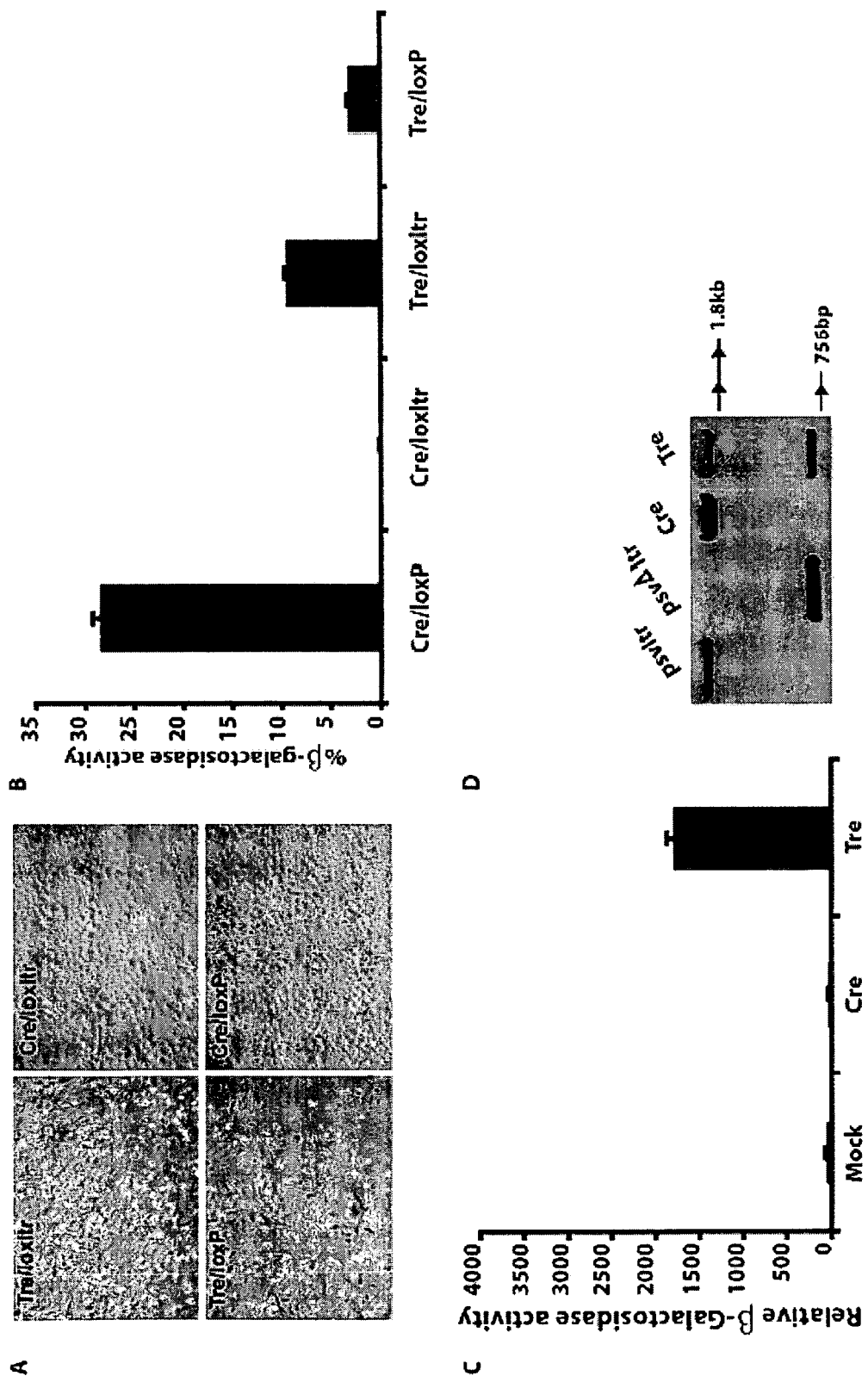
FIG. 8. Assay for transient recombinase activity in HeLa cells. (A) HeLa cells were co-transfected with indicated recombinase and reporter plasmids (see FIG. 6). The cells were fixed and stained with X-gal 48 hours post transfection. Recombination deletes an intervening stop region and results in activation of lacZ expression reflected by blue cells. (B) Measurement of β-galactosidase activity in cell lysates of HeLa cells co-transfected with indicated recombinase and reporter plasmids. The β-galactosidase activity is presented as a percentage of the enzyme activity of cells after parallel transfection with the recombined forms of reporter plasmids pSVΔpaX and pSVΔloxltr. (C) Recombination mediated by Tre in a stable loxltr HeLa reporter cell line. The cell line was transfected with mock, Cre and Tre expression vector and β-galactosidase activity was measured in cell lysates 48 hours post transfection. (D) PCR detection of recombination in the loxltr cell line described in (C) after transfection with Cre and Tre expression vectors. The PCR products for the unrecombined and recombined control plasmid (pSVloxltr and pSVΔ-loxltr) and after transfection with Cre and Tre expression vectors are shown. The lower recombined band is denoted with a line with one triangle and the upper unrecombined band with a line with two triangles. The length of the PCR products is indicated.

As in the *E. coli* assays, Cre efficiently recombined the loxP reporter, but did not recombine loxLTR and Tre showed efficient recombination on the loxLTR reporter and some residual activity on loxP (see FIGS. 8A and B). To investigate whether Tre can recombine its target in a genomic context, a stable loxLTR reporter cell line was tested for recombination after transfection with a Tre expression plasmid.

The loxLTR stable cell line was generated by puromycin selection (2 µg/ml) of HeLa cells transfected with the pSVloxltr plasmid. For the recombination assay, this cell line was transfected with 0.8 µg either mock, Cre or Tre plasmids using Effectene in 6-well format and assayed for β-galactosidase activities 48 hours post transfection using the Galacto-Light kit (Applied Biosystems, Bedford, Mass.). The β-galactosidase activities were corrected for transfection efficiencies by measurement renilla luciferase activities in cell lysates.

PCR assays and β-galactosidase activity measurements demonstrated that Tre recombines loxLTR sequences packaged in chromatin (see FIGS. 8C and D).

For the PCR assays the loxLTR HeLa cell line was transfected with respective recombinase expression vectors using Effectene. Transfected cells were washed with PBS after 48 hours, and trypsinised. Genomic DNA was isolated using QIAamp DNA Blood mini kit (Qiagen) according to the manufacturer's instructions. Genomic DNA (3 µg) was analysed for recombination using primers P' (5'-GCCTCG-GCCTAGGAACAGT-3'; SEQ ID NO: 22) and P" (5'-CCGC-CACATATCCTGATCTT-3'; SEQ ID NO: 23) using the PCR program with 30 cycles of denaturation at 95° C. for 30 s; annealing at 62° C. for 30 s, and elongation at 72° C. for 40 s in a 50 µl PCR reaction containing 1× PCR buffer, 250 µM of each dNTP, 3 mM of MgCl$_2$ and 1.5 units of BioTaq DNA polymerase. The PCR products were visualised on a 0.7% agarose gel.

II. Examination of Tre-Mediated Recombination in the HIV-1 LTR Context

Figure 9:
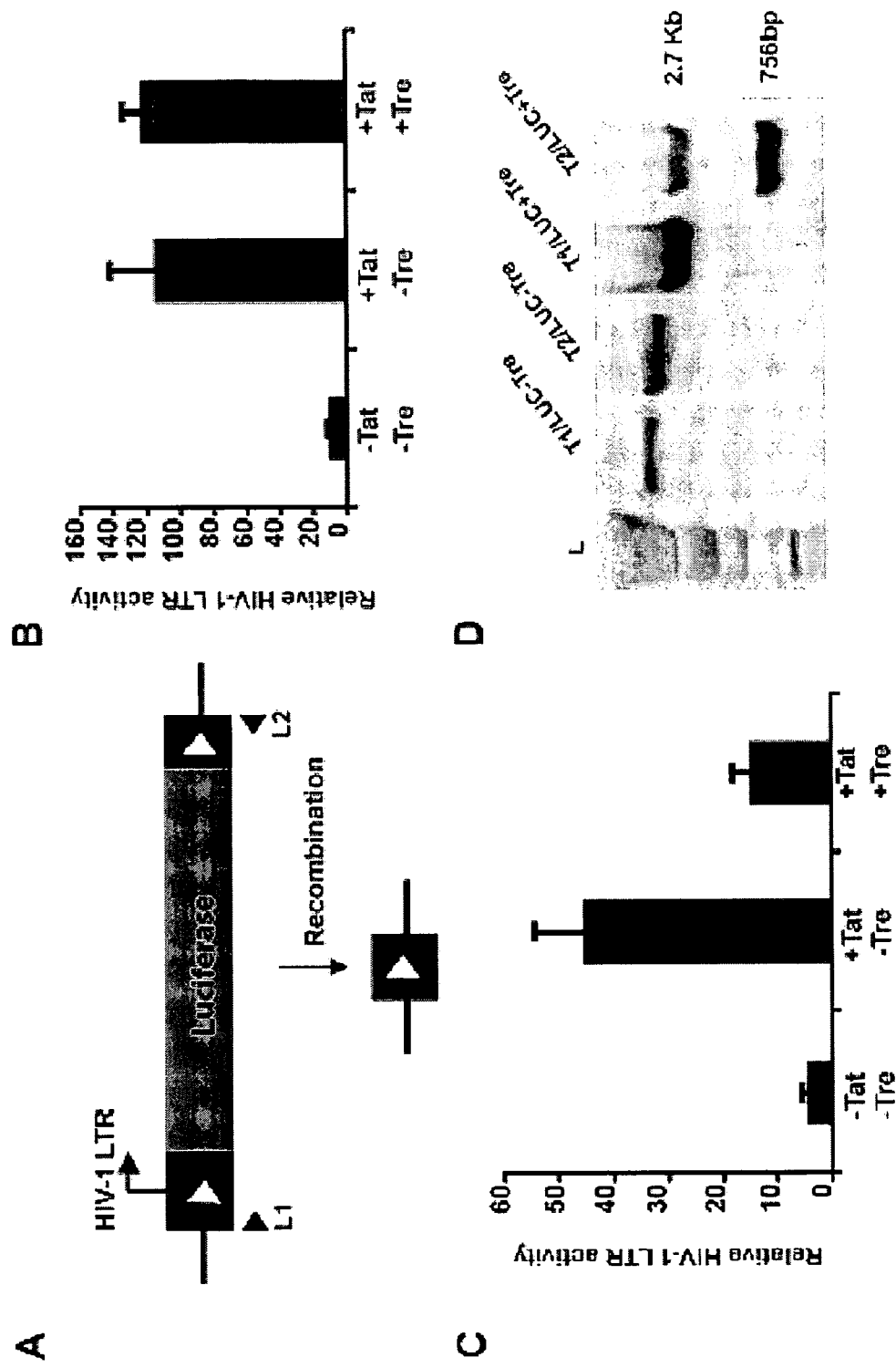
FIG. 9. HIV-1 Tat transactivation assay in HeLa cells. (A) Schematic diagram of the reporter vector pHIV/T2/LUC that contains the loxltr sequence (denoted by a white triangle) within the U3 region of the HIV-1 HXB3 LTR. Another copy of the loxltr sequence, which is absent in the pHIV/T1/LUC control vector, is located 3' of the luciferase gene. The LTR promoter encodes in its R region the Tat-responsive TAR region. Tat transactivation is reflected by increased expression of firefly luciferase. L1 and L2 denote the primer pair used for PCR detection of recombination (black triangles). Recombination via the loxltr sites will delete the luciferase coding region. (B) Relative HIV-1 LTR activity after transfection of HeLa cells with the control vector pHIV/T1/LUC in presence and absence of Tre. The firefly luciferase activity was measured from the respective transfected cell lysates at 48 hours post transfection. The activities were corrected for transfection efficiency by using a LacZ vector as an internal control and measuring the β-galactosidase activity from the cell lysates. (C) Relative HIV-1 LTR activity after HeLa cells were transfected with the pHIV/T2/LUC vector in presence and absence of Tre. Cell lysates were assayed as before. (D) PCR detection of Tre-mediated recombination in HeLa cells transiently cotransfected with Tat expression plasmid and the indicated vectors. The lower band of 756 bp represents the recombined fragment after loss of the luciferase coding region and is only detectable in cells transfected with pHIV/T2/LUC and Tre expression vector.

HIV Tat reporter constructs were generated and tested in Tat assays (see FIG. 9). The Tat protein is an essential viral transactivator that regulates HIV LTR promoter-directed transcription (EMERMAN & MALIM, 1998). For subsequent analyses the loxLTR sequence was introduced in an HIV-luciferase reporter vector (pHIV/T1/LUC; control vector) within the HIV-1 HXB3 LTR (RATNER et al., 1985). In addition, another copy of the loxLTR sequence was inserted 3' of the luciferase coding sequence to generate pHIV/T2/LUC (depicted in FIG. 9A). Thus, Tat transactivation results in expression of firefly luciferase driven by the LTR promoter in these vectors.

For transient Tat transactivation assays, HeLa cells were transfected in 12 well format using Effectene transfection reagent (Qiagen). The transfection mix contained 0.16 µg HIV/T2/LUC or HIV/T1/LUC expressing firefly luciferase, 0.16 µg of pIres-neo-Tre recombinase vector or the empty vector as negative control, 0,08 µg of the Tat vector or pcDNA3 as negative control for Tat. The cells were lysed 48 hours post transfection and assayed for firefly luciferase activity by using Firefly and Renilla luciferase assay kit (Biotium, Inc., Hayward, Calif.). The activities were corrected for transfection efficiency by using a lacZ vector as an internal control and measuring the β-galactosidase activity from the cell lysates.

When HeLa cells were cotransfected with a Tre expression vector along with the Tat vector and pHIV/T2/LUC, a three-fold decrease in luciferase activity was observed (see FIG. 9C). In contrast, no decrease in luciferase expression was detected when the same experiment was performed using the pHIV/T1/LUC control (see FIG. 9B).

To prove that the observed decrease in luciferase expression was a result of recombination and not of blocking the Tat activity or transcription from the LTR promoter by the recombinase, PCR analysis was performed, assaying for recombination upon Tat transactivation (see FIG. 9D).

PCR analysis of recombination on the Tat transactivation assay was carried out on DNA isolated from HeLa cells transfected with the HIV reporter vectors in presence or absence of the recombinase, using primers L1 (5'-GAAG-GTGGGTTTTCCAGTCA-3'; SEQ ID NO: 24) and L2 (5'-AGGGAAGAAAGCGAAAGGAG-3'; SEQ ID NO: 25) employing the PCR program with 30 cycles of denaturation at 95° C. for 30 s, annealing at 60° C. for 30 s, and elongation at 72° C. for 40 s in a 25 µl PCR reaction containing 1× PCR buffer, 250 µM of each dNTP, 3 mM of MgCl$_2$ and 1.5 units of BioTaq DNA polymerase. The PCR products were visualised on a 0.7% agarose gel. The PCR products were gel extracted, purified using Gel extraction kit (Qiagen) and used for sequencing.

Recombination results in a band size of 756 bp due to removal of the luciferase coding sequence, while in absence of recombination the band size is 2.7 kb. PCR on cells transfected with the pHIV/T1/LUC vector, containing just one loxLTR site, produced only the 2.7 kb band both in presence and absence of Tre. In contrast, PCR on cells transfected with the pHIV/T2/LUC vector predominantly displayed the lower band, demonstrating that the reduction of Tat activation was due to Tre mediated excision of the luciferase cassette (see FIG. 9D). Gel extraction of the PCR fragments followed by sequencing confirmed the precise excision of the loxLTR flanked sequence (data not shown).

EXAMPLE 4

Excision of a Full-Size Provirus from the Genome of HIV-1 Infected Human Cells

The capability of Tre to excise a full-size provirus from the genome of HIV-1 infected human cells was examined.

Figure 10:
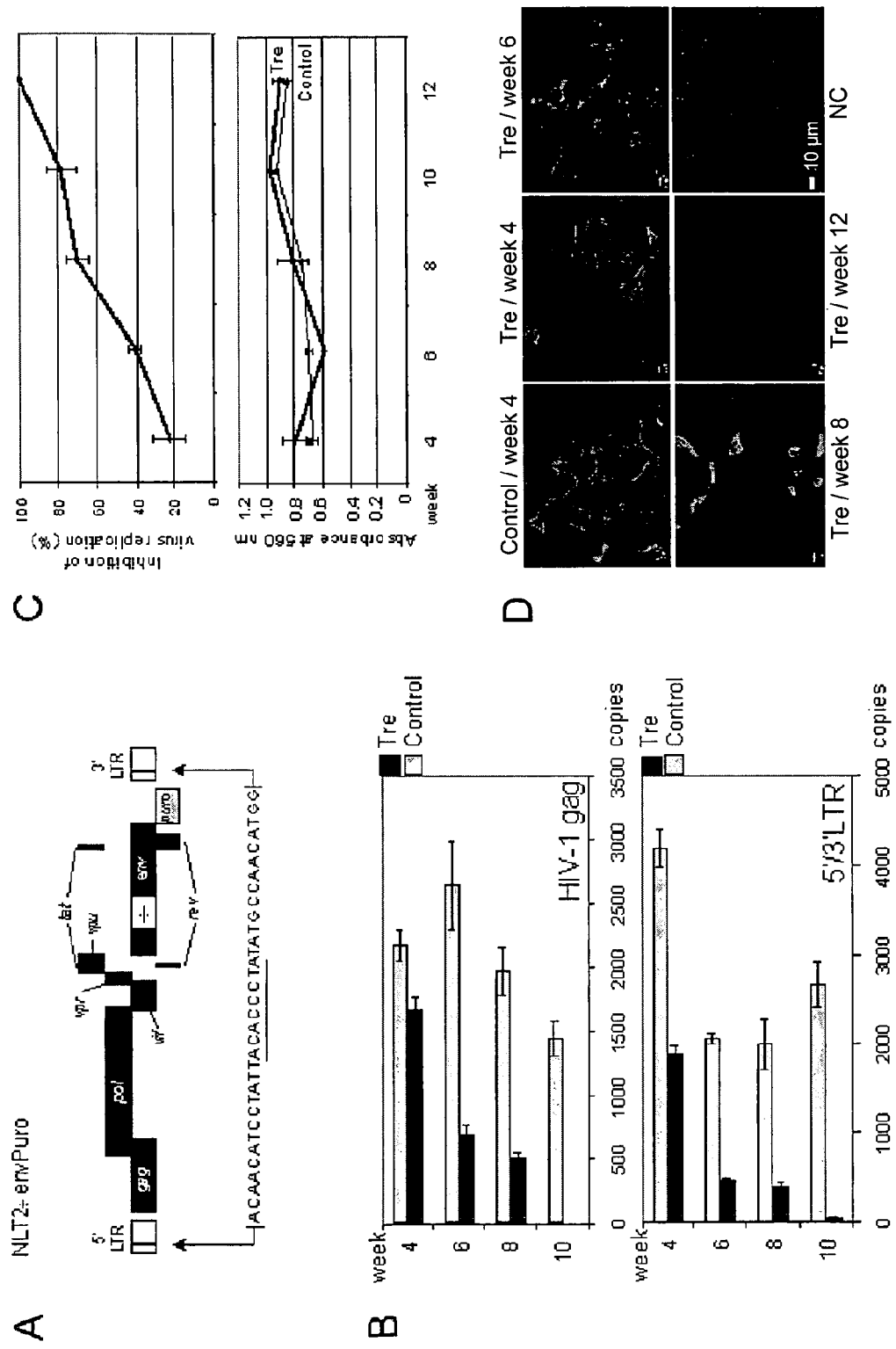
FIG. 10. Tre-mediated recombination of HIV-1 proviral DNA. (A) Schematic diagram of the NLT2ΔenvPuro provirus. The loxltr sequence located in the 5' and 3' LTR is depicted. The spacer sequence is underlined. The nef coding region is substituted by the puromycin resistance gene (light grey box), and envspecific sequences were deleted (Δ). Respective VSV-G pseudo-types were used to infect HeLa cells. (B) Detection of integrated provirus (HIV-1 gag; upper diagram) and recombination of the 5' and 3' LTR region (5'/3'LTR; lower diagram) by quantitative real-time PCR of total genomic DNA isolated from the infected and either Tre expressing (Tre) or Tre-deficient (control) cells at week 4, 6, 8 and 10 posttransfection. Each sample was examined in triplicates. (C) Analysis of virus particle release and cell viabilities. Antigen p24Gag levels in the culture supernatants were determined by ELISA (upper diagram) at the indicated weeks posttransfection. The percentage of inhibition of viral replication within the Tre expressing culture, compared to the control cells, is shown. Cell viabilities were simultaneously monitored by alamarBlue assay (lower diagram). (D) Detection of Gag expressing cells (light grey label) by indirect immunofluorescence in the control culture (Control) at week 4, or in the Tre expressing culture at week 4, 6, 8, and 12 posttransfection. Incubation of control cells with the Cy2-coupled secondary antibody alone served as negative staining control (NC). Nuclei were visualised by DRAQ5 staining (dark label).

To test this, a proviral DNA, derived from the HIV-1 strain NL4-3 (ADACHI et al., 1986), was constructed that contains the loxLTR sequence in its 5' and 3' LTR (depicted in FIG. 10A). In this construct, the nef reading frame, which is dispensable for virus replication in cell culture, was substituted by the puromycin resistance gene. In addition, the increase in total genome length was compensated by deletion of env-specific sequences.

Viral pseudotypes were produced by transient cotransfection of 293T cells with this proviral DNA and an expression vector encoding the vesicular stomatitis virus envelope glycoprotein (VSV-G). Briefly, the HIV-1 pseudotypes were produced by transient cotransfection of 1×10$^6$ 293T cells with 3 µg pNLT2ΔenvPuro and 3 µg pCMV-VSV-G in OptiMEM I (Invitrogen) without antibiotics using 4 µl polyethylenimine (PEI; 1 mg/ml) according to the manufacturer's protocol (Polysciences, Inc.). At day 2 posttransfection viral supernatant was collected and passed through 0.2 µm pore size filters to ensure the removal of any viral aggregates and cells and the p24$^{Gag}$ antigen level was determined by ELISA (Innotest HIV p24 Antigen mAb; Innogenetics N. V.).

Subsequently, 5×10$^5$ HeLa cells, cultured in DMEM containing 15% fetal calf serum (Pansystems GmbH) and antibiotics (penicillin and streptomycin), were infected in a six well plate by spinoculation (O'DOHERTY et al., 2000) with 1000 ng/ml of the pseudotyped virus together with 1 µg/ml polybrene (Sigma-Aldrich) at 1,200×g for 90 min at room temperature. At 24 hours postinfection the culture medium was changed and cells were washed to remove free virus. At 3 days postinfection the cell culture was supplemented with 1 µg/ml puromycin (Sigma-Aldrich) for 2 weeks, and with 0.5 µg/ml puromycin for another 4 weeks to select and clone infected virus particle-releasing cells. Medium was changed every second day to eliminate dead cells.

The infected virus particle-releasing cells were then transfected either with a plasmid expressing Tre or with the parental control vector, both also carrying the neomycin resistance gene. The respective neomycin-resistant cell pools were monitored with respect to recombinase activity and virus production.

Total genomic DNA was isolated from infected HeLa cells using the Blood & Cell Culture DNA Midi kit (Quiagen) in accordance to the manufacturer's protocol. Quantitative real-time PCR revealed that the presence of HIV-1 gag-specific sequences in the cellular genome constantly declined over time in Tre expressing cells, as compared to control cells (see FIG. 10B, upper diagram). Quantitative PCR specific for HIV-1 gag (gag-forward: 5'-ATCAATGAGGAAGCTGCA-GAA-3' (SEQ ID NO: 26), gag-reverse: 5'-GATAGGTG-GATTATGTGTCAT-3' (SEQ ID NO: 27), gag-probe: 5'-FAM-ATTGCACCAGGCCAGATGAGAGAA-TAMRA-3' (SEQ ID NO: 28)) and 5'/3' LTR recombination (LTR-forward: 5'-GATGGTGCTAC-AAGCTAGTAC-3' (SEQ ID NO: 29), LTR-reverse: 5'-CTGTCAAACCTCCA-CTCTAAC-3' (SEQ ID NO: 30), LTR-probe: 5'-FAM-AAG-GAGAGAACAAC-ATCCTATTACAC-TAMRA-3' (SEQ ID NO: 31)) was performed as follows: 40 cycles containing 100 ng genomic DNA, 300 nM forward primer, 900 nM reverse primer and 200 nM hybridisation probe using Platinum qPCR Super Mix UDG (Invitrogen) in an Applied Biosystems 7500 Fast Real-Time PCR System. Each sample was tested in triplicates, and results were normalised using amplification of the same genomic DNA with human β-globin primers (HBG-forward: 5'-CTTAATGCCTTAACATTGTGTATAA-3' (SEQ ID NO: 32), HBG-reverse: 5'-GAATATGCAAATAAGCA-CACATATAT-3' (SEQ ID NO: 33), HBG-probe: 5'-FAM-ACTTTACACAGTCTGCCTAGTACATTAC-TAMRA-3' (SEQ ID NO: 34)).

After 10 weeks of culturing, gag sequences could not be detected anymore. This result was closely mirrored by a similar analysis in which recombination of the 5' and 3' LTR was determined (see FIG. 10B; lower diagram).

Furthermore, cessation of particle budding, which was tracked by determining p24Gag antigen levels in the culture supernatants, occurred with a slightly delayed kinetic, resulting in 100% inhibition of particle release as compared to the Tre-deficient control culture at week 12 (see FIG. 10C, upper diagram). A parallel cytotoxicity assay with alamarBlue (Serotec) failed to record any Tre-induced toxic effects on cellular metabolism (see FIG. 10C, lower panel).

Figure 11:
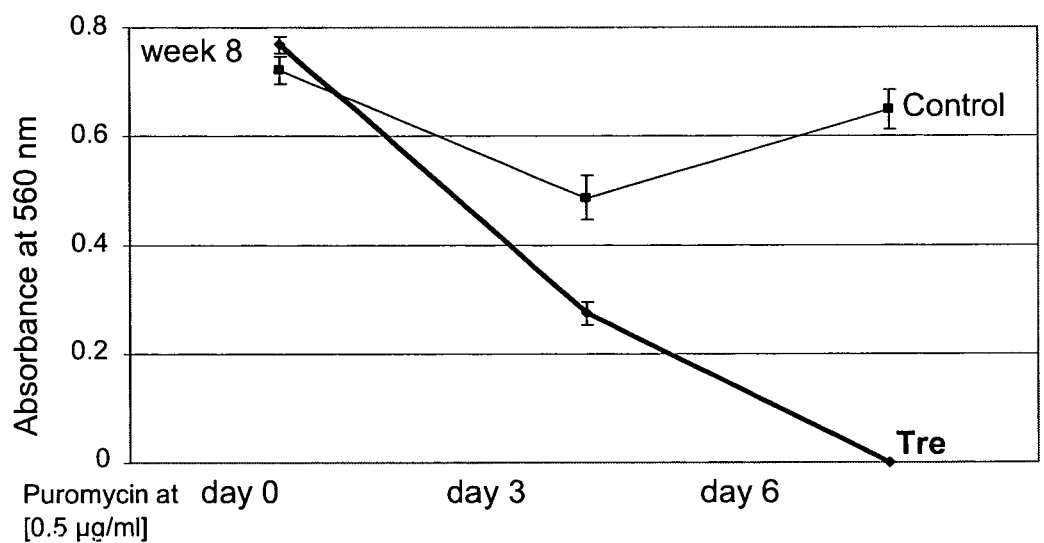
FIG. 11. Tre expressing cells are sensitive to puromycin. Cells from week 8 posttransfection of the Tre-deficient (Control) or Tre expressing (Tre) culture were exposed to 0.5 μg/ml puromycin and monitored over time for cell viability by alamarBlue assay.

The visualisation of Gag expression by laser scanning immunofluorescence microscopy demonstrated the complete disappearance of productively infected cells in the Tre-positive culture over time (see FIG. 10D). For the indirect immunofluorescence microscopy HIV-1 infected HeLa cells were grown on cover slips, washed with PBS without $Ca^{2+}$ and $Mg^{2+}$ and subsequently fixed with 3% paraformaldehyde for 25 min. All incubation steps were carried out at ambient temperature. Following 10 min incubation with 100 mM glycine/PBS, cells were permeabilised in 0.1% Triton X-100/PBS for 4 min and incubated in 1% BSA/PBS for 30 min. Proteins were stained in 1% BSA/PBS using primary antibodies recognising HIV-1 $p55^{Gag}$ (1:100 dilution, Gag-specific HIV-1 mouse monoclonal antibody 183-H12-5C provided by B. Chesebro and K. Wehrly, AIDS Research and Reference Reagent Program, Division AIDS, NIAID, NIH) or rabbit anti-Cre (1:500 dilution) for 45 min, followed by appropriate secondary goat anti-mouse or goat anti-rabbit antibodies (both from Rockland Immunochemicals, Inc.; dilution 1:150) coupled to Cy2. Nuclei were visualised by DRAQ5 staining (dilution 1:1000, Alexis Biochemicals) for 10 min. Cells were mounted in moviol medium and analysed using a Zeiss LSM 510 Meta laser scanning microscope. Interestingly, the re-exposure of these cultures to puromycin at week 8 was survived by the control cells, but resulted in severe toxic effects and ultimate cell death in the Tre-positive culture (see FIG. 11). This observation can be explained by Tre-mediated removal of the proviral gene encoding puromycin resistance (compare to FIG. 10A).

REFERENCE LIST

Abremski K, Hoess RH, Sternberg N (1983) "Studies on the properties of P1 site-specific recombination: evidence for topologically unlinked products following recombination." Cell 32, 1301-1311.

Abremski K, Hoess R (1983) "Bacteriophage P1 site-specific recombination. Purification and properties of the Cre recombinase protein." J. Biol. Chem. 259, 1509-1514.

Adachi A, Gendelman HE, Koenig S, Folks T, Willey R, Rabson A, Martin MA (1986) "Production of acquired immunodeficiency syndrome-associated retrovirus in human and nonhuman cells transfected with an infectious molecular clone." J. Virol. 59, 284-291.

Alper H, Fischer C, Nevoigt E, Stephanopoulos G (2006) "Tuning genetic control through promoter engineering" Proc. Natl. Acad. Sci. USA 102, 12678-12683.

Beyer WR, Westphal M, Ostertag W, von Laer D (2002) "Oncoretrovirus and lentivirus vectors pseudotyped with lymphocytic choriomeningitis virus glycoprotein: generation, concentration and broad host range." J. Virol. 76, 1488-1495.

Blackard JT, Renjifo BR, Mwakagile D, Montano MA, Fawzi WW, Essex M (1999) "Transmission of human immunodeficiency type 1 viruses with intersubtype recombinant long terminal repeat sequences." Virology 254, 220-225.

Bloom JD, Meyer MM, Meinhold P, Otey CR, MacMillan D, Arnold F H (2005) "Evolving strategies for enzyme engineering." Curr. Opin. Struct. Biol. 15, 447-452.

Buchholz F, Ringrose L, Angrand PO, Rossi F, Stewart AF (1996) "Different thermostabilities of FLP and Cre recombinases: implications for applied site-specific recombination." Nucl. Acids Res. 24, 4256-4262.

Buchholz F, Angrand PO, Stewart AF (1998) "Improved properties of FLP recombinase evolved by cycling mutagenesis." Nat. Biotechnol. 16, 657-662.

Buchholz F, Stewart AF (2001) "Alteration of Cre recombinase site specificity by substrate-linked protein evolution." Nat. Biotechnol. 19, 1047-1052.

Chiu YL, Soros VB, Kreisberg JF, Stopak K, Yonemoto W, Greene W C (2005) "Cellular APOBEC3G restricts HIV-1 infection in resting CD4+ T cells." Nature 435, 108-114

Chun T-W, Engel D, Berrey MM, Shea T, Corey L, Fauci AS (1998) "Early establishment of a pool of latently infected, resting CD4+ T cells during primary HIV-1 infection." Proc. Natl. Acad. Sci. USA 95, 8869-8873.

Coates CJ, Kaminski JM, Summers JB, Segal DJ, Miller AD, Kolb A F (2005) "Site-directed genome modification: derivatives of DNA-modifying enzymes as targeting tools." Trends Biotechnol. 23, 407-419.

Collins CH, Yokobayashi Y, Umeno D, Arnold FH, (2003) "Engineering proteins that bind, move, make and break DNA." Curr. Opin. Biotechnol. 14, 665.

Combes P, Till R, Bee S, Smith MC (2002) "The streptomyces genome contains multiple pseudo-attB sites for the (phi)C31-encoded site-specific recombination system." J. Bacteriol. 184, 5746-5752.

Crameri A, Raillard SA, Bermudez E, Stemmer WP (1998) "DNA shuffling of a family of genes from diverse species accelerates directed evolution." Nature 391, 288-291.

Derossi D, Joliot AH, Chassaing G, Prochiantz A (1994) "The thrid helix of the Antennapedia homeodomain translocates through biological membranes." J. Biol. Chem. 269, 10444-10450.

Derossi D, Calvet S, Trembleau A, Chassaing G, Prochiantz A (1996) "Cell internalization of the third helix of the Antennapedia homeodomain is receptor-independent." J. Biol Chem 271, 18188-18193.

Donovan, P. J., Gearhart, J. (2001) "The end of the beginning for pluripotent stem cells." Nature 414, 92-97.

Donzella GA, Schols D, Lin SW, Este JA, Nagashima KA, Maddon PJ, Allaway GP, Sakmar TP, Henson G, De Clercq E, Moore JP (1998) "AMD3100, a small molecule inhibitor of HIV-1 entry via the CXCR4 co-receptor." Nature Medicine 4, 72-77.

Dybul M, Fauci AS, Bartlett JG, Kaplan JE, Pau A K (2002) "Guidelines for using antiretroviral agents among HIV-infected adults and adolescents." *Annals of Internal Medicine* 137, 381-433.

Edelman GM, Meech R, Owens GC, Jones FS (2000) "Synthetic promoter elements obtained by nucleotide sequence variation and selection for activity." *Proc. Natl. Acad. Sci. USA* 97, 3038-3043.

Emerman M, Malim MH (1998) "HIV-1 regulatory/accessory genes: keys to unraveling viral and host cell biology." *Science* 280, 1880-1884.

Finzi D, Hemankova M, Pierson T, Carruth LM, Buck C, Chaisson RE, Quinn TC, Chadwick K, Margolick J, Brookmeyer R, Gallant J, Markowitz M, Ho DD, Richman DD, Siliciano RF (1997) "Identification of a reservoir for HIV-1 in patients on highly active antiretroviral therapy." *Science* 278, 1295-1300.

Flowers CC, Woffendin C, Petryniak J, Yang S, Nabel GJ (1997) "Inhibition of recombinant human immunodeficiency virus type 1 replication by a site-specific recombinase." *J. Virol.* 71, 2685-2692.

Gulick RM, Mellors JW, Havlir D, Eron JJ, Gonzalez C, McMahon D, Richman DD, Valentine FT, Jonas L, Meibohm A, Emini EA, Chodakewitz JA (1997) "Treatment with indinavir, zidovudine, and lamivudine in adults with human immunodeficiency virus infection and prior antiretroviral therapy." *N. Engl. J. Med.* 337, 734-739.

Guzman LM, Belin D, Carson MJ, Beckwith J (1995) "Tight regulation, modulation, and high-level expression by vectors containing the arabinose PBAD promoter." *J. Bacteriol.* 177, 4121-4130.

Hartenbach S, Fussenegger M (2006) "A novel synthetic mammalian promoter derived from an internal ribosome entry site." *Biotechnology and Bioengineering* 95, 547-559.

Hauber I, Bevec D, Heukeshoven J, Krätzer F, Horn F, Choidas A, Harrer T, Hauber J (2005) "Identification of cellular deoxyhypusine synthase as a novel target for antiretroviral therapy." *J. Clin. Invest.* 115, 76-85.

Hazuda DJ, Young SD, Guare JP, Anthony NJ, Gomez RP, Wai JS, Vacca JP, Handt L, Motzel SL, Klein HJ, Dornadula G, Danovich RM, Witmer MV, Wilson KA, Tussey L, Schleif WA, Gabryelski LS, Jin L, Miller MD, Casimiro DR, Emini EA, Shiver JW (2004) "Integrase inhibitors and cellular immunity suppress retroviral replication in rhesus macaques." *Science* 305, 528-532.

Hoess RH, Abremski K (1985) " Mechanism of strand cleavage and exchange in the Cre-lox site-specific recombination system." *J. Mol. Biol.* 181, 351-362.

Johannes TW, Zhao H (2006) "Directed evolution of enzymes and biosynthetic pathways." *Curr. Opin. Microbiol.* 9, 261-267.

Krasnow MA, Cozzarelli NR (1983) "Site-specific relaxation and recombination by the Tn3 resolvase: Recognition of the DNA path between oriented res sites." *Cell* 32, 1313-1324.

Kulkosky J, Bray S (2006) "HAART-persistent HIV-1 latent reservoirs: their origin, mechanisms of stability and potential strategies for eradication." *Curr. HIV Res.* 4, 199-208.

Lalezari JP, Henry K, O'Hearn M, Montaner JS, Piliero PJ, Trottier B, Walmsley S, Cohen C, Kuritzkes DR, Eron Jr. JJ, Chung J, DeMasi R, Donatacci L, Drobnes C, Delehanty J, Salgo M (2003) "Enfuvirtide, an HIV-1 fusion inhibitor, for drug-resistant HIV infection in North and South America." *N. Engl. J. Med.* 348, 2175-2185.

Lee YS, Park JS (1998) "A novel mutant loxP containing part of long terminal repeat of HIV-1 in spacer region: presentation of possible target site for antiviral strategy using site-specific recombinase." *Biochem. Biophys. Res. Comm.* 253, 588-593.

Lee YS, Kim ST, Kim GW, Lee M, Park JS (2000) "An engineered lox sequence containing part of a long terminal repeat of HIV-1 permits Cre recombinase-mediated DNA excision." *Biochem. Cell Biol.* 78, 653-658.

Lehrman G, Hogue IB, Palmer S, Jennings C, Spina CA, Wiegand A, Landay AL, Coombs RW, Richman DD, Mellors JW, Coffin JM, Bosch R J, Margolis D M (2005) "Depletion of latent HIV-1 infection in vivo: a proof-of-concept study" *Lancet* 366, 549-555.

Lewandoski, M. (2001) "Conditional control of gene expression in the mouse." *Nat. Rev. Genet.* 2, 743-755.

Lin Q, Jo D, Gebre-Amlak KD, Ruley HE (2004) "Enhanced cell-permeant Cre protein for site-specific recombination in cultured cells." *BMC Biotechnol.* 4, 25.

Little SJ, Holte S, Routy JP, Daar ES, Markowitz M, Collier A C, Koup RA, Mellors JW, Connick E, Conway B, Kilby M, Wang L, Whitcomb JM, Hellmann NS, Richman DD (2002) "Antiretroviral-drug resistance among patients recently infected with HIV." *N. Engl. J. Med.* 347, 385-394.

Macara IG (2001) "Transport into and out of the nucleus." *Microbiology and molecular biology reviews* 65, 570-594.

Malim MH, Hauber J, Fenrick R, Cullen BR (1988) "Immunodeficiency virus rev trans-activator modulates the expression of the viral regulatory genes." *Nature* 335, 181-183.

Marcello A (2006) "Latency: the hidden HIV-1 challenge." *Retrovirology* 3, 7.

Matsumura I, Ellington AD (2001) "In vitro evolution of beta-glucuronidase into a beta-galactosidase proceeds through non-specific intermediates." *J. Mol. Biol.* 305, 331-339.

Minshull J, Stemmer WP. (1999) "Protein evolution by molecular breeding." *Curr. Opin. Chem. Biol.* 3, 284-290.

Nagy A (2000) "Cre recombinase: the universal reagent for genome tailoring." *Genesis* 26, 99-109.

Needleman SB, Wunsch CD (1970) "A general method applicable to the search for similarities in the amino acid sequence of two proteins." *J. Mol. Biol.* 48, 443-453.

Nolden L, Edenhofer F, Haupt S, Koch P, Wunderlich FT, Siemen H, Brustle O. (2006) "Site-specific recombination in human embryonic stem cells induced by cell-permeant Cre recombinase." *Nat. Methods* 3, 461-467.

O'Doherty U, Swiggard WJ, Malim MH (2000) "Human immunodeficiency virus type 1 spinoculation enhances infection through virus binding." *J. Virol.* 74, 10074-10080.

Pearson WR, Lipman DJ (1988) "Improved tools for biological sequence comparison." *Proc Natl Acad Sci USA* 85, 2444-2448.

Peitz M, Pfannkuche K, Rajewsky K, Edenhofer F. (2002) "Ability of the hydrophobic FGF and basic TAT peptides to promote cellular uptake of recombinant Cre recombinase: A tool for efficient genetic engineering of mammalian genomes." *Proc. Natl. Acad. Sci. USA* 99, 4489-4494.

Ratner L, Starcich B, Josephs SF, Hahn BH, Reddy EP, Livak KJ, Petteway SR, Jr., Pearson ML, Haseltine WA, Arya SK, (1985) "Polymorphism of the 3' open reading frame of the virus associated with the acquired immune deficiency syndrome, human T-lymphotropic virus type III." *Nucl. Acids Res.* 13, 8219-8229.

Richard JP, Melikov K, Brooks H, Prevot P, Lebleu B, Chernomordik L V (2005) "Cellular uptake of the unconjugated TAT peptide involves clathrin-dependent endocytosis and heparin sulfate receptors." *J. Biol. Chem.* 280, 15300-15306.

Rüfer AW, Sauer B (2002) "Non-contact positions impose site selectivity on Cre recombinase." *Nucl. Acids Res.* 30, 2764-2771.

Ruhl M, Himmelspach M, Bahr GM, Hammerschmid F, Jaksche H, Wolff B, Aschauer H, Farrington GK, Probst H, Bevec D, Hauber J (1993) "Eukaryotic initiation factor 5A is a cellular target of the human immunodeficiency virus type 1 Rev activation domain mediating trans-activation" *J. Cell Biol.* 123, 1309-1320.

Sanger F, Nickler S, Coulson A R (1977) "DNA sequencing with chain-terminating inhibitors." *Proc. Natl. Acad. Sci. USA* 74, 5463-5467.

Santoro SW, Schultz PG (2002) "Directed evolution of the site specificity of Cre recombinase." *Proc. Natl. Acad. Sci. USA* 99, 4185-4190.

Saraf-Levy T, Santoro SW, Volpin H, Kushnirsky T, Eyal Y, Schultz PG, Gidoni D, Carmi N (2006) "Site-specific recombination of asymmetric lox sites mediated by a heterotetrameric Cre recombinase complex." *Bioorg. Med. Chem.* 14, 3081-3089.

Sauer B, McDermott J (2004) "DNA recombination with a hetero-specific Cre homolog identified from comparison of the pac-c1 regions of P1-related phages." *Nucl. Acids. Res.* 32, 6086-6095.

Schambach A, Bohne J, Chandra S, Will E, Margison GP, Williams DA, Baum C (2006) "Equal potency of gammaretroviral and lentiviral SIN vectors for expression of $0^6$-methylguanine-DNA methyltransferase in hematoietic cells." *Molecular Therapy* 13, 391-400.

Scherr M, Eder M (2002) "Gene Transfer into Hematopoietic Stem Cells Using Lentiviral Vectors." *Current Gene Therapy* 2, 45-55.

Shehu-Xhilaga M, Tachedjian G, Crowe SM, Kedzierska K. (2005) "Antiretroviral compounds: mechanisms underlying failure of HAART to eradicate HIV-1." *Curr. Med. Chem.* 12, 1705-1719.

Shimshek DR, Kim J, Hubner MR, Spergel DJ, Buchholz F, Casanova E, Stewart AF, Seeburg PH, Sprengel R (2002) "Codon-improved Cre recombinase (iCre) expression in the mouse." *Genesis* 32(1), 19-26.

Smith Tf, Waterman MS (1981) "Overlapping genes and information theory." *J. Theor. Biol.* 91, 379-380.

Stark WM, Boocock MR, Sherratt DJ (1992) "Catalysis by site-specific recombinases." *Trends Genet.* 8, 432-439.

Stemmer WPC (1994) "Rapid evolution of a protein in vitro by DNA shuffling." *Nature* 370, 389-391.

Sternberg N, Hamilton D (1981) "Bacteriophage P1 site-specific recombination. I. Recombination between loxP sites." *J. Mol. Biol.* 150, 467-486.

Van Duyne GD (2001) "A structural view of cre-loxp site-specific recombination." *Annu. Rev. Biophys. Biomol. Struct.* 30, 87-104.

Vives E, Brodin P, Lebleu B (1997) "A truncated HIV-1 Tat protein basic domain rapidly translocates through the plasma membrane and accumulates in the cell nucleus." *J. Biol. Chem.* 272, 16010-16017.

Vives E (2003) "Cellular uptake of the TAT peptide: an endocytosis mechanism following ionic interactions." *J. Mol. Recognit.* 16, 265-271.

Volkert FC, Broach JR (1986) "Site-specific recombination promotes plasmid amplification in yeast." *Cell* 46, 541-550.

Voziyanov Y, Konieczka JH, Stewart AF, Jayaram M (2003) "Stepwise manipulation of DNA specificity in Flp recombinase: progressively adapting Flp to individual and combinatorial mutations in its target site." *J. Mol. Biol.* 326, 65-76.

Yuan L, Kurek I, English J, Keenan R (2005) "Laboratory-directed protein evolution" *Microbiol. Mol. Biol. Rev.* 69, 373-92.

---

SEQUENCE LISTING

```
<160> NUMBER OF SEQ ID NOS: 42

<210> SEQ ID NO 1
<211> LENGTH: 34
<212> TYPE: DNA
<213> ORGANISM: Human immunodeficiency virus type 1
<220> FEATURE:
<221> NAME/KEY: misc_feature
<222> LOCATION: (1)..(13)
<223> OTHER INFORMATION: sequence corresponding to the left half-site of
      the asymmetric target site
<220> FEATURE:
<221> NAME/KEY: misc_feature
<222> LOCATION: (14)..(21)
<223> OTHER INFORMATION: sequence corresponding to the spacer of the
      asymmetric target site
<220> FEATURE:
<221> NAME/KEY: misc_feature
<222> LOCATION: (22)..(34)
<223> OTHER INFORMATION: sequence corresponding to the right half-site
      of the asymmetric target site

<400> SEQUENCE: 1
acaacatcct attacaccct atatgccaac atgg                                 34

<210> SEQ ID NO 2
<211> LENGTH: 1059
<212> TYPE: DNA
<213> ORGANISM: Artificial
<220> FEATURE:
<223> OTHER INFORMATION: artificially prepared Cre variant
```

<400> SEQUENCE: 2

```
atggtgccca agaagaagcg gaaggtgtcc aacctgctga ccctgcacca cagcctgccc      60
gccctgcctg ccgacgccac ctctgacgaa gtgaggaaga acctgatgga cgtgttcaga     120
gacagacccg ccttcagcga gcacacctgg gagatgctgc tgtccgtgtg tagaagctgg     180
gccgcctggt gtaagctgaa caaccggaag tggttccccg ccgagcccga ggatgtgaga     240
gactacctgc tgcacctgca ggccagaggc ctggccgtga aaaccatcca gcagcacctg     300
tgccggctga acatgctgca caggagaagc ggcctgccta cccagcgatcagcaacgcc      360
gtgtccctgg tgatgaggcg gatcaggaag agaacgtgg acgccggcga gaacaaag      420
caggccctgg ccttcgagag aaccgacttc gaccaagtga ggagcctgat ggagaacagc     480
gaccggtgcc aggacatcag aaacctggcc tttctgggcg tggcctacaa caccctgctg     540
aggatcgccg agatcgcccg gatcagggtg aaggacatca gcagaaccga cggcggcaga     600
atgctgatcc acatcggcag gaccaagacc ctggtgtcca cagccggcgt ggagaaggcc     660
ctgagcctgg gcgtgaccaa actggtggag cggtggatca gcgtgtccgg cgtggccgac     720
gaccccaaca actacctgtt ctgtagagtg aggagatatg gcgtggccgc ccccagcgcc     780
acctcccagc tgtccaccta cgccctgcag agaatcttcg aggccaccca cagactgatc     840
tacggcgcca aggatgatag cggccagaga tacctggcct ggagcggcca cagcgccaga     900
gtgggagccg ccagagacat ggccagagcc ggcgtgtcca tccctgagat catgcaggcc     960
ggaggatgga ccaccgtgaa cagcgtgatg aactacatcc ggaacctgga tagcgagacc    1020
ggcgctatgg tgagactgct ggaggacggc gactgatga                           1059
```

<210> SEQ ID NO 3
<211> LENGTH: 351
<212> TYPE: PRT
<213> ORGANISM: Artificial
<220> FEATURE:
<223> OTHER INFORMATION: artificially prepared Cre variant
<220> FEATURE:
<221> NAME/KEY: SIGNAL
<222> LOCATION: (2)..(9)
<223> OTHER INFORMATION: Nuclear localisation sequence (NLS) for directing the protein into the nucleus of mammalian cells

<400> SEQUENCE: 3

```
Met Val Pro Lys Lys Arg Lys Val Ser Asn Leu Leu Thr Leu His
1               5                   10                  15

His Ser Leu Pro Ala Leu Pro Ala Asp Ala Thr Ser Asp Glu Val Arg
            20                  25                  30

Lys Asn Leu Met Asp Val Phe Arg Asp Arg Pro Ala Phe Ser Glu His
        35                  40                  45

Thr Trp Glu Met Leu Leu Ser Val Cys Arg Ser Trp Ala Ala Trp Cys
    50                  55                  60

Lys Leu Asn Asn Arg Lys Trp Phe Pro Ala Glu Pro Glu Asp Val Arg
65                  70                  75                  80

Asp Tyr Leu Leu His Leu Gln Ala Arg Gly Leu Ala Val Lys Thr Ile
                85                  90                  95

Gln Gln His Leu Cys Arg Leu Asn Met Leu His Arg Arg Ser Gly Leu
            100                 105                 110

Pro Arg Pro Ser Asp Ser Asn Ala Val Ser Leu Val Met Arg Arg Ile
        115                 120                 125

Arg Lys Glu Asn Val Asp Ala Gly Glu Arg Thr Lys Gln Ala Leu Ala
```

```
                130              135              140
Phe Glu Arg Thr Asp Phe Asp Gln Val Arg Ser Leu Met Glu Asn Ser
145                 150                 155                 160

Asp Arg Cys Gln Asp Ile Arg Asn Leu Ala Phe Leu Gly Val Ala Tyr
                165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
        195                 200                 205

Lys Thr Leu Val Ser Thr Ala Gly Val Glu Lys Ala Leu Ser Leu Gly
    210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Arg Tyr Gly Val Ala
                245                 250                 255

Ala Pro Ser Ala Thr Ser Gln Leu Ser Thr Tyr Ala Leu Gln Arg Ile
            260                 265                 270

Phe Glu Ala Thr His Arg Leu Ile Tyr Gly Ala Lys Asp Asp Ser Gly
        275                 280                 285

Gln Arg Tyr Leu Ala Trp Ser Gly His Ser Ala Arg Val Gly Ala Ala
    290                 295                 300

Arg Asp Met Ala Arg Ala Gly Val Ser Ile Pro Glu Ile Met Gln Ala
305                 310                 315                 320

Gly Gly Trp Thr Thr Val Asn Ser Val Met Asn Tyr Ile Arg Asn Leu
                325                 330                 335

Asp Ser Glu Thr Gly Ala Met Val Arg Leu Leu Glu Asp Gly Asp
            340                 345                 350

<210> SEQ ID NO 4
<211> LENGTH: 67
<212> TYPE: DNA
<213> ORGANISM: Artificial
<220> FEATURE:
<223> OTHER INFORMATION: oligonucleotide primer

<400> SEQUENCE: 4
atgagatcta caacatccta ttacacccta tatgccaaca tggaagcttg catgcctgca    60
gatcgag                                                             67

<210> SEQ ID NO 5
<211> LENGTH: 57
<212> TYPE: DNA
<213> ORGANISM: Artificial
<220> FEATURE:
<223> OTHER INFORMATION: oligonucleotide primer

<400> SEQUENCE: 5
ttgagatcta caacatccta tatgccaaca tggtcgaact gtaccggttg ttagtga      57

<210> SEQ ID NO 6
<211> LENGTH: 67
<212> TYPE: DNA
<213> ORGANISM: Artificial
<220> FEATURE:
<223> OTHER INFORMATION: oligonucleotide primer

<400> SEQUENCE: 6
atgagatcta caacatccta ttacacccta aataggatgt tgtaagcttg catgcctgca   60
``` gatcgag 67

<210> SEQ ID NO 7
<211> LENGTH: 67
<212> TYPE: DNA
<213> ORGANISM: Artificial
<220> FEATURE:
<223> OTHER INFORMATION: oligonucleotide primer

<400> SEQUENCE: 7
ttgagatcta caacatccta ttacaccta aataggatgt tgttcgaact gtaccggttg    60
ttagtga    67

<210> SEQ ID NO 8
<211> LENGTH: 67
<212> TYPE: DNA
<213> ORGANISM: Artificial
<220> FEATURE:
<223> OTHER INFORMATION: oligonucleotide primer

<400> SEQUENCE: 8
atgagatctc catgttggca taacacccta tatgccaaca tggaagcttg catgcctgca    60
gatcgag    67

<210> SEQ ID NO 9
<211> LENGTH: 67
<212> TYPE: DNA
<213> ORGANISM: Artificial
<220> FEATURE:
<223> OTHER INFORMATION: oligonucleotide primer

<400> SEQUENCE: 9
ttgagatctc catgttggca taacacccta tatgccaaca tggtcgaact gtaccggttg    60
ttagtga    67

<210> SEQ ID NO 10
<211> LENGTH: 67
<212> TYPE: DNA
<213> ORGANISM: Artificial
<220> FEATURE:
<223> OTHER INFORMATION: oligonucleotide primer

<400> SEQUENCE: 10
atgagatcta caacatcgta taacacccta tatacgatgt tgtaagcttg catgcctgca    60
gatcgag    67

<210> SEQ ID NO 11
<211> LENGTH: 67
<212> TYPE: DNA
<213> ORGANISM: Artificial
<220> FEATURE:
<223> OTHER INFORMATION: oligonucleotide primer

<400> SEQUENCE: 11
ttgagatcta caacatcgta taacacccta tatacgatgt tgttcgaact gtaccggttg    60
ttagtga    67

<210> SEQ ID NO 12
<211> LENGTH: 67
<212> TYPE: DNA
<213> ORGANISM: Artificial
<220> FEATURE:
<223> OTHER INFORMATION: oligonucleotide primer

```
<400> SEQUENCE: 12
atgagatcta taacttccta ttacacccta aataggaagt tataagcttg catgcctgca    60
gatcgag                                                              67

<210> SEQ ID NO 13
<211> LENGTH: 67
<212> TYPE: DNA
<213> ORGANISM: Artificial
<220> FEATURE:
<223> OTHER INFORMATION: oligonucleotide primer

<400> SEQUENCE: 13
ttgagatcta taacttccta ttacacccta aataggaagt tattcgaact gtaccggttg    60
ttagtga                                                              67

<210> SEQ ID NO 14
<211> LENGTH: 67
<212> TYPE: DNA
<213> ORGANISM: Artificial
<220> FEATURE:
<223> OTHER INFORMATION: oligonucleotide primer

<400> SEQUENCE: 14
atgagatctc catcttcgta taacacccta tatacgaaga tggaagcttg catgcctgca    60
gatcgag                                                              67

<210> SEQ ID NO 15
<211> LENGTH: 67
<212> TYPE: DNA
<213> ORGANISM: Artificial
<220> FEATURE:
<223> OTHER INFORMATION: oligonucleotide primer

<400> SEQUENCE: 15
ttgagatctc catcttcgta taacacccta tatacgaaga tggtcgaact gtaccggttg    60
ttagtga                                                              67

<210> SEQ ID NO 16
<211> LENGTH: 67
<212> TYPE: DNA
<213> ORGANISM: Artificial
<220> FEATURE:
<223> OTHER INFORMATION: oligonucleotide primer

<400> SEQUENCE: 16
atgagatcta taagttggca taacacccta tatgccaact tataagcttg catgcctgca    60
gatcgag                                                              67

<210> SEQ ID NO 17
<211> LENGTH: 67
<212> TYPE: DNA
<213> ORGANISM: Artificial
<220> FEATURE:
<223> OTHER INFORMATION: oligonucleotide primer

<400> SEQUENCE: 17
ttgagatcta taagttggca taacacccta tatgccaact tattcgaact gtaccggttg    60
ttagtga                                                              67

<210> SEQ ID NO 18
```

```
<211> LENGTH: 18
<212> TYPE: DNA
<213> ORGANISM: Artificial
<220> FEATURE:
<223> OTHER INFORMATION: oligonucleotide primer

<400> SEQUENCE: 18
caataaccct gataaatg                                                 18

<210> SEQ ID NO 19
<211> LENGTH: 17
<212> TYPE: DNA
<213> ORGANISM: Artificial
<220> FEATURE:
<223> OTHER INFORMATION: oligonucleotide primer

<400> SEQUENCE: 19
tctactgttt ctccata                                                  17

<210> SEQ ID NO 20
<211> LENGTH: 17
<212> TYPE: DNA
<213> ORGANISM: Artificial
<220> FEATURE:
<223> OTHER INFORMATION: oligonucleotide primer

<400> SEQUENCE: 20
tgtcgccctt attccct                                                  17

<210> SEQ ID NO 21
<211> LENGTH: 17
<212> TYPE: DNA
<213> ORGANISM: Artificial
<220> FEATURE:
<223> OTHER INFORMATION: oligonucleotide primer

<400> SEQUENCE: 21
gcggatgaga gaagatt                                                  17

<210> SEQ ID NO 22
<211> LENGTH: 19
<212> TYPE: DNA
<213> ORGANISM: Artificial
<220> FEATURE:
<223> OTHER INFORMATION: oligonucleotide primer

<400> SEQUENCE: 22
gcctcggcct aggaacagt                                                19

<210> SEQ ID NO 23
<211> LENGTH: 20
<212> TYPE: DNA
<213> ORGANISM: Artificial
<220> FEATURE:
<223> OTHER INFORMATION: oligonucleotide primer

<400> SEQUENCE: 23
ccgccacata tcctgatctt                                               20

<210> SEQ ID NO 24
<211> LENGTH: 20
<212> TYPE: DNA
<213> ORGANISM: Artificial
<220> FEATURE:
<223> OTHER INFORMATION: oligonucleotide primer

<400> SEQUENCE: 24
```
gaaggtgggt tttccagtca                                              20

<210> SEQ ID NO 25
<211> LENGTH: 20
<212> TYPE: DNA
<213> ORGANISM: Artificial
<220> FEATURE:
<223> OTHER INFORMATION: oligonucleotide primer

<400> SEQUENCE: 25
agggaagaaa gcgaaaggag                                              20

<210> SEQ ID NO 26
<211> LENGTH: 21
<212> TYPE: DNA
<213> ORGANISM: Artificial
<220> FEATURE:
<223> OTHER INFORMATION: oligonucleotide primer

<400> SEQUENCE: 26
atcaatgagg aagctgcaga a                                            21

<210> SEQ ID NO 27
<211> LENGTH: 21
<212> TYPE: DNA
<213> ORGANISM: Artificial
<220> FEATURE:
<223> OTHER INFORMATION: oligonucleotide primer

<400> SEQUENCE: 27
gataggtgga ttatgtgtca t                                            21

<210> SEQ ID NO 28
<211> LENGTH: 24
<212> TYPE: DNA
<213> ORGANISM: Artificial
<220> FEATURE:
<223> OTHER INFORMATION: oligonucleotide probe labelled with FAM at the
      5'-end and with TAMRA at the 3'-end

<400> SEQUENCE: 28
attgcaccag gccagatgag agaa                                         24

<210> SEQ ID NO 29
<211> LENGTH: 21
<212> TYPE: DNA
<213> ORGANISM: Artificial
<220> FEATURE:
<223> OTHER INFORMATION: oligonucleotide primer

<400> SEQUENCE: 29
gatggtgcta caagctagta c                                            21

<210> SEQ ID NO 30
<211> LENGTH: 21
<212> TYPE: DNA
<213> ORGANISM: Artificial
<220> FEATURE:
<223> OTHER INFORMATION: oligonucleotide primer

<400> SEQUENCE: 30
ctgtcaaacc tccactctaa c                                            21

<210> SEQ ID NO 31
<211> LENGTH: 26

```
<212> TYPE: DNA
<213> ORGANISM: Artificial
<220> FEATURE:
<223> OTHER INFORMATION: oligonucleotide probe labelled with FAM at the
      5'-end and with TAMRA at the 3'-end

<400> SEQUENCE: 31
aaggagagaa caacatccta ttacac                                              26

<210> SEQ ID NO 32
<211> LENGTH: 25
<212> TYPE: DNA
<213> ORGANISM: Artificial
<220> FEATURE:
<223> OTHER INFORMATION: oligonucleotide primer

<400> SEQUENCE: 32
cttaatgcct taacattgtg tataa                                               25

<210> SEQ ID NO 33
<211> LENGTH: 26
<212> TYPE: DNA
<213> ORGANISM: Artificial
<220> FEATURE:
<223> OTHER INFORMATION: oligonucleotide primer

<400> SEQUENCE: 33
gaatatgcaa ataagcacac atatat                                              26

<210> SEQ ID NO 34
<211> LENGTH: 28
<212> TYPE: DNA
<213> ORGANISM: Artificial
<220> FEATURE:
<223> OTHER INFORMATION: oligonucleotide probe labelled with FAM at the
      5'-end and with TAMRA at the 3'-end

<400> SEQUENCE: 34
actttacaca gtctgcctag tacattac                                            28

<210> SEQ ID NO 35
<211> LENGTH: 34
<212> TYPE: DNA
<213> ORGANISM: Bacteriophage P1

<400> SEQUENCE: 35
ataacttcgt ataatgtatg ctatacgaag ttat                                     34

<210> SEQ ID NO 36
<211> LENGTH: 34
<212> TYPE: DNA
<213> ORGANISM: Human immunodeficiency virus type 1

<400> SEQUENCE: 36
acaacatcct attacaccct atatgccaac atgg                                     34

<210> SEQ ID NO 37
<211> LENGTH: 34
<212> TYPE: DNA
<213> ORGANISM: Artificial Sequence
<220> FEATURE:
<223> OTHER INFORMATION: LoxLTR1

<400> SEQUENCE: 37
acaacatcct attacaccct aaataggatg ttgt                                     34
```

```
<210> SEQ ID NO 38
<211> LENGTH: 34
<212> TYPE: DNA
<213> ORGANISM: Artificial Sequence
<220> FEATURE:
<223> OTHER INFORMATION: LoxLTR1a

<400> SEQUENCE: 38
acaacatcgt ataacaccct atatacgatg ttgt                              34

<210> SEQ ID NO 39
<211> LENGTH: 34
<212> TYPE: DNA
<213> ORGANISM: Artificial Sequence
<220> FEATURE:
<223> OTHER INFORMATION: LoxLTR1b

<400> SEQUENCE: 39
ataacttcct attacaccct aaataggaag ttat                              34

<210> SEQ ID NO 40
<211> LENGTH: 34
<212> TYPE: DNA
<213> ORGANISM: Artificial Sequence
<220> FEATURE:
<223> OTHER INFORMATION: LoxLTR2

<400> SEQUENCE: 40
ccatgttggc ataacaccct atatgccaac atgg                              34

<210> SEQ ID NO 41
<211> LENGTH: 34
<212> TYPE: DNA
<213> ORGANISM: Artificial Sequence
<220> FEATURE:
<223> OTHER INFORMATION: LoxLTR2a

<400> SEQUENCE: 41
ccatcttcgt ataacaccct atatacgaag atgg                              34

<210> SEQ ID NO 42
<211> LENGTH: 34
<212> TYPE: DNA
<213> ORGANISM: Artificial Sequence
<220> FEATURE:
<223> OTHER INFORMATION: LoxLTR2b

<400> SEQUENCE: 42
ataagttggc ataacaccct atatgccaac ttat                              34
```

The invention claimed is:

1. A method for preparing an expression vector encoding a single tailored recombinase, which tailored recombinase recombines asymmetric target sequences within the LTR of proviral DNA inserted into the genome of a host cell comprising the steps of
   (a) determining the sequence of the LTR of the proviral DNA, identifying therein sequences with homology of at least 30% to left half-site and right half-site sequences of known target sites of recombinases, wherein the homologous sequences of the LTR of the proviral DNA are separated by a spacer of 5-12 nucleotides, and wherein the homologous sequences of the LTR of the proviral DNA with highest homology to a known target site comprise the asymmetric target sequences;
   (b) preparing a first and second synthetic sequence, wherein the first synthetic sequence comprises the sequence of the asymmetric target sequences of step (a) homologous to the left half-site of said known target site (half-site sequence 1), and wherein the second synthetic sequence comprises the sequence of the asymmetric target sequences of step (a) homologous to the right half-site (half-site sequence 2);
   (c) determining the nucleotides within the synthetic sequences of step (b) deviating from the homologous left half-site and right half-site sequences of the known target site of the recombinase of step (a);
   (d) generating a first subset of two target sequences on the basis of the synthetic sequences of step (b), wherein the first target sequence in the first subset comprises an inverted repeat consisting of half-site sequence 1 and half-site sequence 1' separated by the spacer sequence, and wherein the second target sequence in the first subset comprises an inverted repeat consisting of half-site sequence 2' and half-site sequence 2 separated by the spacer sequence, wherein half-site sequences 1' and 2' are inverted repeats of the respective half-site sequences 1 and 2 of step (b);

(e) generating a second subset of target sequences on the basis of the target sequences in the first subset of step (d), wherein each of the half-site sequences together with the respective spacer sequence of the target sequences in the first subset of step (d) is used to generate an independent target sequence of the second subset by forming an inverted repeat such that the spacer sequence separates both sequences forming the inverted repeat, wherein the sequences of both half-site sequences originating from one of the target sequences in the first subset of step (d) are altered during their synthesis and prior to using same for generating the inverted repeat yielding the complete target sequence such that (1) in the left half-site sequence, a portion of the nucleotides deviating from the homologous half-site sequence of the known target-site of step (a) is replaced by the native nucleotides found in the known target- site, and in the fight half-site sequence, the rest of the nucleotides deviating from the homologous left half-site is replaced by the native nucleotides found in the known target-site, and (2) in both half-site sequences originating from one target sequence of the first subset of step (d) taken together all deviating nucleotides can be found, whereas none of said half half-site sequences alone comprises all deviating nucleotides;

(f) generating further subsets of target sequences starting from the target sequences in the second subset obtained in step (e) by repeating the process of step (e) each time generating a new subset of target sequences, until the half-site sequences forming the inverted repeats within each generated target sequence contain one, two or three nucleotides deviating from the homologous half-site sequence of the known target site;

(g) applying molecular directed evolution on the recombinase recognizing the known homologous target site chosen in step (a) using the target sequences of the final subset obtained in step (f) containing one, two or three nucleotides deviating from the homologous half-site sequence of said known homologous target site as a substrate;

(h) shuffling the recombinase libraries evolved in step (g);

(i) applying molecular directed evolution on the shuffled library obtained in step (h) using the target sequences of the next higher subset according to step (f);

(j) repeating steps (h) and (i) until one recombinase is achieved by molecular directed evolution that is active on the asymmetric target sequence within the LTR of the proviral DNA of step (a);

(k) isolating the nucleic acid encoding the one recombinase obtained in step (j) from the library; and (l) cloning the nucleic acid obtained in step (k) into an expression vector, thereby preparing an expression vector encoding a single recombinase that is active on the asymmetric target sequence, wherein the single recombinase that is active on the asymmetric target sequence has only a residual activity or no activity on (1) the known target site of the recombinase of step (a), and (2) at least one of the subsets of target sequences generated in steps (d) to (f).

2. The method according to claim 1, wherein the known recombinase whose target sequence is used in step (a) and upon which molecular directed evolution is applied in steps (g) and (i) belongs to the family of serine integrases or tyrosine integrases.

3. The method according to claim 1, wherein the known recombinase whose target sequence is used in step (a) and upon which molecular directed evolution is applied in steps (g) and (i) belongs to the family of tyrosine integrases and is Cre from Phage P1, FLP from yeast, or Dre from phage D6.

4. The method according to claim 1, wherein the asymmetric target sequence identified in step (a) is localized in both the 5'-LTR and the 3'- LTR of the provirus.

5. The method according to claim 4, wherein the proviral DNA inserted into the genome of a host cell is the DNA of a retrovirus selected from the group consisting of Mouse mammary tumor virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV), or a lentivirus selected from the group consisting of Human immunodeficiency virus Type 1 (HIV-1), Human immunodeficiency virus Type 2 (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV).

6. The method according to claim 5, wherein the asymmetric target sequence identified in step (a) is localized in both the 5'-LTR and the 3'- LTR of a HIV provirus.

7. The method according to claim 6, wherein the asymmetric target sequence identified in step (a) localized in both the 5'-LTR and the 3'-LTR of an HIV provirus has the sequence set forth as SEQ ID NO:1.

8. The method according to claim 1, wherein the molecular directed evolution employed is substrate-linked protein evolution.

9. The method according to claim 1, wherein the expression vector in step (1) is selected from the group consisting of retroviral vectors, lentiviral vectors, spumavirus vectors and adenoviral vectors.

10. The method according to claim 1, further comprising expressing the tailored recombinase or a fusion polypeptide comprising the amino acid sequence of the tailored recombinase from the nucleic acid encoding the recombinase inserted into the expression vector in a host cell.

11. The method according to claim 1, further comprising introducing the expression vector in vitro into an adult stem cell.

12. The method according to claim 1, further comprising preparing a composition comprising the expression vector, the recombinase that is active on the asymmetric target sequence, a fusion protein comprising the amino acid sequence of the recombinase that is active on the asymmetric target sequence, or an adult stem cell comprising the expression vector; and a pharmaceutically acceptable excipient.

13. The method according to claim 6, wherein the asymmetric target sequence identified in step (a) localized in both the 5'-LTR and the 3'-LTR of an HIV provirus has at least 70% sequence identity to the sequence as set forth in SEQ ID NO:1.

14. The method of claim 1, wherein the single recombinase that is active on the asymmetric target sequence has no activity or only a residual activity on the first subset of target sequences generated step (d).

* * * * *